US012613239B2

(12) United States Patent
Di Nunzio

(10) Patent No.: US 12,613,239 B2
(45) Date of Patent: Apr. 28, 2026

(54) LIVE IMAGING SYSTEM TO VISUALIZE THE RETRO-TRANSCRIBED VIRAL DNA GENOME

(71) Applicants: INSTITUT PASTEUR, Paris (FR); NEOVIRTECH, Toulouse (FR)

(72) Inventor: Francesca Di Nunzio, Paris (FR)

(73) Assignee: INSTITUT PASTEUR, Paris (FR)

( * ) Notice: Subject to any disclaimer, the term of this patent is extended or adjusted under 35 U.S.C. 154(b) by 1205 days.

(21) Appl. No.: 17/607,118

(22) PCT Filed: Apr. 11, 2020

(86) PCT No.: PCT/IB2020/000456
§ 371 (c)(1),
(2) Date: Apr. 26, 2022

(87) PCT Pub. No.: WO2020/229893
PCT Pub. Date: Nov. 19, 2020

(65) Prior Publication Data
US 2025/0044282 A1 Feb. 6, 2025

Related U.S. Application Data

(60) Provisional application No. 62/846,201, filed on May 10, 2019.

(51) Int. Cl.
*G01N 33/50* (2006.01)
*C12N 15/86* (2006.01)

(52) U.S. Cl.
CPC ......... *G01N 33/5091* (2013.01); *C12N 15/86* (2013.01); *C12N 2740/16022* (2013.01); *C12N 2740/16043* (2013.01); *G01N 2500/10* (2013.01)

(58) Field of Classification Search
CPC .. C07K 14/195; C07K 2319/80; C12N 15/86; C12N 2740/16022; C12N 2740/16043; C12Q 1/18; G01N 2333/16; G01N 2333/165; G01N 2500/10; G01N 33/5091
See application file for complete search history.

(56) References Cited

FOREIGN PATENT DOCUMENTS

WO 2012/127047 A1 9/2012

OTHER PUBLICATIONS

Mariame et al. J Virol, published on Aug. 29, 2018; vol. 92(18): e00571-18.*
Verghese et al. Nucleic Acids Research, published on 2014, vol. 42, No. 7, pp. e1-e13.*
McDonald, D. et al. (2002). Visualization of the intracellular behavior of HIV in living cells. The Journal of cell biology 159, 441-452.

Di Nunzio, F. et al. (2013). Nup153 and Nup98 bind the HIV-1 core and contribute to the early steps of HIV-1 replication. Virology 440, 8-18.
Di Nunzio, F. et al. (2012). Human nucleoporins promote HIV-1 docking at the nuclear pore, nuclear import and integration. PloS one 7, e46037. 1-15.
Lee, K. et al. (2010). Flexible use of nuclear import pathways by HIV-1. Cell host & microbe 7, 221-233.
Francis A. C. & Melikyan, G. B.(2018) "Single HIV-1 Imaging Reveals Progression of Infection through CA-Dependent Steps of Docking at the Nuclear Pore, Uncoating, and Nuclear Transport", Cell Host & Microbe, vol. 23, No. 4, Apr. 1, 2018, pp. 536-548.
Francis, A. C., et al (2016). Time-Resolved Imaging of Single HIV-1 Uncoating In Vitro and in Living Cells. PLoS pathogens 12, 1-28.
Mamede, J. I., et al (2017). Early cytoplasmic uncoating is associated with infectivity of HIV-1. Proceedings of the National Academy of Sciences of the United States of America 114, E7169-E7178.
Peng, K. et al. (2014). Quantitative microscopy of functional HIV post-entry complexes reveals association of replication with the viral capsid. Elife 3, 1-21.
Marini, B. et al. (2015). Nuclear architecture dictates HIV-1 integration site selection. Nature 521, 227-231, doi:10.1038/nature14226.
Stultz, R. D., et al.(2017). "Imaging HIV-1 Genomic DNA from Entry through Productive Infection", Journal of Virology, vol. 91, No. 9, pp. 1-19.
Mariamé, B. et al. (2018) "Real-Time Visualization and Quantification of Human Cytomegalovirus Replication in Living Cells Using the Anchor Dna Labeling Technology", Journal of Virology, vol. 92, No. 18, pp. 1-22.

(Continued)

*Primary Examiner* — Bao Q Li
(74) *Attorney, Agent, or Firm* — Arrigo, Lee, Guttman & Mouta-Bellum LLP

(57) ABSTRACT

A recombinant lentiviral vector comprising a coding sequence for an OR protein fused to a coding sequence for a fluorescent protein or a subunit of a fluorescent protein, and a promoter active in human cells operatively linked to the coding sequences. A recombinant lentivirus comprising a recombinant genome comprising an RNA that generates an ANCH sequence upon retrotranscription. A recombinant eukaryotic cell comprising a genomically integrated DNA copy of the recombinant lentiviral vector. A method of observing lentiviral DNA in a eukaryotic cell, comprising: providing a recombinant eukaryotic cell that produces a fusion protein comprising an OR protein, fused to a fluorescent protein or a subunit of a fluorescent protein; infecting the recombinant eukaryotic cell with a recombinant lentivirus comprising a recombinant genome comprising an RNA that generates an ANCH sequence upon retro-transcription, under conditions sufficient for reverse transcription of the recombinant lentiviral genome comprising an ANCH sequence; allowing the OR protein to bind to the ANCH sequence; and detecting the fluorescent protein or subunit of the fluorescent protein to thereby observe the lentiviral DNA in the eukaryotic cell. This tool can be suitable also for in vivo applications (e.g. humanized mice) as well as for screening of new antiretroviral compounds. The HIV-1 ANCHOR system can be extended to the study of other viruses or for the screening of antiviral compounds, e.g. against SARS-CoV2.

18 Claims, 26 Drawing Sheets

Specification includes a Sequence Listing.

(56)         References Cited

OTHER PUBLICATIONS

Graham, T. G. et al. (2014). ParB spreading requires DNA bridging. Genes & development 28, 1228-1238.

Sanchez, A. et al. (2015). Stochastic Self-Assembly of ParB Proteins Builds the Bacterial DNA Segregation Apparatus. Cell Syst 1, 163-173.

Di Primio, C. et al. (2013) Single-cell imaging of HIV-1 provirus (SCIP). Proceedings of the National Academy of Sciences of the United States of America 110, 5636-5641.

Saito, A. et al. (2016). Roles of Capsid-Interacting Host Factors in Multimodal Inhibition of HIV-1 by PF74. Journal of virology 90, 5808-5823.

Ruelas DS, Greene WC. (2013). An integrated overview of HIV-1 latency. Cell. 155(3):519-529.

Blanco-Rodriguez G., et al., (2020). Remodeling of the core leads HIV-1 pre-integration complex in the nucleus of human lymphocytes. bioRxiv, p. 1-38. https://doi.org/10.1101/2020.01.24.918383.

Komatsu et al. (2018). In Vivo Labelling of Adenovirus DNA Identifies Chromatin Anchoring and Biphasic GenomeReplication, Journal of Virology, vol. 92, No. 18, 11, pp. 1-21.

Saad H, et al. (2014). DNA dynamics during early double-strand break processing revealed by non-intrusive imaging of living cells. PLoS Genetics. 10(3). 1-11.

Germier et al. (2017). Real-Time imaging of a single gene reveals transcription-initiated loca confinement. Biophysical Journal, 113, 1383-1394.

Blanco-Rodriguez et al. (2020). Remodeling of the Core Leads HIV-1 Preintegration Complex into the Nucleus of Human Lymphocytes. Journal of Virology. 94(11). 1-20.

* cited by examiner c d a b a Infectivity primary Lymphocytes b c

**HeLa cells infected
with HIV-1 Env WT**

FIG.9

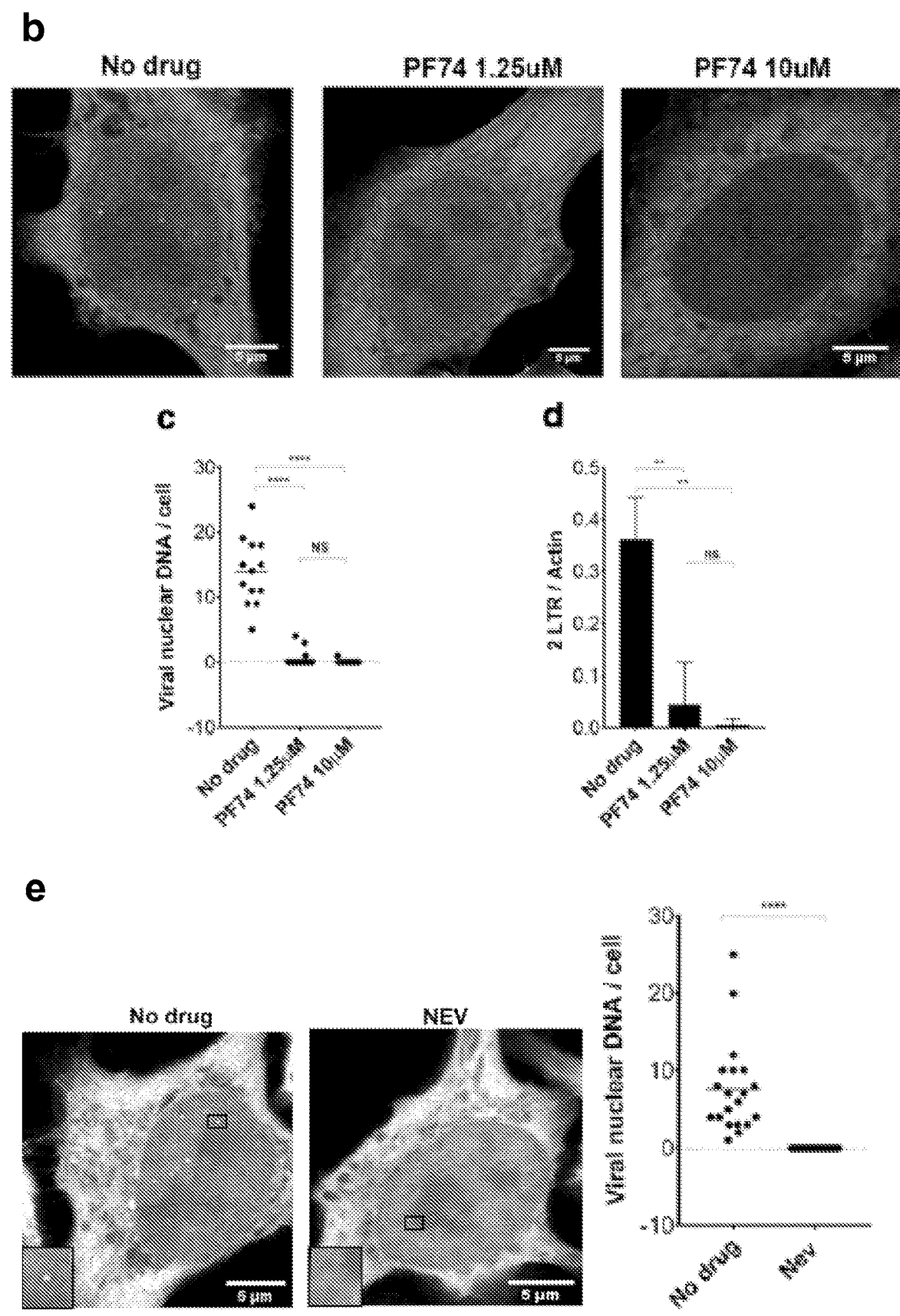
FIG.11cont'd

Live track of viral DNA in the nucleus of HIV-1 natural target cells

Macrophages like-cells

CD4+ T cells derived from healthy donors b

INTEGRATED forms

HIV-1 ANCH3 Clone

HIV-1 ANCHOR is highly sensitive system to detect a single integration a

HIV-1 ANCH3 IN

HIV-1 ANCH3 4 FAIL c    Primary CD4+ T cells vDNA detected by ANCHOR co-localize with host / viral factors important for the integration step CD4+ T cells and macrophages are considered the cells that form the viral reservoir

FIG.14 b     Live imaging to study the dynamic viral transcription

HeLa P4R5 cells

HIV-1 ANCH3MS2 viral RNA foci 24 h post infection in HeLa P4R5 cells:
uninfected cells (NI), infected cells at MOI 10 and MOI 100

CD4+T cells

HIV-1 ANCH3MS2 viral RNA foci 72 h post infection in primary CD4+T cells:
uninfected cells (NI) and infected cells at MOI 30.

a     Study of viral persistence using humanized mice

Single cell live imaging for a fast and efficient drugs screen a b c

SARS-CoV2 system tested using Hydroxychloroquine (HCQ)

Without drugs

HCQ 50uM

LIVE IMAGING SYSTEM TO VISUALIZE THE RETRO-TRANSCRIBED VIRAL DNA GENOME

BACKGROUND

Direct detection of HIV-1 genomes after reverse transcription has been a technological challenge to study HIV-1 preintegration complex morphogenesis, as well as viral integration sites distribution. Fluorescence in situ hybridization (FISH) has been used to detect HIV-1 Integration sites (Marini et al., Nature 2015), but the harsh sample preparation processing destroys the morphological context, often not compatible with electron microscopy or Immune fluorescence approaches. Metabolic labeling of viral genomes is another recently developed technique for detecting incoming single viral genomes as well as replication viral DNA in cells. For this approach, viruses are replicated in cells supplemented with chemically modified nucleoside analogs such as EdU (S-ethynyl-2'-deoxyuridine). In the case of HIV-1 the EdU is incorporated in the newly retrotranscribed DNA. It has been shown (Peng et al., elife 2014) that the viral genome can be detected by EdU incorporation once retrotranscribed, however EdU can be easily incorporated into the host genome during DNA replication, in particular there is incorporation even if Hela cells are blocked in cycle by aphidicolin treatment, limiting the applicability of this tool. Briefly, individual genomes can be visualized using click-chemistry under mild conditions compatible with antibody detection exclusively in fixed naturally non-dividing cells. EdU by itself is toxic so cannot be easily used to follow long term infection in the cells. For all of these reasons systems to follow in vivo HIV-1 infection and integration of the viral genome into the host chromatin has been lacking. This invention meets these and other needs.

SUMMARY OF THE INVENTION

As disclosed herein, the inventors have set up a new non-invasive system, perfectly compatible with the survival of infected cells. This system can be applicable to the major target cells of HIV, such as CD4+ T cells and macrophages and even in primary cells, such CD4+ lymphocytes derived by patients. This system is also applicable to any type of eukaryotic cells, preferably human cells, genetically modified to express a receptor recognized by a viral envelope for viral entry.

Characterizing the fate of viral genomes is important for understanding the viral life cycle and the fate of virus-derived vector tools. The inventors have integrated the ANCHOR3 system, an in vivo DNA tagging technology commercialized by the Neo VirTech SAS company (Toulouse, France), an optimized version of the ANCHOR system patented in WO2012127047. The inventions provided herein enable following the fate of HIV-1 immediately after the reverse transcription step. The OR-GFP cDNA was cloned in the lentiviral vector pFlap (WO1999055892; WO2001027300) under the control of the CMV promoter or other eukaryotic promoters like EF1a. Anch3 sequence has been cloned into the genome of HIV-1 for real time genome detection. The examples demonstrate detecting punctate GFP spots into the nucleus of Hela P4R5 cells 24 h post-Infection (FIG. 1). The control shows some GFP prevalently located into the cytoplasm, because ORGFP lacks a nuclear localization signal. Several conditions were analyzed to set up the system. Stable cell lines were generated at different multiplicity of infection (MOI), before identifying the one shown in FIG. 1. As shown in FIG. 1 in the control there are no GFP spots detected, because OR protein specifically interacts with Anch3 sequences, which are not present into the human genome. Importantly the presence of ORGFP bound to the Anch3 sequences cloned into the viral genome does not affect viral expression. (FIG. 2.) This is shown by the coupling of viral integration and transcription that will allow to study the phenomenon of HIV-1 latency which remains the main obstacle to curing AIDS.

The examples demonstrate that early steps of HIV-1 infection can be followed in live cells (FIG. 3). This technology can be applied to follow viral infection in different cells, even primary cells and/or in the context of cell to cell transmission. New drug compounds can be easily screened using this system. In the examples, two different drugs have been already tested showing the efficiency of HIV-1 ANCHOR system as tool for drug screening. Of note HIV-1 ANCHOR is the only fluorescence system allowing to specifically detect the viral DNA that can be successfully coupled to electron microscopy. This approach can be enlarged to other genes, viral and not, for structural studies based on correlative microscopy (fluorescence-electron microscopy). This approach can be also a critical tool for drug discovery. Bio-distribution of the highly promising HIV-1 derived vectors, which are already successfully used in some gene therapy or vaccinology approaches can also be studied using HIV-AnchOR3 system. These and other systems, reagents, methods, etc. are disclosed herein.

As used herein, lentiviruses include, without limitation, human immunodeficiency viruses (HIV-1 and HIV-2), the simian immunodeficiency virus (SIV), the equine infectious encephalitis virus (EIAV), the caprine arthritis encephalitis virus (CAEV), the bovine immunodeficiency virus (BIV), Human T-lymphotropic virus (HTLV) and the feline immunodeficiency virus (FIV). This technology can be used for all retroviruses: lentiviruses, betaretroviruses, alfaretroviruses, spumaviruses, epsilonretroviruses, gammaretroviruses and deltaretroviruses. In particular HIV-1 ANCHOR system can be applied to pseudotyped particles, this can extend this application to all other viruses also with RNA genome, which are not retroviruses, such as SARS-CoV, SARS-CoV2, Ebola, Flu viruses and all envelope of viruses that can be used to pseudotype retroviral particles carrying the ANCHOR system.

The system can advantageously be applied to pseudotyped lentiviruses or retroviruses, modified to express any other viral envelope proteins of a second virus, as a surrogate for monitoring viral infection and cellular penetration of this second virus, and can be used to screen potential inhibitors of viral infection of this second virus, as illustrated in example 10, with a lentivirus pseudotyped with the SARS-CoV2 (covid-19) envelope protein.

The system also allows detecting and monitoring recombinant retrotranscribed viral DNA, as soon as the corresponding recombinant retrovirus entered a cell and is retrotranscribed, whether the retrotranscribed DNA is integrated into the cellular genome, or not, for example before integration, e.g. during its journey to nucleus. By pseudotyping the recombinant retrovirus with the envelope protein of any other virus, it is thus possible to detect and/or monitor viral entry of said pseudotyped retrovirus, mimicking the entry of said other virus.

Accordingly, in a first aspect this invention provides a recombinant lentiviral vector. In some embodiments the recombinant lentiviral vector comprises a coding sequence for an OR protein fused to a coding sequence for a fluorescent protein or a subunit of a fluorescent protein, and a promoter active in human cells operatively linked to the coding sequences. In some embodiments the coding sequence for the OR protein is fused to a coding sequence for green fluorescent protein (GFP). In some embodiments the promoter is the cytomegalovirus (CMV) promoter or EF1alfa promoter. In some embodiments the vector further comprises the coding sequence for MS2 coat protein (MCP) fused to a coding sequence for a fluorescent protein or a subunit of a fluorescent protein, and a promoter active in human cells operatively linked to the coding sequences. In some embodiments the vector comprises a 5'-LTR and a 3'-LTR. In some embodiments the vector comprises a central polypurine tract (cPPT)/central termination sequence (CTS), abbreviated as a cPPT/CTS sequence. In some embodiments the vector is an HIV-1 vector. In some embodiments the vector is LVCMV (or EF1a) OR-GFP. According to a preferred embodiment, the vector does not comprise any sequence corresponding to a binding site of the OR protein.

In another aspect recombinant retroviruses (members of the Retroviridae virus family) are provided. In some embodiments the recombinant retrovirus is selected from Human T-lymphotropic virus (HTLV), Bovine Leukemia virus (BLV) and Moloney virus (MLV). In a preferred embodiment the recombinant retrovirus is a lentivirus. In a further preferred embodiment, the recombinant lentivirus is an HIV virus such as an HIV-1 virus. In some embodiments the recombinant lentivirus comprises a recombinant genome comprising an RNA that generates an ANCH sequence upon retrotranscription. In some embodiments the ANCH sequence is an ANCH3 sequence. In some embodiments the recombinant genome is ΔEnv and ΔNef and in others only ΔEnv or WT HIV. In some embodiments the genome encodes an HA-tagged integrase protein ($IN_{HA}$). In some embodiments the lentivirus is HIV-1. In some embodiments the genome of the recombinant virus further comprises at least one MS2 binding site. In some embodiments the recombinant lentivirus is pseudotyped with a VSV-G envelope. In some embodiments the recombinant retrovirus is pseudotyped with a Spike(S) envelope from SARS-CoV-2 or other envelopes from other viruses.

According to a preferred embodiment, the recombinant lentivirus or retrovirus, potentially pseudotyped, does not comprise any sequence coding for an OR protein, either at the RNA level or after retro-transcription.

In another aspect recombinant eukaryotic cells are provided. In some embodiments the recombinant cells comprise a genomically integrated DNA copy of a recombinant lentiviral vector. In some embodiments the recombinant lentiviral vector comprises a coding sequence for an OR protein fused to a coding sequence for a fluorescent protein or a subunit of a fluorescent protein, and a promoter active in human cells operatively linked to the coding sequences. In some embodiments the coding sequence for the OR protein is fused to a coding sequence for green fluorescent protein (GFP). In some embodiments the promoter is the cytomegalovirus (CMV) promoter or EF1alfa promoter. In some embodiments the vector further comprises the coding sequence for MS2 coat protein (MCP) fused to a coding sequence for a fluorescent protein or a subunit of a fluorescent protein, and a promoter active in human cells operatively linked to the coding sequences. In some embodiments the vector comprises a 5'-LTR and a 3'-LTR. In some embodiments the vector comprises a cPPT/CTS sequence. In some embodiments the vector is an HIV-1 vector. In some embodiments the vector is LVCMV (or EF1a) OR-GFP.

In some embodiments the recombinant eukaryotic cells further comprise a recombinant genome of a recombinant retrovirus, such as a recombinant lentivirus. In some embodiment the recombinant lentivirus comprises a recombinant genome comprising an RNA that generates an ANCH sequence upon retrotranscription. In some embodiments ANCH sequence is an ANCH3 sequence. In some embodiments the recombinant genome is ΔEnv and ΔNef. In some embodiments the genome encodes an HA-tagged integrase protein ($IN_{HA}$). In some embodiments the lentivirus is HIV-1. In some embodiments the genome of the recombinant virus further comprises at least one MS2 binding site. In some embodiments the recombinant lentivirus is pseudotyped with a VSV-G envelope. In some embodiments the recombinant lentivirus or retrovirus is pseudotyped with a Spike(S) envelope from SARS-CoV2 or other envelopes from other viruses.

In some embodiments the recombinant eukaryotic cell is a human cell, such as a HeLa cell, a Jurkat cell, a ThP1 cell or primary cells, such as CD4+ T cells and/or macrophages.

According to another embodiment, the invention also encompasses a recombinant eukaryotic cell comprising a recombinant genome of a recombinant retrovirus, such as a recombinant lentivirus or retrovirus according to the invention.

In another aspect this invention provides methods of observing lentiviral DNA in a eukaryotic cell. In some embodiments the method comprises providing a recombinant eukaryotic cell that produces a fusion protein comprising an OR protein, fused to a fluorescent protein or a subunit of a fluorescent protein; infecting the recombinant eukaryotic cell with a recombinant retrovirus comprising a recombinant genome comprising an RNA that generates an ANCH sequence upon retrotranscription, under conditions sufficient for reverse transcription of the recombinant lentiviral genome comprising an ANCH sequence; allowing the OR protein to bind to the ANCH sequence; and detecting the fluorescent protein or subunit of the fluorescent protein to thereby observe the lentiviral DNA in the eukaryotic cell. In a preferred embodiment of the method a lentivirus is used, such as an HIV virus. Thus, in a preferred embodiment the method comprises providing a recombinant eukaryotic cell that produces a fusion protein comprising an OR protein, fused to a fluorescent protein or a subunit of a fluorescent protein; infecting the recombinant eukaryotic cell with a recombinant lentivirus comprising a recombinant genome comprising an RNA that generates an ANCH sequence upon retrotranscription, under conditions sufficient for reverse transcription of the recombinant lentiviral genome comprising an ANCH sequence; allowing the OR protein to bind to the ANCH sequence; and detecting the fluorescent protein or subunit of the fluorescent protein to thereby observe the lentiviral DNA in the eukaryotic cell. In some embodiments the method further comprises making the recombinant eukaryotic cell that produces a fusion protein comprising an OR protein, fused to a fluorescent protein or a subunit of a fluorescent protein, by a method comprising transducing a eukaryotic cell with a lentiviral vector comprising a coding sequence for the fusion protein comprising an OR protein, fused to a fluorescent protein or a subunit of a fluorescent protein, and a promoter active in human cells operatively linked to the coding sequences. In some embodiments the lentiviral DNA is observed in the cytoplasm of the eukaryotic cell. In some embodiments the lentiviral DNA is observed during nuclear translocation. In some embodiments the lentiviral DNA is observed in association with viral CA (capsid) and/or integrase (IN) or cellular factors important for viral replication, such as CPSF6. In some embodiments the lentiviral DNA is present in a pre-integration complex (PIC). In some embodiments the lentiviral DNA is observed in the nucleus. In some embodiments the lentiviral DNA is observed integrated into the host cell genome. In some embodiments the lentiviral DNA is observed with single molecule resolution.

In some embodiments the OR protein is fused to green fluorescent protein (GFP). In some embodiments the promoter is the cytomegalovirus (CMV) or EF1a promoter. In some embodiments the fusion protein further comprises an MS2 coat protein (MCP). In some embodiments the vector comprises a 5'-LTR and a 3'-LTR. In some embodiments the vector comprises a cPPT/CTS sequence. In some embodiments the vector is an HIV-1 vector. In some embodiments the vector is LVCMVOR-GFP. In some embodiments the ANCH sequence is an ANCH3 sequence. In some embodiments the recombinant genome is ΔEnv and ΔNef. In some embodiments the recombinant genome encodes an HA-tagged integrase protein (IN$_{HA}$). In some embodiments the lentivirus is HIV-1. In some embodiments the genome of the virus further comprises at least one MS2 binding site. In some embodiments the recombinant lentivirus is pseudo-typed with a VSV-G envelope. In some embodiments the recombinant lentivirus or retrovirus is pseudotyped with a Spike(S) envelope from SARS-CoV2 or other envelopes from other viruses, not necessarily lentiviruses.

In another aspect the invention provides a method of characterizing an agent that interferes with lentiviral nuclear translocation and/or integration thus enhancing or down-regulating translocation and/or integration, including factors increasing or decreasing entry, reverse transcription and/or integration, comprising performing a method of observing lentiviral DNA in a eukaryotic cell of the invention in the presence of an agent and determining whether the agent interferes with lentiviral nuclear translocation and/or integration. In some embodiments the method further comprises performing the method of observing lentiviral DNA in a eukaryotic cell in the absence of the agent; wherein determining whether the agent interferes with lentiviral nuclear translocation and/or integration comprises comparing lentiviral nuclear translocation and/or integration in the presence of the agent with lentiviral nuclear translocation and/or integration in the absence of the agent. In some embodiments the agent interferes with lentiviral nuclear transloca-tion. In some embodiments the agent does not interfere with lentiviral nuclear translocation. In some embodiments the agent interferes with lentiviral integration. In some embodiments the agent does not interfere with lentiviral integration or episomal forms. In some embodiments the agent does not interfere with lentiviral transcription and replication.

In another aspect the invention provides a method of screening an agent that interferes with viral penetration or viral nuclear translocation of a given second virus, thus enhancing or downregulating penetration including factors increasing or decreasing entry of this second virus, com-prising performing a method of observing lentiviral DNA in a eukaryotic cell of the invention in the presence of an agent and determining whether the agent interferes with lentiviral nuclear translocation and/or integration, wherein said lenti-viral DNA is the retrotranscribed DNA of a recombinant lentivirus of the invention, pseudotyped with the envelope protein of said second virus.

Data is representative of two or more independent experiments. d) Primary CD4+ T cells derived from healthy patients were isolated, activated and tranduced with LV OR-GFP, later cells were infected with HIV-1 ANCH3. Live imaging using Biostation has been applied to follow nuclear green spots (vDNA).

Figure 3:
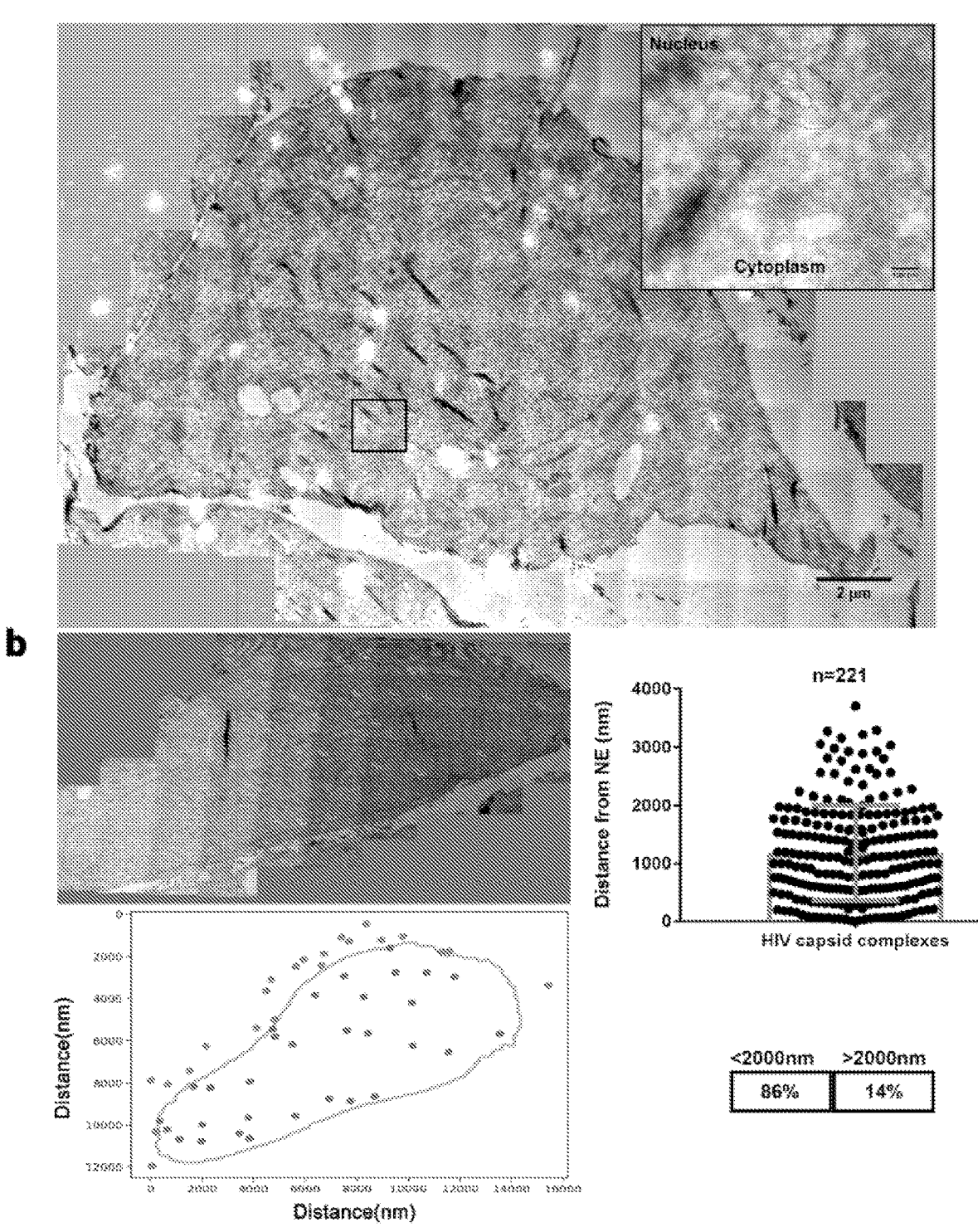
Figure 3:
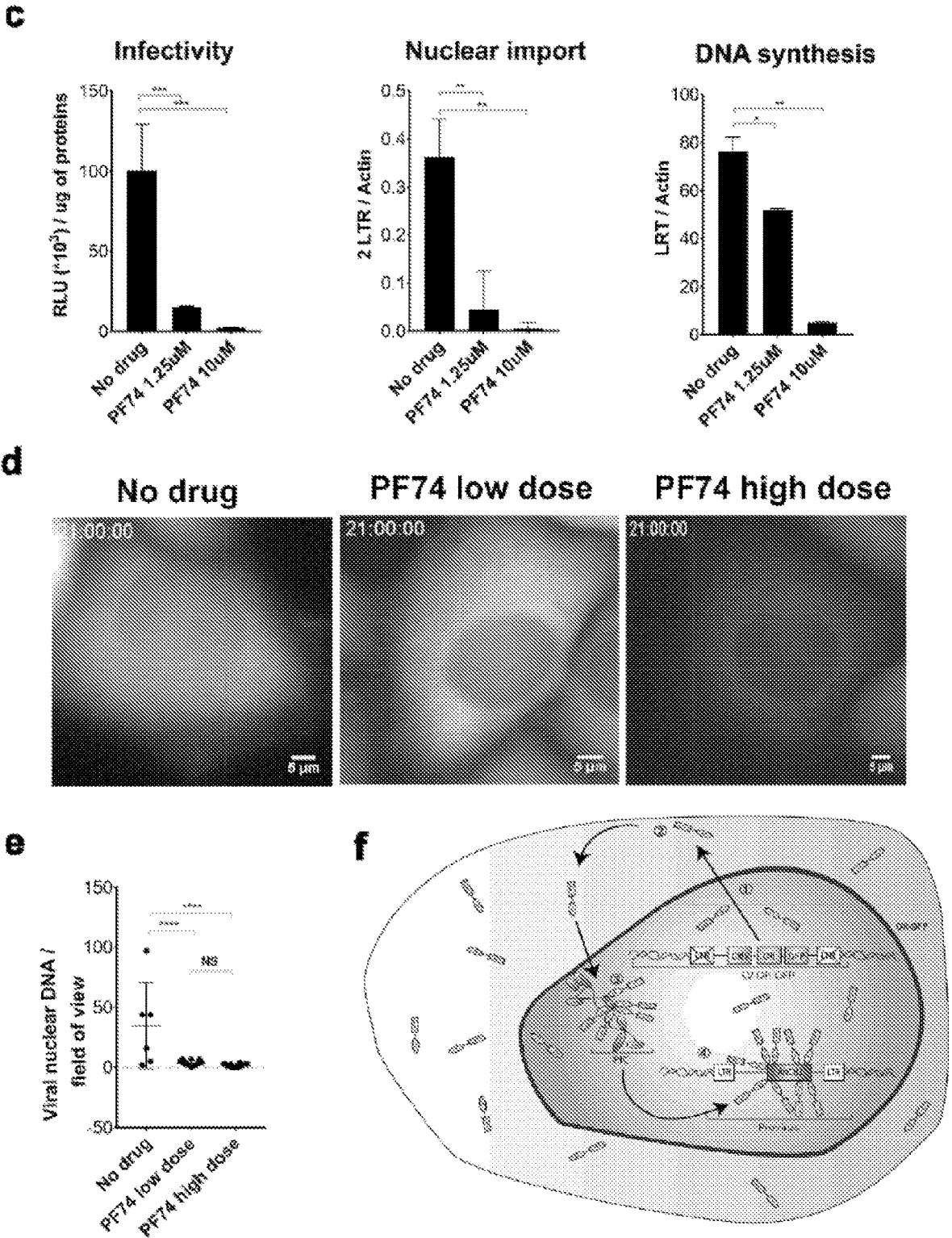

FIG. 3: Visualization of the functional HIV-1 PIC entering in the host nucleus. a) Overlap of the high resolution correlation between TEM and fluorescence images and viral DNA association to CA proteins at the NE by CLEM. The yellow signals correspond to Tetraspecks beads used as fiducials emitting in the green and far-red channels, the green signals are the viral detections. The magnified image shows the green DNA signal near the three dots of 10 nm gold anti-CA antibody, the dashed line depicts the 73 nm radius error in the correlation of the viral DNA with the TEM picture. b) Analysis of the distribution of PIC complexes in TEM detected using antibodies against CA, IN and ORGFP at 6 h post infection. Nuclear envelope of 10 cells was manually outlined in FIJI and the closest distance of gold complexes (yellow circumferences) to the NE calculated with a custom Python script. Red dots represent gold complexes detected outside of the nucleus whereas green inside the nucleus. The mean distance of the gold complexes to the NE of 221 complexes is shown as well as the percentage of complexes closer or further than 2000 nm to the NE c) HeLa cells infected with HIV-1ΔEnvIN$_{HA}$ΔNef ANCH3/VSV-G in presence or not of PF74 (low dose, 1.25 μM; high dose 10 μM) Infectivity was analyzed at 48 h post infection by beta galactosidase assay and normalized by protein amount; nuclear import and DNA synthesis were analyzed by qPCR of 2LTRs or LRT respectively normalized by actin. Statistical analysis has been calculated by Graph Pad Prism 7 using two-tailed Student's t test. Differences were considered statistically significant at a P value of <0.001 (*), or <0.01 () or <0.1 (*). d) Same cells were imaged in live by Biostation for more than 24 h. e) Individual spots inside of the nuclei were manually counted and statistically analyzed by Graph Pad Prism 7 (cells analyzed for each condition: no drugs 52 cells, PF74 low dose 113 cells, PF74 high dose 100 cells), results were analyzed using two-tailed Student's t test, P value<0.0001 (****) and nonsignificant (ns). Data is representative of two or more independent experiments. f) The applied technology for live imaging of viral DNA begins with 1) the expression of OR-GFP fusion protein by LV ORGFP 2) OR-GFP is translated in the cytoplasm and diffuses in the whole cell volume with a main location in the cytoplasm due to the lack of the nuclear localization sequence (NLS) 3) binding of OR-GFP to ANCH3 sequence contained in the incoming PICs 4) or in the integrated provirus.

Figure 4:
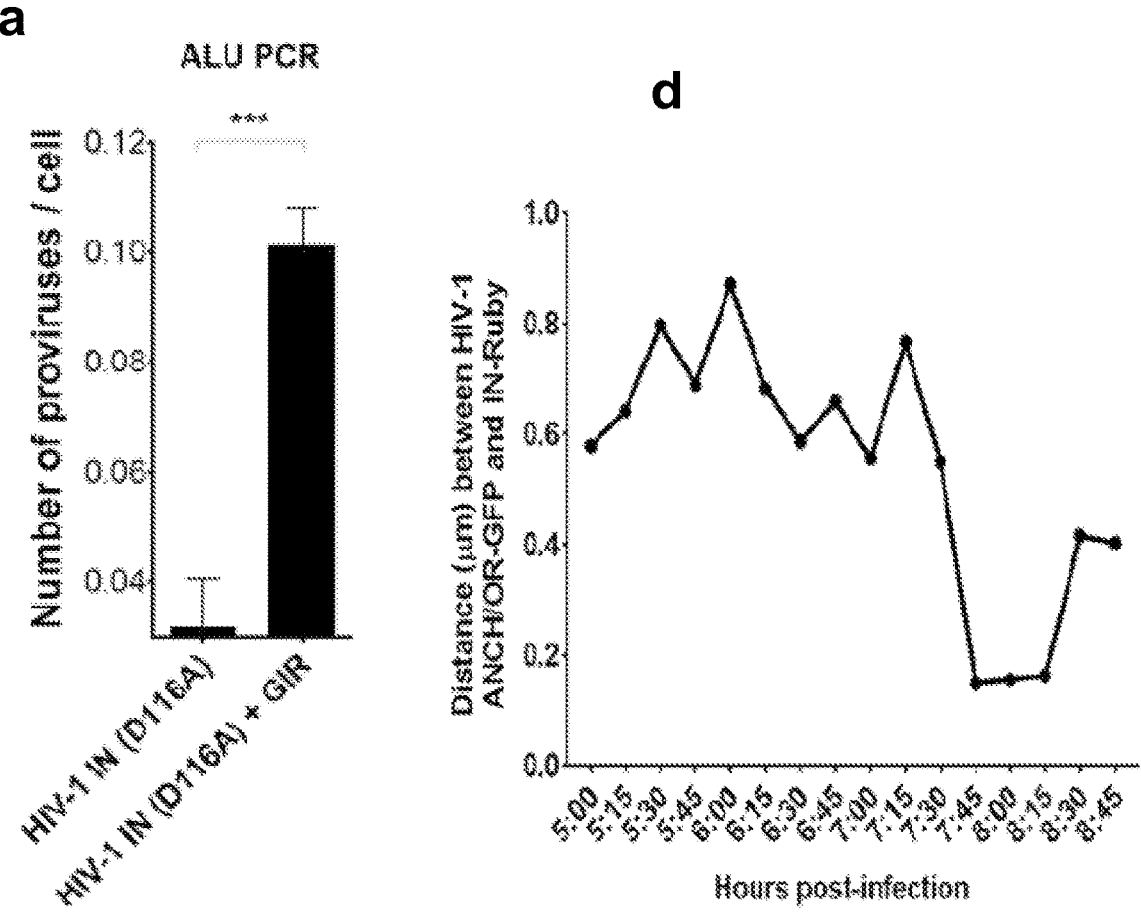
Figure 4:
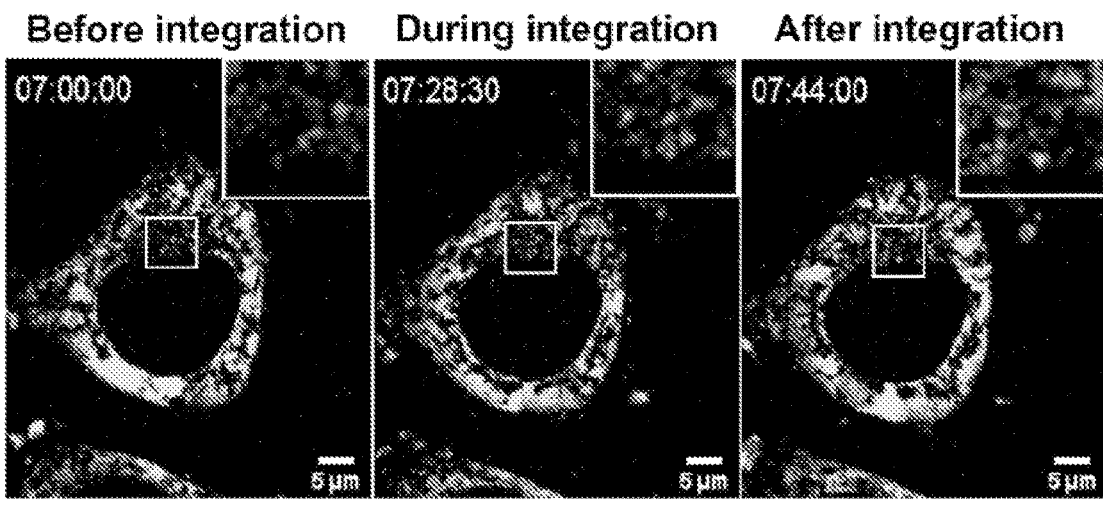
Figure 4:
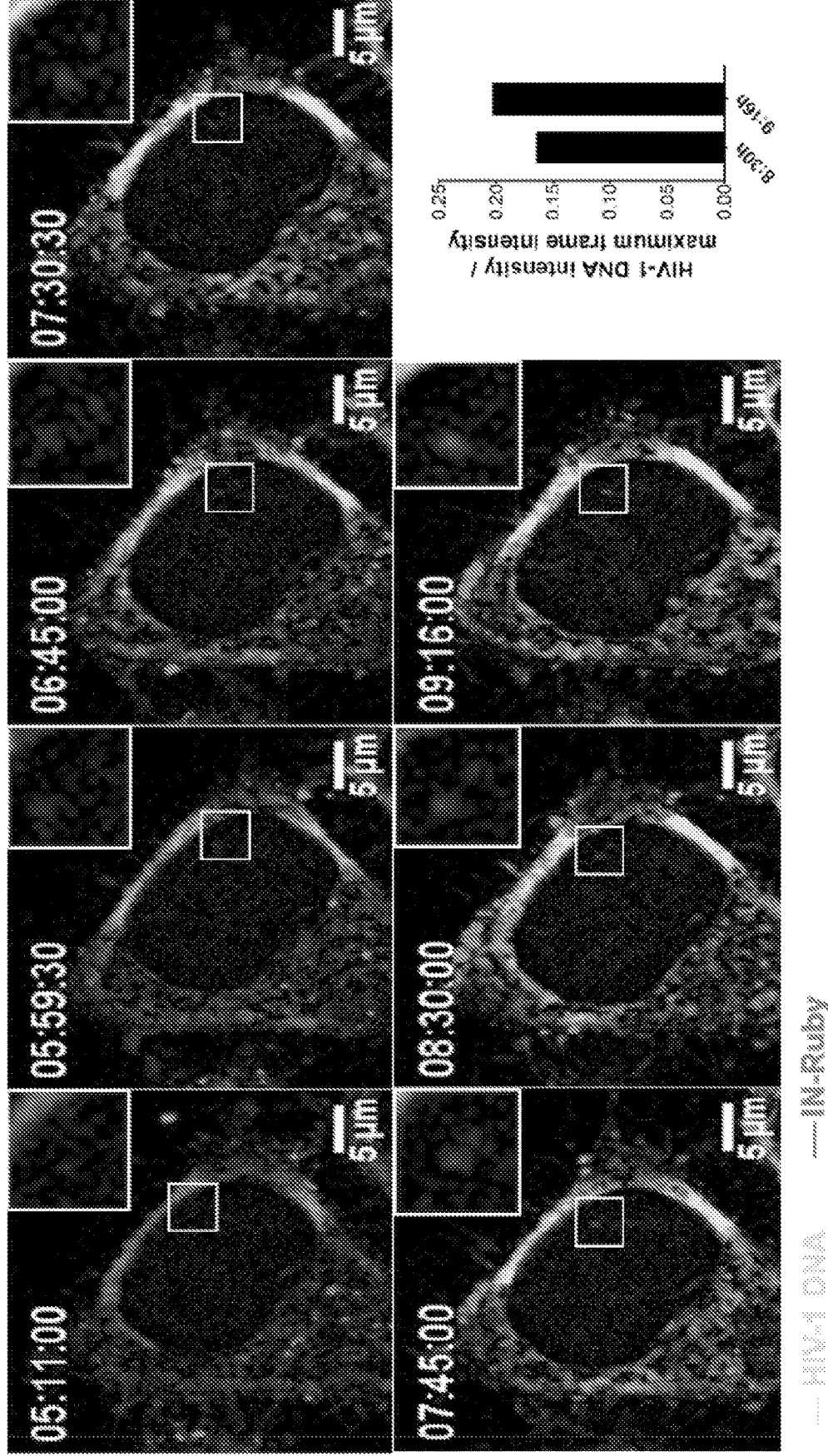

FIG. 4: Live imaging of HIV-1 integration step. a) HeLa cells stably expressing OR-GFP infected with HIV-1ΔEnv IN (D116A) ΔNef ANCH3/VSVG complemented or not with GIR plasmid (expressing the IN-Ruby) were analyzed for the number of viral integration per cell by Alu PCR at 24 h p.i. b) Time lapse images recorded using spinning disk microscope on infected HeLaP4R5 cells. HIV-1 DNA is visualized in the green channel by OR-GFP and the IN-Ruby using the red channel. c) Time lapse images extracted by the movie S4B recorded using spinning disk microscope. Ratio HIV-1 DNA intensity/maximum frame intensity at 8:30 and 9:16 hours post infection. Profile of distances between IN-Ruby and HIV-1 DNA OR-GFP during time post-infection are analyzed by ImageJ and plotted in the graphic by Graph Pad Prism 7. The time post-infection is shown in each time lapse image. This is a representative experiments of three biological replicates.

Figure 5:
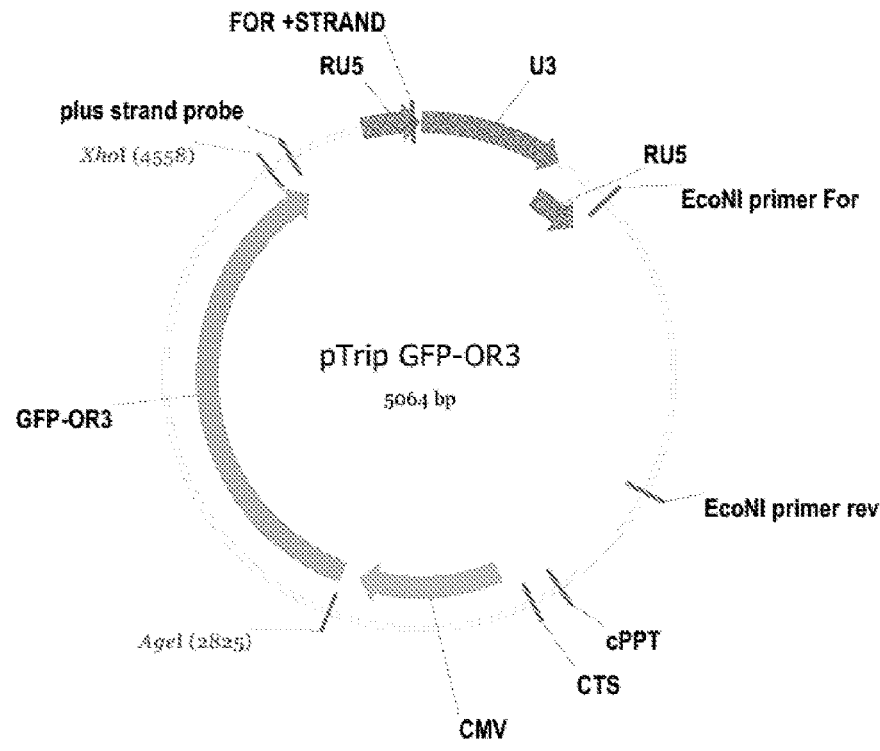

FIG. 5. Map of the LVCMVOR-GFP vector.

Figure 6:
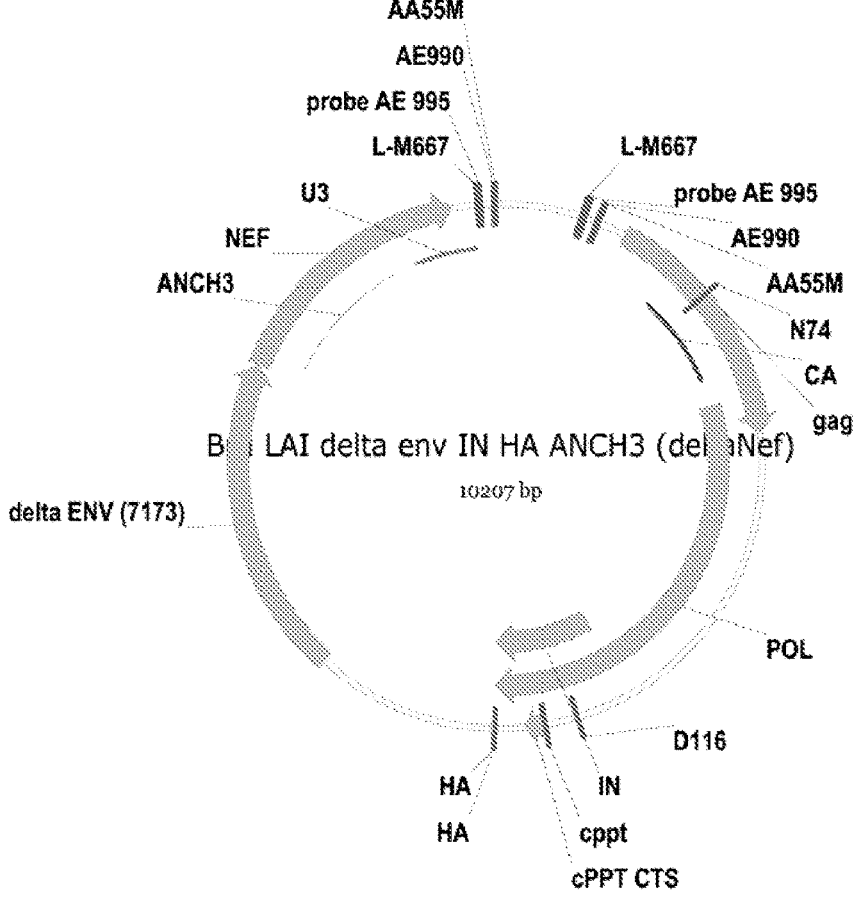

FIG. 6. Map of the recombinant lentivirus Bru LAI delta env IN HA ANCH3 (deltaNef).

Figure 7:
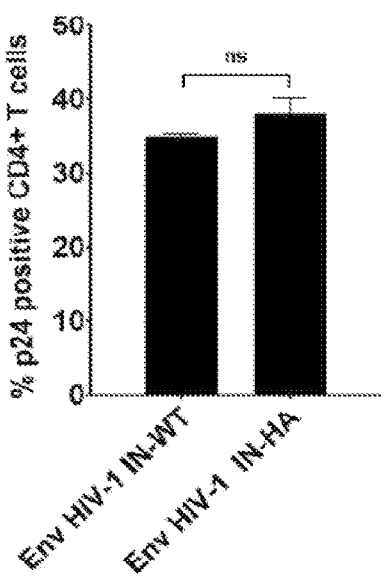
Figure 7:
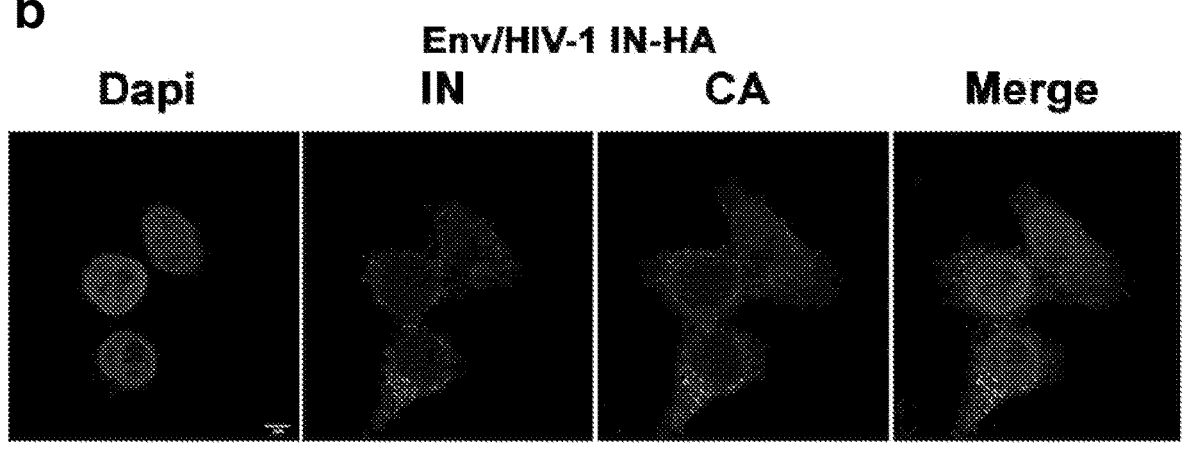
Figure 7:
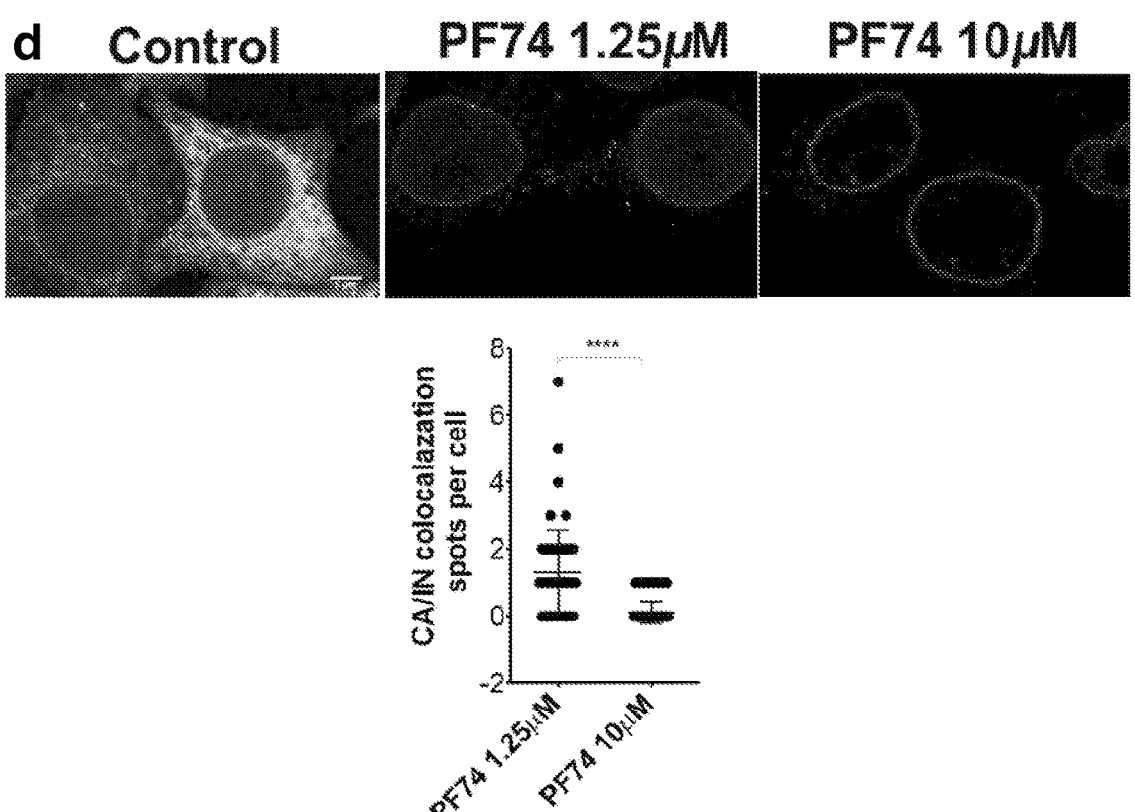
Figure 7:
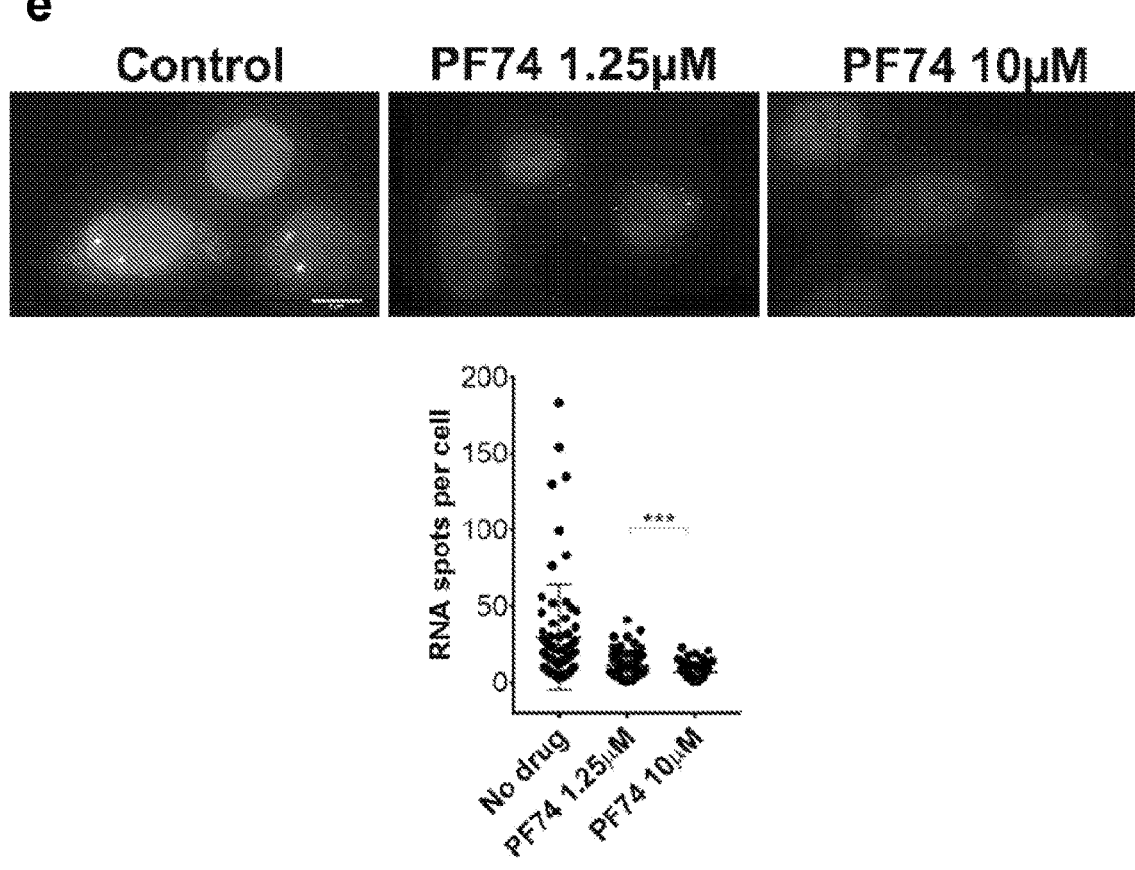

FIG. 7: Early steps of infection of a WT Env virus and the effect of PF74 compound on WT Env or VSV-G pseudo-typed HIV-1. a) Comparison of the infectivity in primary CD4+ T cells between wild type enveloped viruses carrying on the IN wild type or the IN fused to HA tag for the % of positive p24 cells analyzed by cytofluorimetry. b) HeLa P4R5 infected with HIV-1 IN$_{HA}$ ENV WT in presence of SEVI (Yolamanova et al., Nat. Nanotech. 2013, Kirchhoff Cell 2007) and fixed at 6 h post infection IN$_{HA}$ is shown in red (primary Ab anti HA and secondary Ab conjugated to Alexa 488), CA in green (primary Ab anti CA-NIH183 and secondary Ab conjugated to Alexa 647) and DNA in blue (Hoescht) by confocal microscopy. c) HeLa P4R5 infected with HIV-1 IN$_{HA}$ ENV WT with SEVI in presence or not of PF74. Infectivity was analyzed by b-galactosidase assay (left) and immunofluorescence using Ab against HA and CA (right). d) Hela cells infected for 24 h in presence or not of the drug PF74 at low dose (1.25 μM) or high dose (10 μM). Cells were fixed on 4% of PFA and labelled with antibodies anti p24, anti-HA and anti-Nup153. Co-localization between CA and IN was analyzed by ImageJ. e) RNA FISH has been performed using 24 probes against the viral Pol gene (Table 1). RNA molecules were detected automatically with FISH-quant in 3D[2]. Identical detection settings were used for all experimental conditions.

Figure 1:
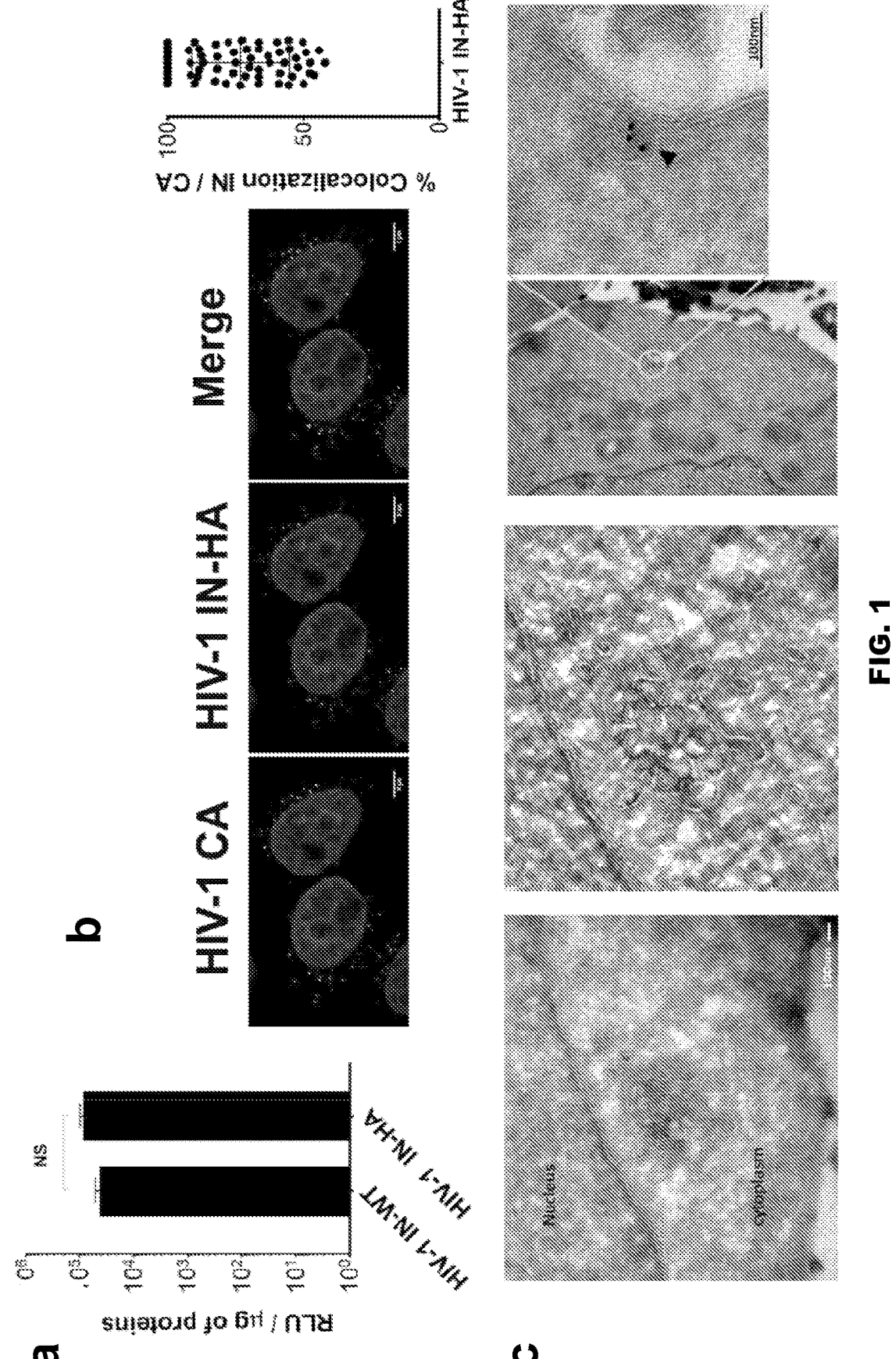
FIG. 1: Architecture of viral replication complexes during HIV-1 journey in the cytoplasm and in the nucleus. a) Comparison of the infectivity of HIV-1 carrying the IN wild type or the IN fused to HA tag analyzed by beta-galactosi-dase assay, normalized by amount of proteins. b) HeLa cells (10$^6$ cells) infected with 500 ng of p24 of HIV-1ΔEnv INHA/VSV-G fixed at 6 h.p.i. and labeled with antibodies anti p24 (NIH-183) and anti-HA. Analysis of the percentage of IN/CA co-localization analyzed by Image J and estimated by Graph Pad Prism 7. c) Images of VSV-G HIV-1 capsid cores escaping from the endosomes. First from the left a 2d plane extracted from the tomogram of the endosomes con-taining viral particles, the volume reconstructed has been colored in red for the envelope, blue for the cores, yellow for the borders of the endosome and green for the nuclear membrane. The pictures on the right show a capsid core escaping from the endosome and decorated with three gold 10 nm particles revealing the antibodies anti-capsid attached. d) Examples of core like structures docked at the NPC. The decoration of gold particles demonstrated the presence of HIV-1 CA proteins in these structures. For comparison a negative control is also shown on the left e) Remodeling of CA complexes at 6 hours post infection. Cryo-electron and immunogold labelling have been used. The image contains several CA complexes (pointed out by black arrows) each one with multiple CA proteins showed by gold particles. The magnified views of the areas enclosed by black rectangles display the differences in the gold distribution between outside and inside the nucleus. Images where obtained using an antibody against HIV-1 CA coupled to 10 nm gold f) Tomograms of HIV-1 CA structures during nuclear entry on cryosections of 75 nm labelled with anti-CA antibody coupled to 10 nm gold particles and refreeze with Leica Plunge-freezer as in e. Sections were imaged in a T12 FEI electron microscope with tomography capabili-ties. The tomogram volume was reconstructed and manually segmented using IMOD. The area corresponds to a high magnification map of FIG. 1e. The upper panels starting from the left contains several planes (number 31, 43 and 49 out of 91 total slices) and the segmentation obtained from the reconstructed tomographic volume containing the gold labelled CA complexes, NE, ER and mitochondria (yellow, green, magenta and purple respectively). On the bottom is depicted the magnified views of the areas delimited by dashed lines on the upper panels. g) The CA complexes detected at 6 h.p.i. inside the nucleus frequently contains IN. The double labelling gold labelling of CA (10 nm) and IN (6 nm) highlights the association of both proteins inside the nucleus of Hela cells. h) Percentage of complexes containing 2 or 3 CA gold particles in the cytoplasm and in nucleus, ~39 viral complexes were analyzed.
Figure 1:
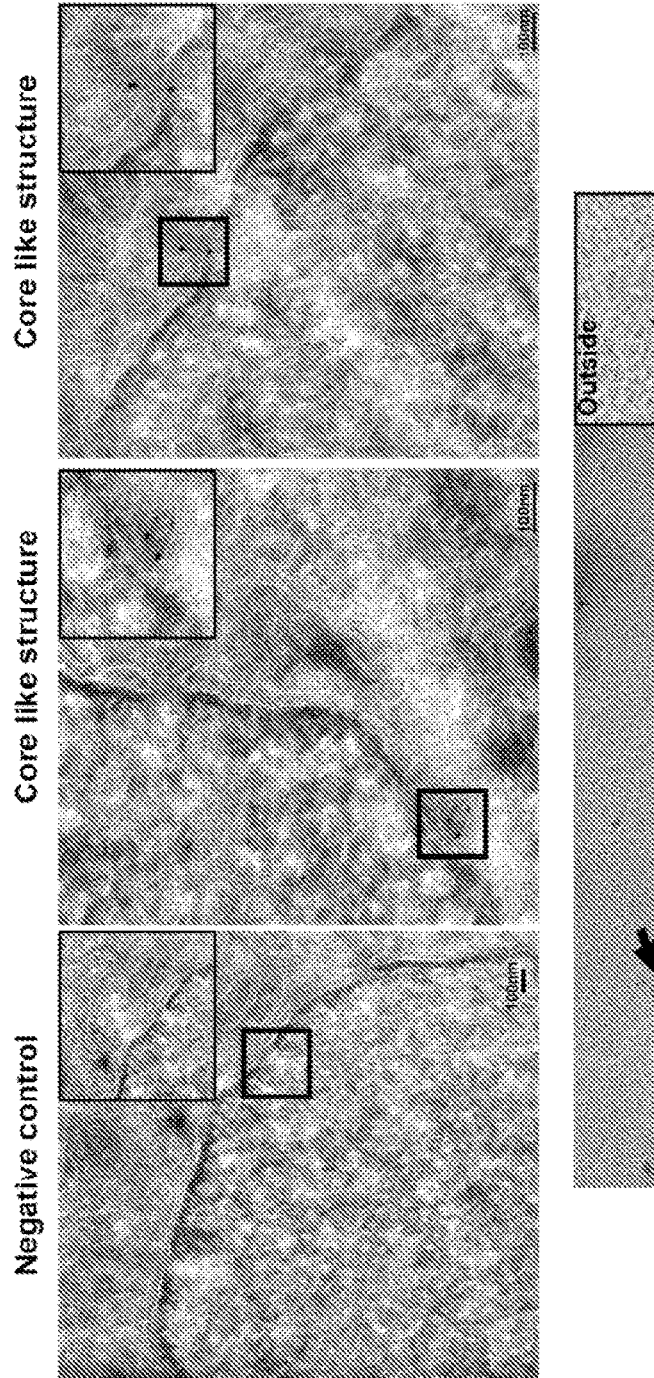
Figure 1:
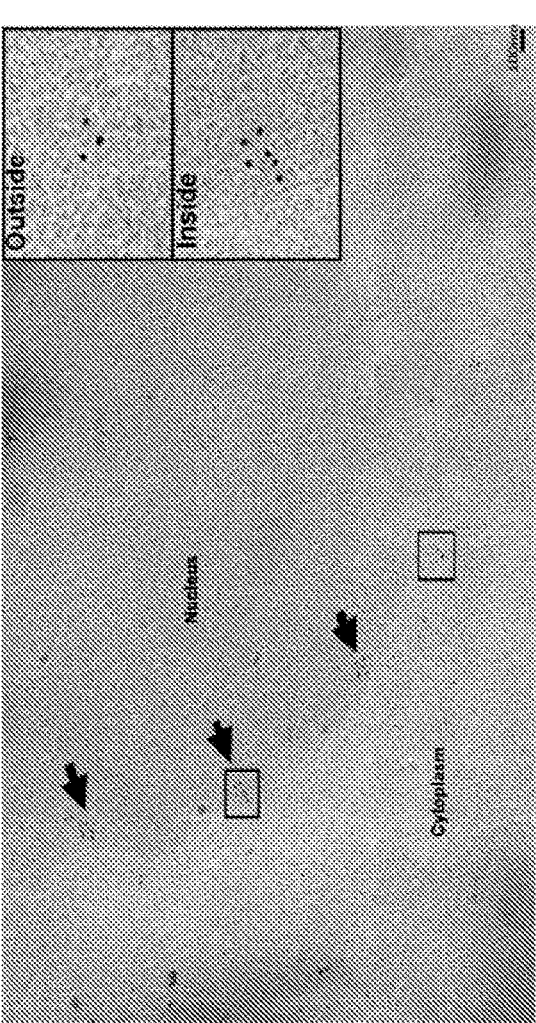
Figure 1:
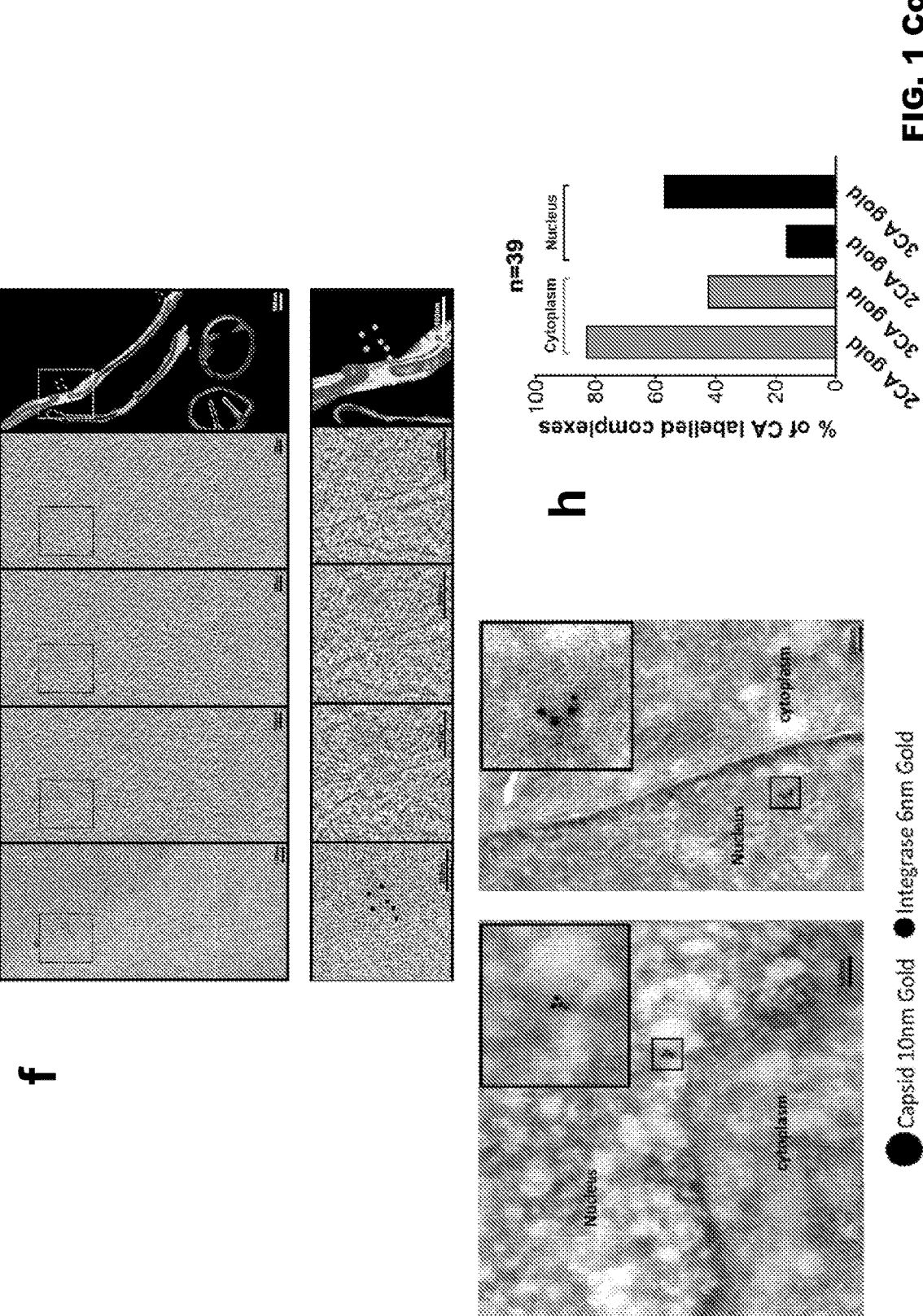
Figure 8:
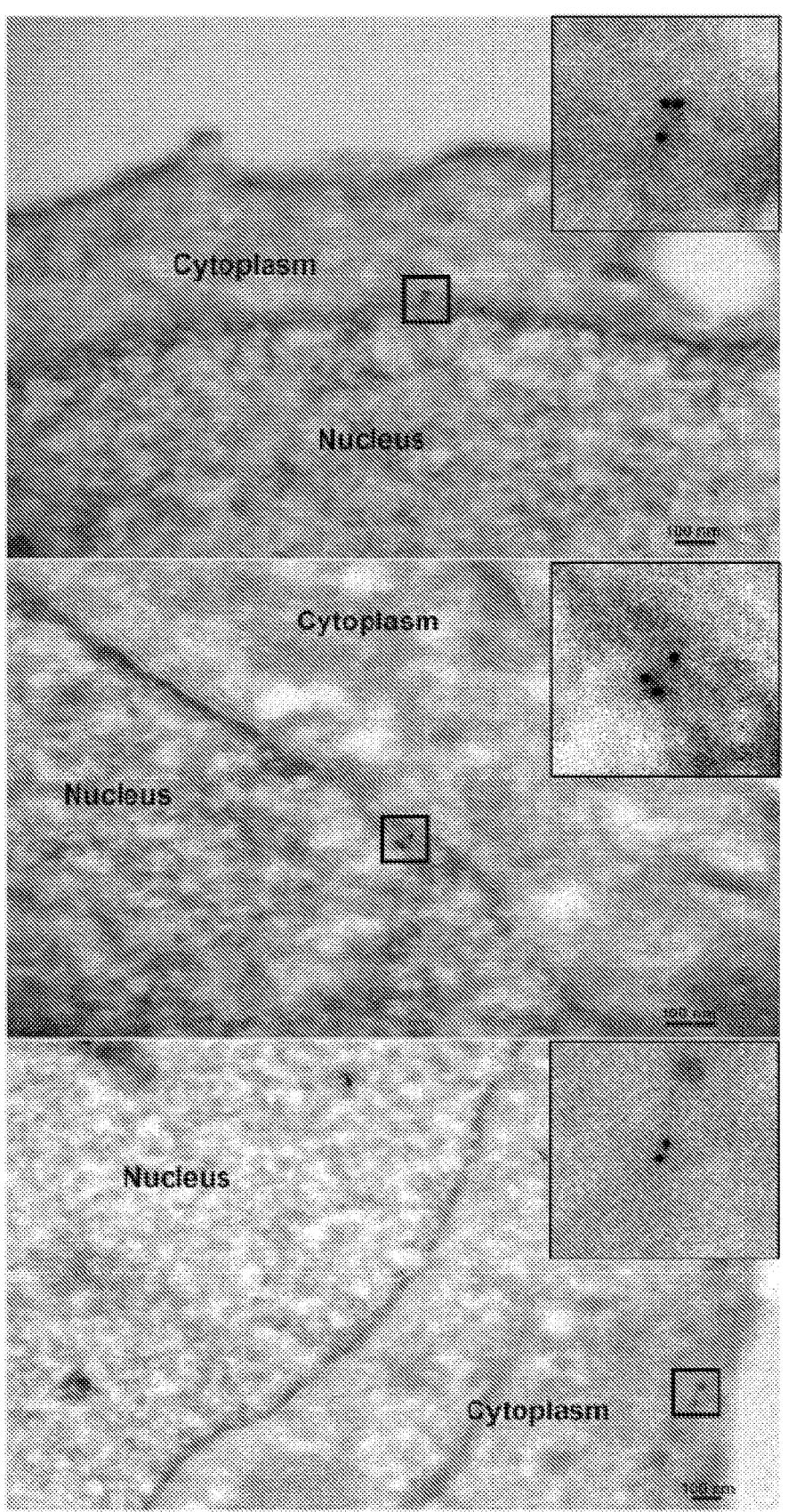

FIG. 8. HeLaP4R5 cells infected with HIV-1 IN$_{HA}$ ENV WT. The sections were prepared and immunolabelled as in FIG. 1$d$. The areas containing the viral CA complexes are enlarged in squares on the upper left of the pictures.

Figure 9:
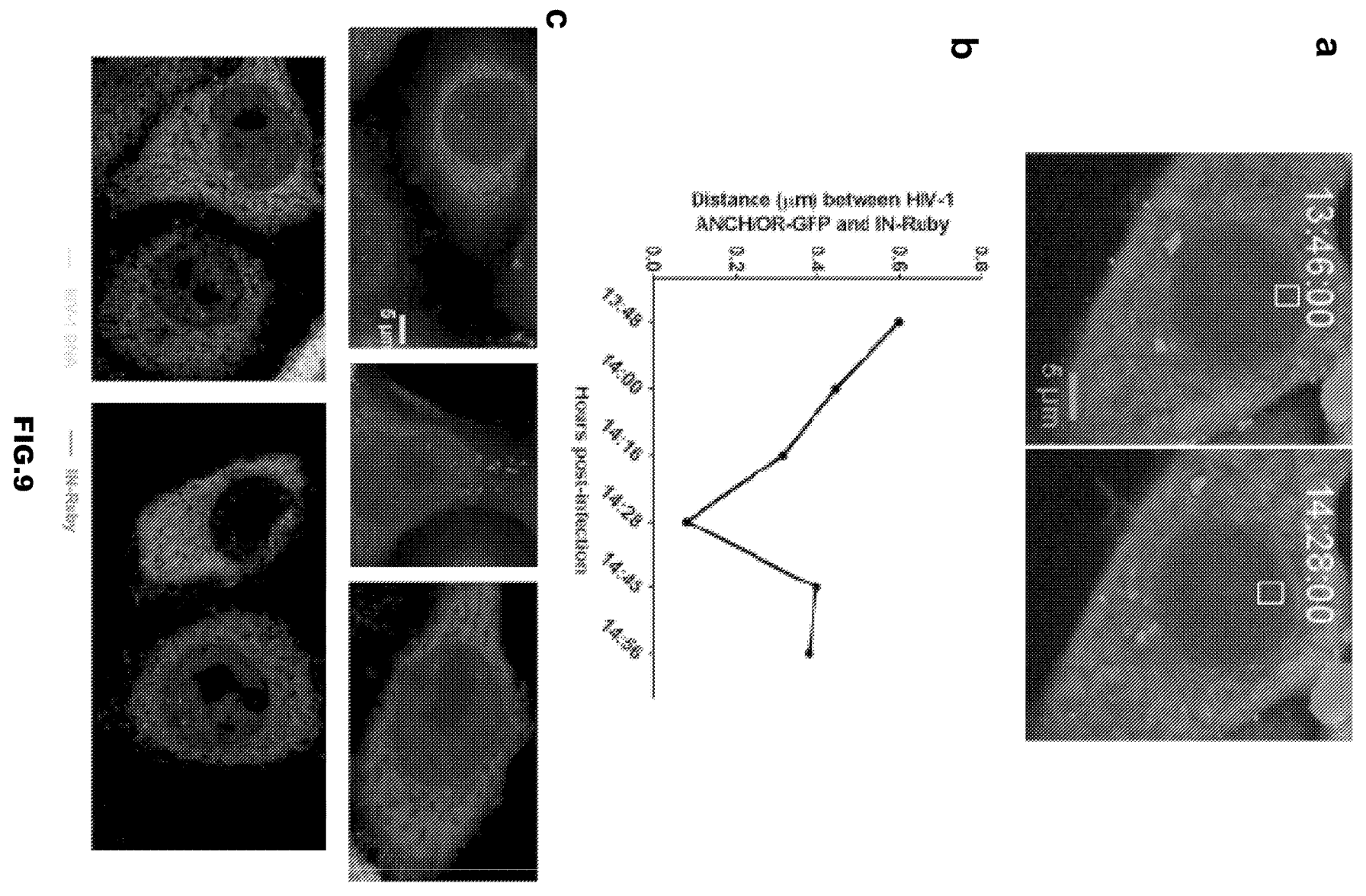

FIG. 9. a) HeLaP4R5 cells stably expressing ORGFP infected with HIV-1ΔEnv IN (D116A) complemented with GIR. Dynamic of interplay between viral IN-Ruby and HIV-1 DNA bound to OR-GFP proteins during different time post infection (spinning disk). b) The profile of distances between IN-Ruby and HIV-1 DNA OR-GFP during time post-infection are analyzed by ImageJ and plotted in the graphic by Graph Pad Prism 7. The time post-infection is shown in each time lapse image. c) Fluorescence confocal images of HeLaP4R5 cells stably expressing OR-GFP and infected with HIV-1ΔEnv IN (D116A) complemented with GIR at 24 h p.i.

Figure 10:
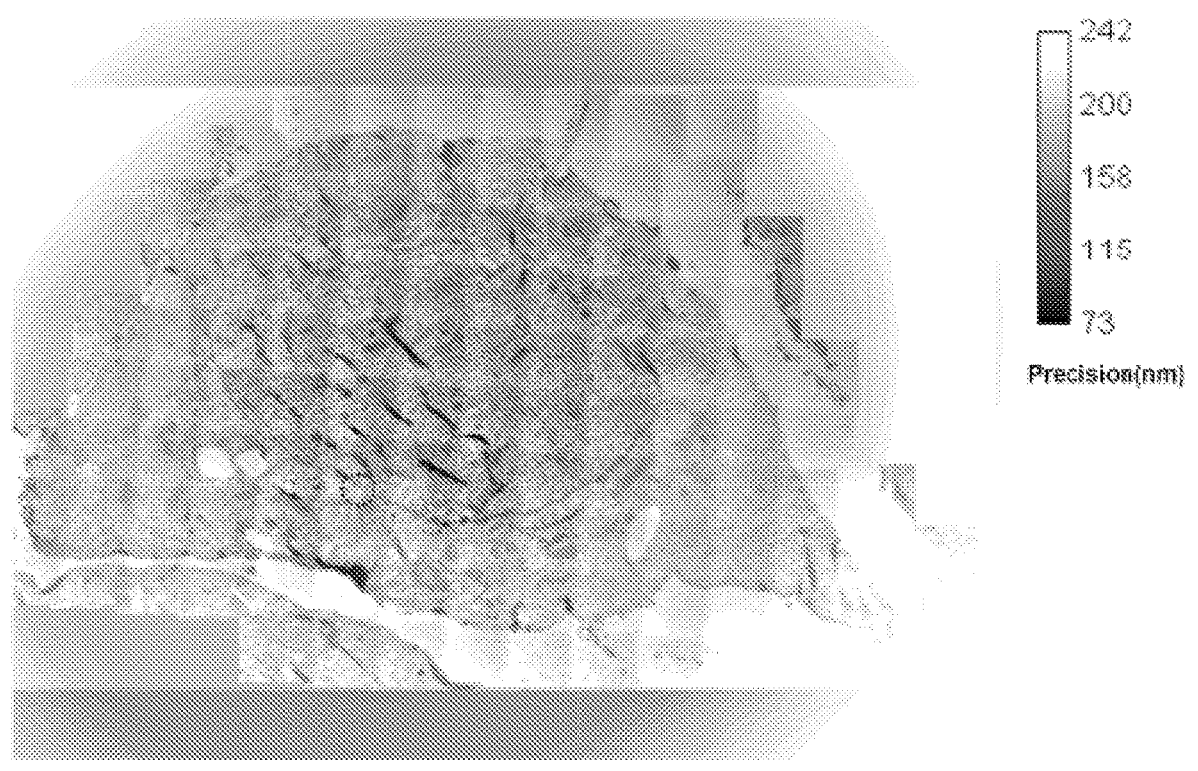

FIG. 10. a) The precision of the correlation between TEM and fluorescence images were estimated with ec-CLEM plugin under the icy environment. The calibration bar represents the precision achieved in nm by the different area of the cells. The dashed circle shows the area enlarged in the black box of FIG. 3$a$.

Figure 11:
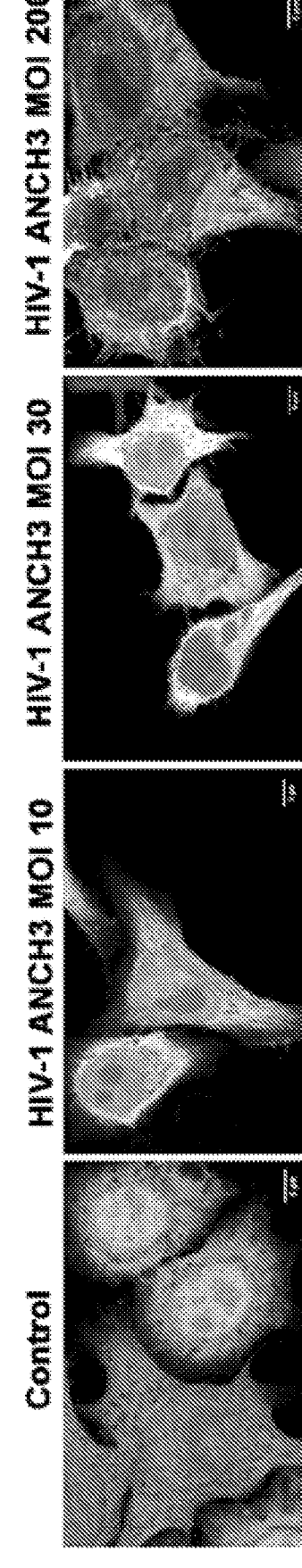
Figure 11:
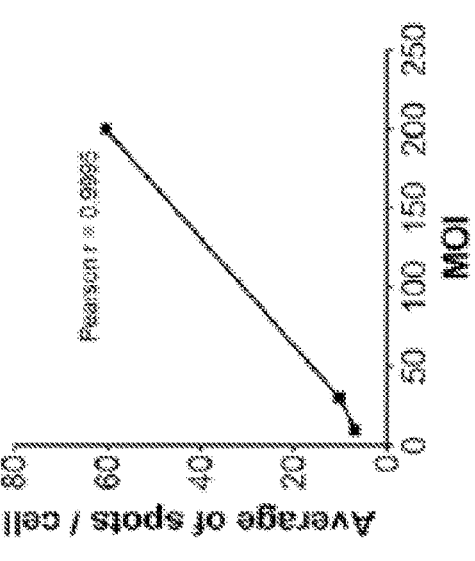
Figure 11:
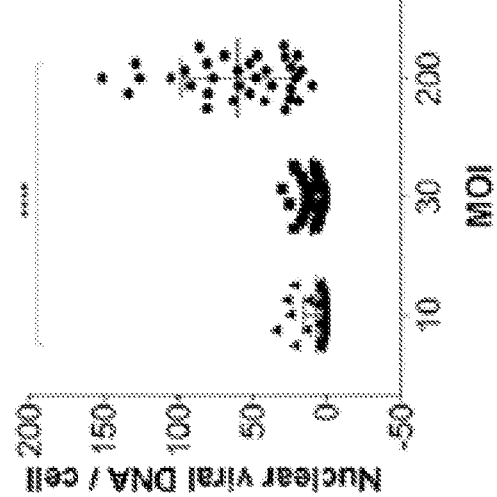

FIG. 11. Validation of the specificity of HIV-1 ANCHOR system to visualize the viral DNA. a) HeLaP4R5 cells stably transduced with LVOR-GFP were infected at different MOIs of HIV-1 ANCH3 and imaged after 24 h by confocal microscopy. Nuclear viral DNA spots per single GFP+ cell were analysed in 2D by ImageJ. Correlation analysis and the Pearson's coefficient as well as statistical analysis have been performed by Graph Pad Prism 7 (Anova test). b) HeLaP4R5 cells infected at MOI 50 with HIV-1ΔEnvIN$_{HA}$ΔNef ANCH3/VSV-G in presence or not of PF74 (low dose, 1.25 μM; high dose 10 μM). Cells were imaged by confocal microscope at 24 h post-infection. c) Individual spots inside the nuclei were manually counted and statistically analysed in 2D by Graph Pad Prism 7, statistics were calculated using two-tailed Student's t test. P value<0.0001 (**) and nonsignificant (ns). d) Viral nuclear import has been evaluated by qPCR (2LTRs) and normalized by actin. Statistical analysis has been calculated by Graph Pad Prism 7 using two-tailed Student's t test. Differences were considered statistically significant at a P value of <0.001 (*). or <0.01 (**). e) Confocal micros-copy of intranuclear spots detections in HeLa P4R5 OR-GFP challenged with MOI30 of HIV-1 ANCH3 in presence or not of NEV at 24 h post-infection. 2D statistical analysis of a manual count of intranuclear spots has been performed by Graph Pad Prism 7. All data are representative of two or more independent experiments.

Figure 12:
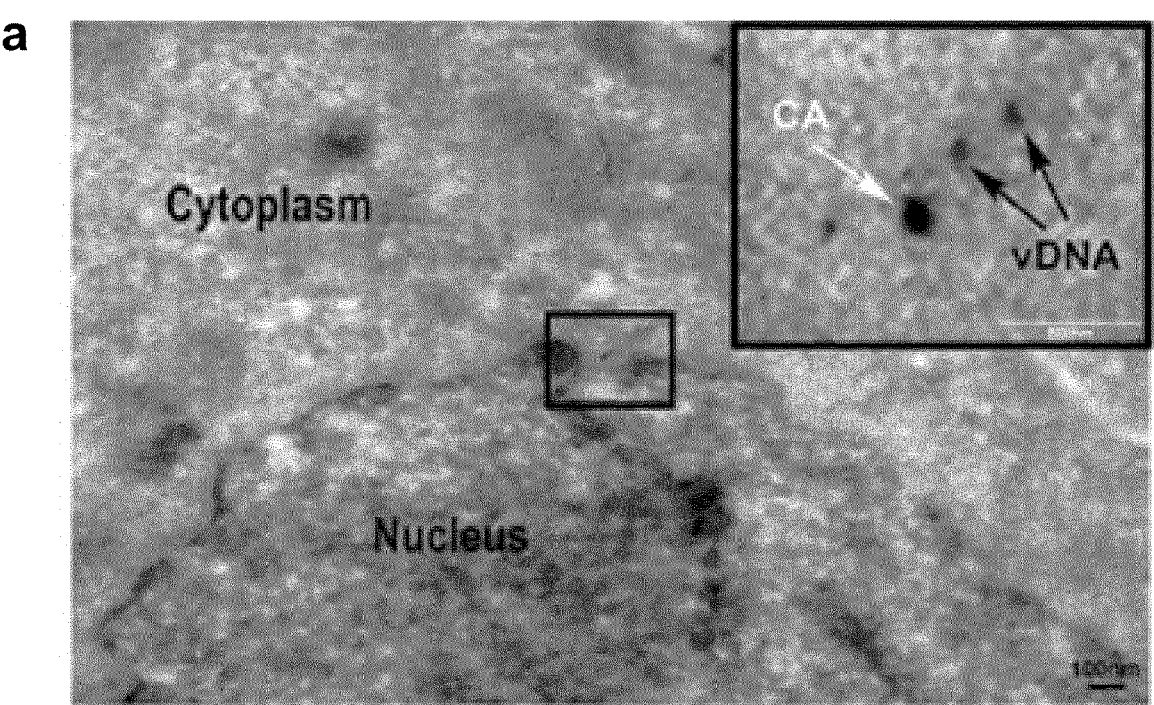
Figure 12:
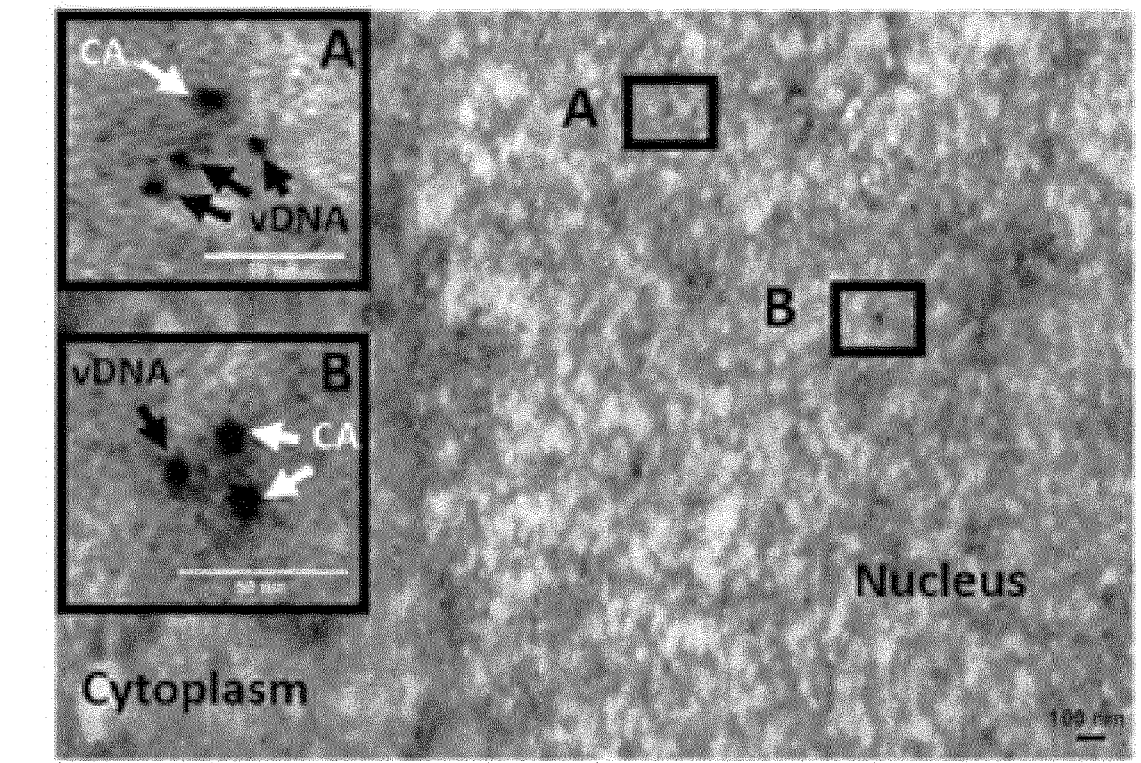

FIG. 12. HIV-1 ANCHOR allows the identification of HIV-1 PIC in the nucleus of infected cells using immuno-gold labeling coupled to EM. a) Double gold labelling coupled to TEM show CA/OR-GFP (viral DNA) as part of the same complex near the NE. Viral DNA is detected by the presence of clusters formed by multiple OR-GFP bound to ANCH3 sequence cloned in HIV-1 genome. OR-GFP pro-teins are labelled by the same primary antibody against GFP used in CLEM and a secondary antibody conjugated with gold particles of 5 nm. HIV-1 CA is revealed by a primary antibody against CA (NIH183-H12-5C) and a secondary antibody conjugated with gold (10 nm). Scale bars 100 nm. b) Intranuclear viral complexes contain CA and viral DNA detected by double gold labelling coupled to TEM. Scale bar 100 nm.

Figure 13:
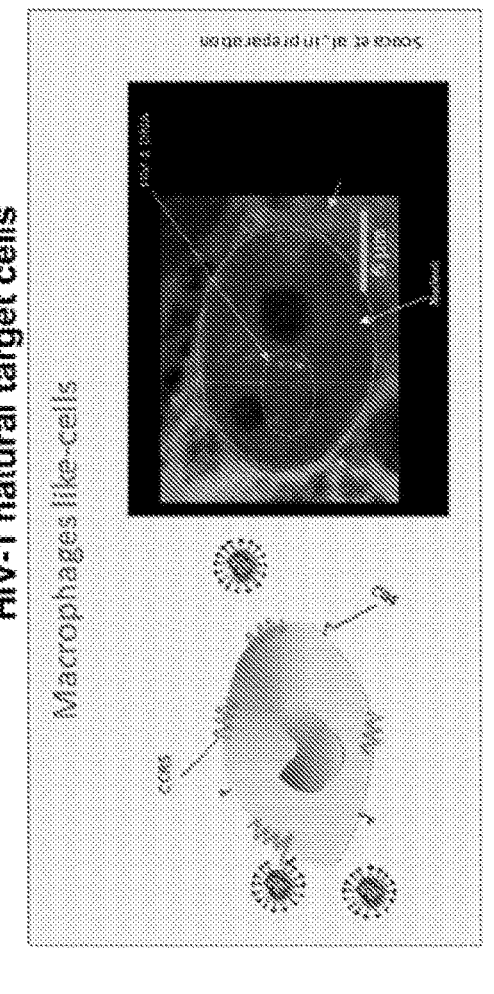
Figure 13:
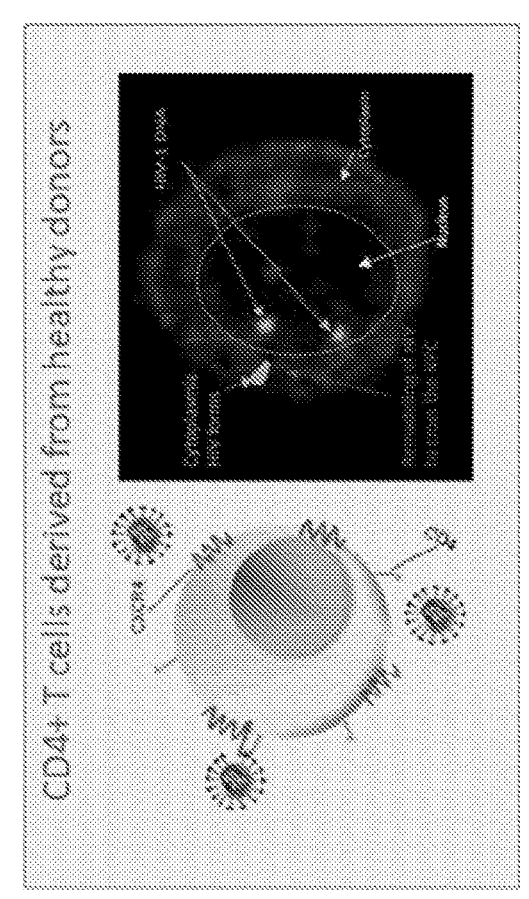
Figure 13:
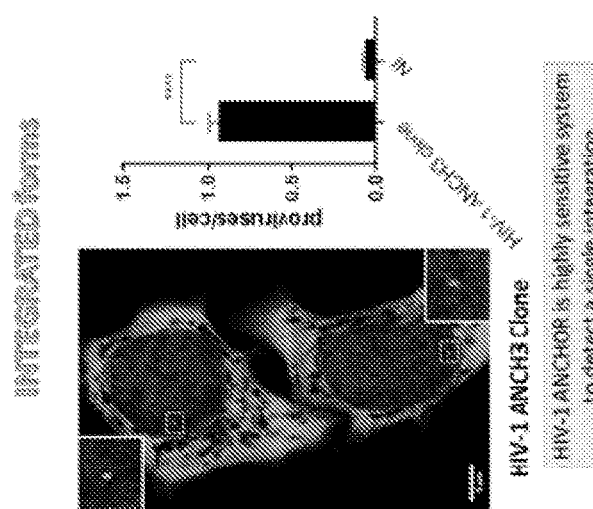
Figure 13:
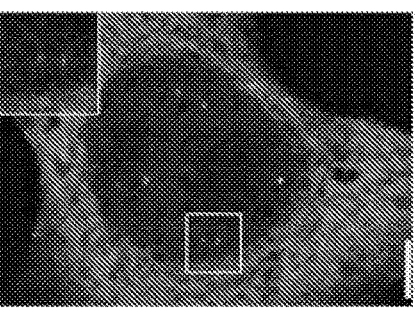
Figure 13:
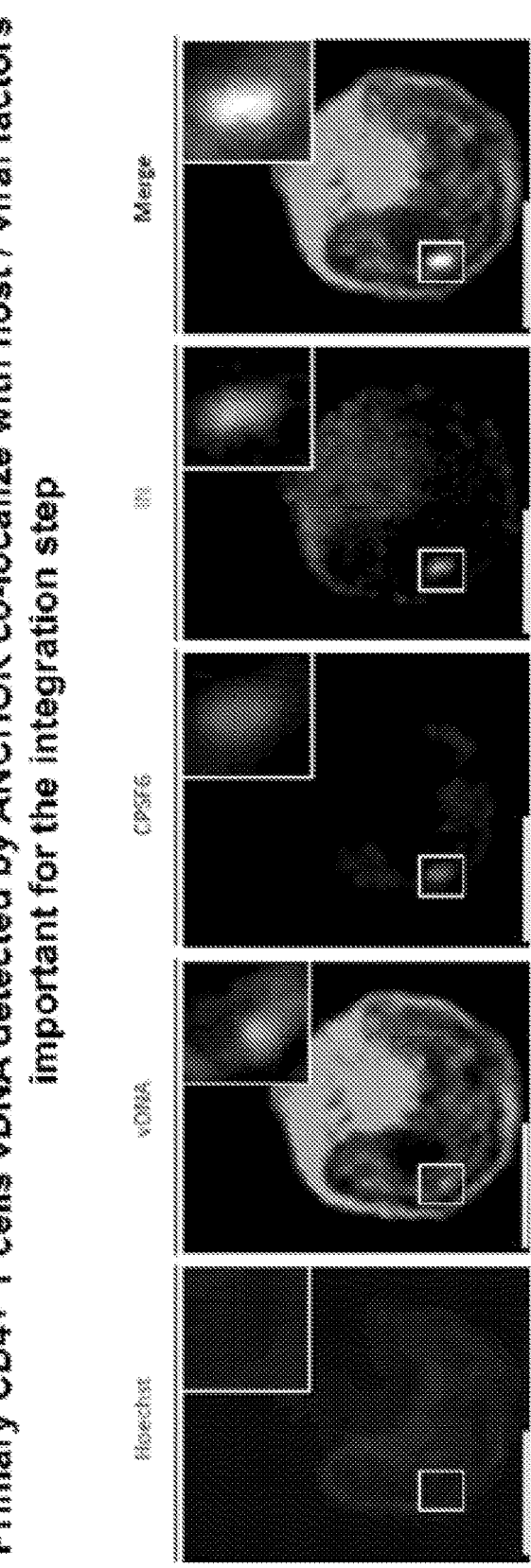

FIG. 13. HIV-1 ANCHOR versatile tool to detect inte-grated or episomal forms in cell lines or primary cells. a) (Figure on the top) Single clone carrying an individual provirus can be detected by imaging as well as by qPCR (Alu PCR). (Figure on the bottom) HIV-1 ANCHOR system efficiently label episomal viral DNA (RAL or virus integra-tion deficient (IN D116A). b) HIV major target cells can be followed after infection using HIV-1 ANCHOR system. c) HIV-1 ANCHOR is a tool to study viral interaction with host and viral factors, such as IN and CPSF6 by imaging.

Figure 14:
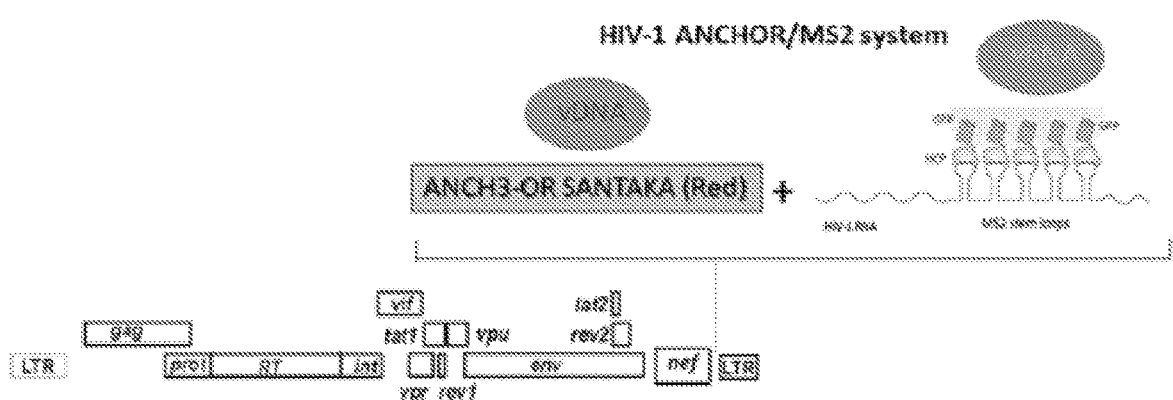
Figure 14:
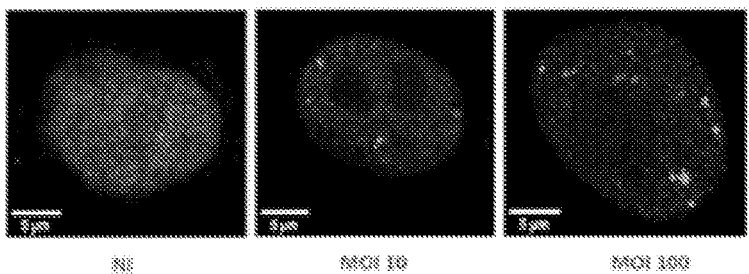

FIG. 14. HIV-1 ANCHOR allows to follow the fate of HIV-1 genomes. a) HIV-1 ANCHOR allows the visualiza-tion of transcribed or untranscribed viral DNA (important for study of viral reservoirs). Intranuclear co-localization of viral DNA and viral RNA by coupling HIV-1 ANCHOR system with RNA FISH in HeLa and Jurkat cells expressing OR-GFP and infected with HIV-1 ANCHOR. b) Live imag-ing to study the dynamic of viral transcription coupling ANCHOR system to visualize the DNA with MS2 to visu-alize viral transcripts in HeLa cells or primary CD4+ T cells.

Figure 15:
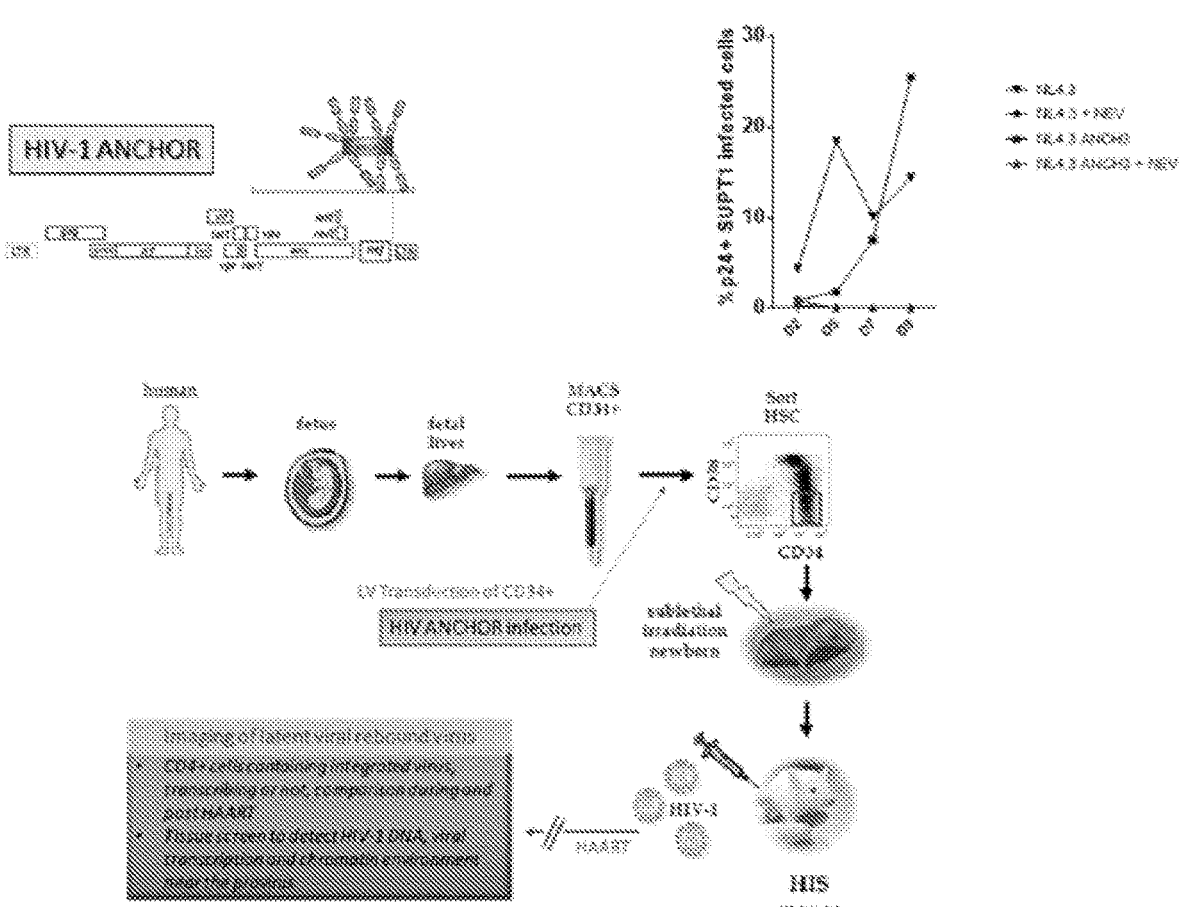

FIG. 15. HIV-1 ANCHOR for study on viral persistence or for in vivo model for gene therapy based on lentiviral vectors. Cartoon of the HIV-1 ANCHOR system using a replicative efficient virus. We generated a NL4.3 ANCH3 and a NL4.3/AD8 ANCH3 viruses. Viral fitness of these modified viruses has been followed in infected SupT1 cells for more than one week. Humanized mice can be infected with these viruses for study of viral persistence.

Figure 16:
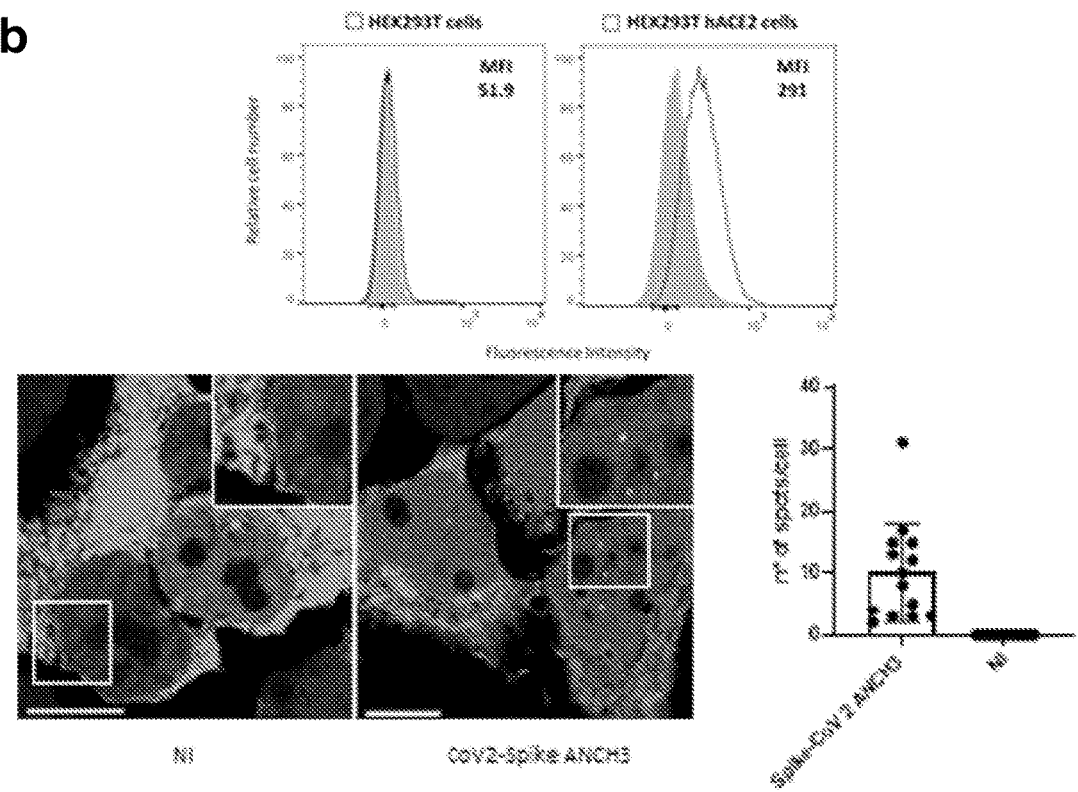
Figure 16:
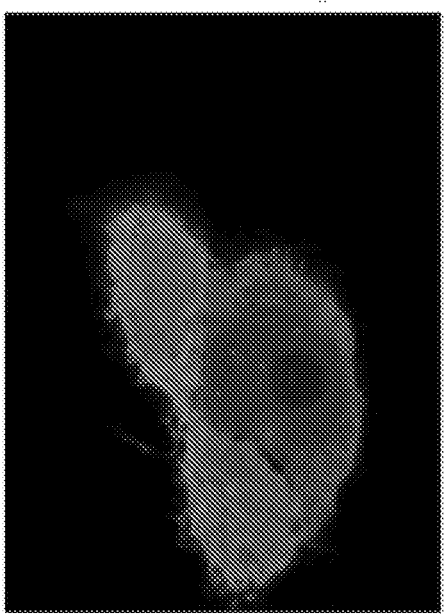
Figure 16:
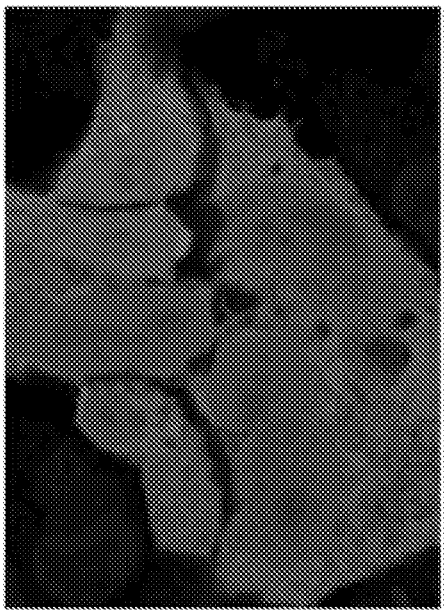

FIG. 16. Single cell live imaging for a fast and efficient drug screening against SARS-CoV2. a) Cartoon describing the system: lentiviral particles carrying the sequence ANCH3 are pseudotyped with Spike(S) from SARS-CoV2 to infect cell lines stably expressing ACE2 (NCBI reference NG_012575) and OR-GFP. b) Cytofluorimetric analysis shows the positivity of ACE2 stably transduced 293T cells. ACE2 positive cells transduced with Spike-CoV2 LV ANCH3 show nuclear green spots in the nucleus contrary to uninfected cells analyzed by IF. Graph on the right shows the quantification of nuclear spots using Fiji. c) 293T expressing ACE2 were infected in presence or not of HCQ and analyzed at confocal microscope.

Figure 17:
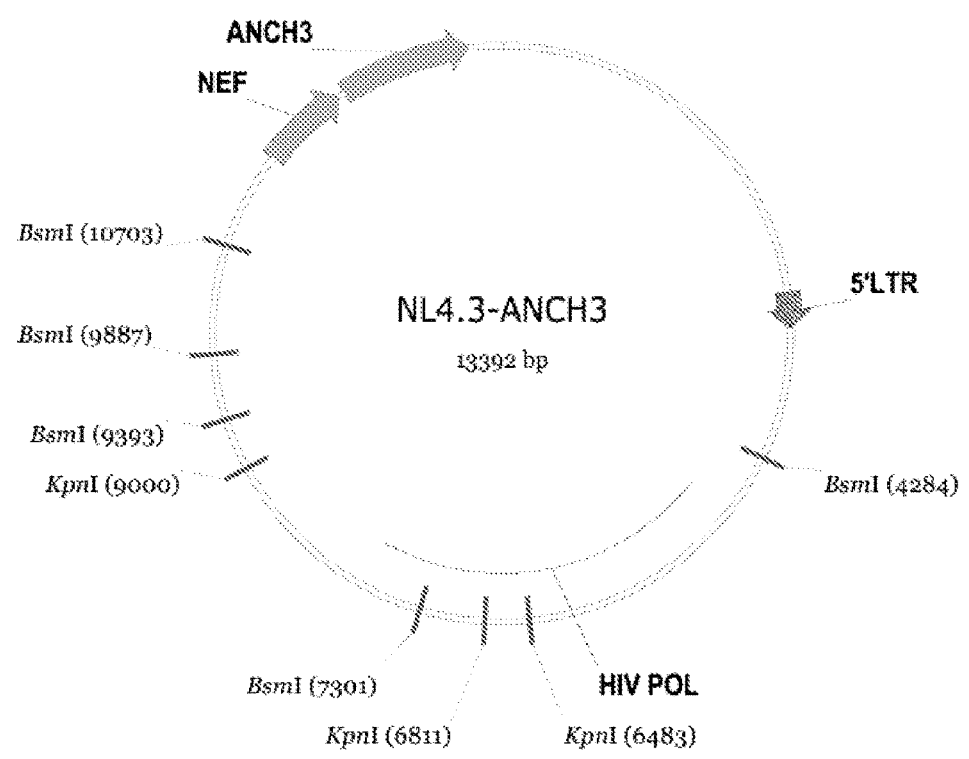

FIG. 17. Map of the NL4.3ANCH3 virus.

Figure 18:
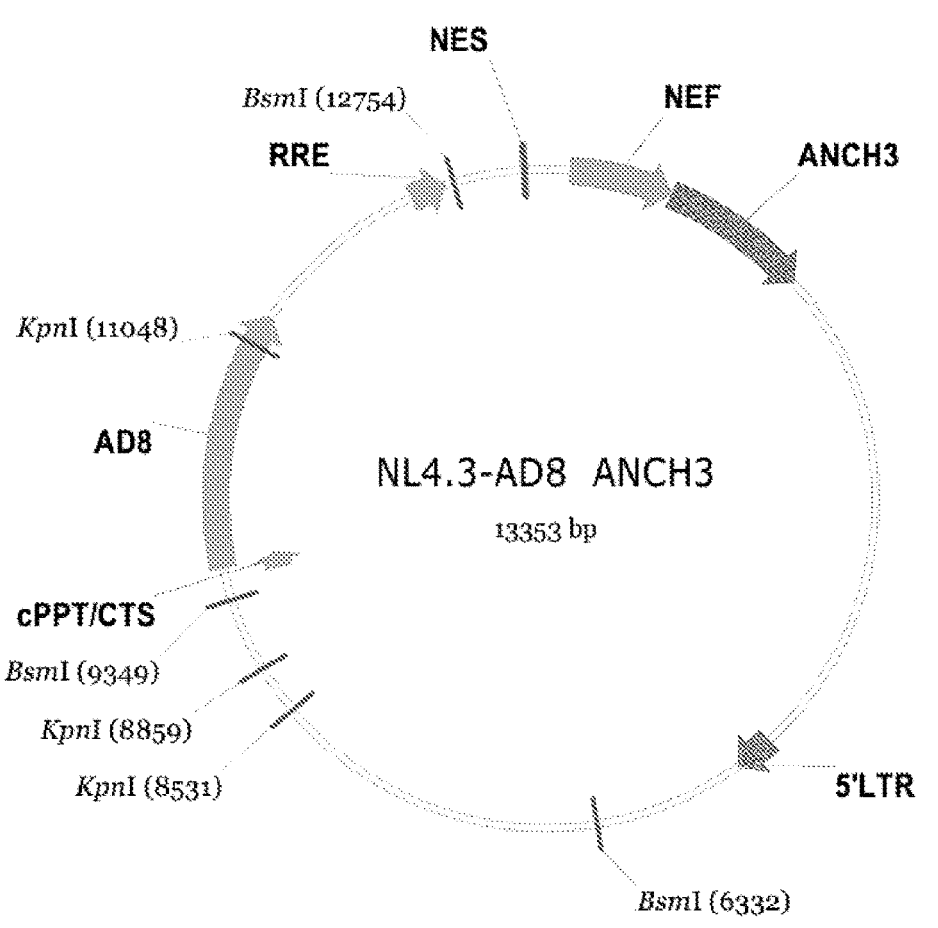

FIG. 18. Map of the NL4.3/AD8 ANCH3 virus.

TABLE 1

Sequences of the 24 probes against the viral RNA of POL gene used for RNA FISH are shown.

| Probe Name | Sequence | SEQ ID NO |
|---|---|---|
| HIV1-01 | GGG GAT TGT AGG GAA TTC CAA ATT CCT GCT TTT ACA CTC GGA CCT CGT CGA CAT GCA TT | 9 |
| HIV1-02 | CTT TTA GCT GAC ATT TAT CAC AGC TGG CTA TTA CAC TCG GAC CTC GTC GAC ATG CAT T | 10 |
| HIV1-03 | GTG TGC TGG TAC CCA TGC CAG ATA GAC TTA CAC TCG GAC CTC GTC GAC ATG CAT T | 11 |
| HIV1-04 | AAT ACT GGA GTA TTG TAT GGA TTT TCA GGC CCT TAC ACT CGG ACC TCG TCG ACA TGC ATT | 12 |
| HIV1-05 | TTT TAC TGG TAC AGT CTC AAT AGG GCT AAT GGT TAC ACT CGG ACC TCG TCG ACA TGC ATT | 13 |
| HIV1-06 | TAT GTT GAC AGG TGT AGG TCC TAC TAA TAC TGT TAC ACT CGG ACC TCG TCG ACA TGC ATT | 14 |
| HIV1-07 | CTA ATC CTC ATC CTG TCT ACT TGC CAT TAC ACT CGG ACC TCG TCG ACA TGC ATT | 15 |
| HIV1-08 | CAA TCA TCA CCT GCC ATC TGT TTT CCA TTT ACA CTC GGA CCT CGT CGA CAT GCA TT | 16 |
| HIV1-09 | TTT CCA AAG TGG ATT TCT GCT GTC CCT GTA TTA CAC TCG GAC CTC GTC GAC ATG CAT T | 17 |
| HIV1-10 | TTG TGG ATG AAT ACT GCC ATT TGT ACT GCT GTT ACA CTC GGA CCT CGT CGA CAT GCA TT | 18 |

TABLE 1-continued

Sequences of the 24 probes against the viral RNA of POL gene used
for RNA FISH are shown.

| Probe Name | Sequence | SEQ ID NO |
|---|---|---|
| HIV1-11 | TTA AGA TGT TCA GCC TGA TCT CTT ACC TGT TTA CAC TCG GAC CTC GTC GAC ATG CAT T | 19 |
| HIV1-12 | TAC AGT CTA CTT GTC CAT GCA TGG CTT CTT ACA CTC GGA CCT CGT CGA CAT GCA TT | 20 |
| HIV1-13 | TCA TGT TCA TCT TGG GCC TTA TCT ATT CCT TAC ACT CGG ACC TCG TCG ACA TGC ATT | 21 |
| HIV1-14 | TGT CAG TTA GGG TGA CAA CTT TTT GTC TTC CTT TAC ACT CGG ACC TCG TCG ACA TGC ATT | 22 |
| HIV1-15 | TGC TCC TAC TAT GGG TTC TTT CTC TAA CTT TAC ACT CGG ACC TCG TCG ACA TGC ATT | 23 |
| HIV1-16 | TCT GTT AGT GCT TTG GTT CCT CTA AGG AGT TTT TAC ACT CGG ACC TCG TCG ACA TGC ATT | 24 |
| HIV1-17 | CTG TAT GTC ATT GAC AGT CCA GCT GTC TTT TTT ACA CTC GGA CCT CGT CGA CAT GCA TT | 25 |
| HIV1-18 | TGG CAG CAC TAT AGG CTG TAC TGT CCT TAC ACT CGG ACC TCG TCG ACA TGC ATT | 26 |
| HIV1-19 | TCT GAT GTT TTT TGT CTG GTG TGG TAA GTC CCT TAC ACT CGG ACC TCG TCG ACA TGC ATT | 27 |
| HIV1-20 | CCT CAA CAG ATG TTG TCT CAG CTC CTC TTA CAC TCG GAC CTC GTC GAC ATG CAT T | 28 |
| HIV1-21 | ATT GCT GGT GAT CCT TTC CAT CCC TGT TAC ACT CGG ACC TCG TCG ACA TGC ATT | 29 |
| HIV1-22 | TTT CTT TTT TAA CCC TGC GGG ATG TGG TAT TCT TAC ACT CGG ACC TCG TCG ACA TGC ATT | 30 |
| HIV1-23 | TTT AAC TTT TGG GCC ATC CAT TCC TGG CTT ACA CTC GGA CCT CGT CGA CAT GCA TT | 31 |
| HIV1-24 | CCC TAT CTT TAT TGT GAC GAG GGG TCG TTG TTA CAC TCG GAC CTC GTC GAC ATG CAT T | 32 |

DETAILED DESCRIPTION

ANCHOR Systems

ANCHOR is a bipartite system derived from a bacterial parABS chromosome segregation machinery. Under its natural form in bacteria, the parABS system consists in a short non repetitive target DNA sequence containing a limited number of nucleation parS sites to which parB proteins bind and then spread onto adjacent DNA through a mechanism of protein-protein interaction. The third component of the system is an ATPase involved in the last steps of bacterial chromosomes or plasmids segregation. Under its engineered form, called ANCHOR, OR proteins (ParB) specifically bind to the cognate, shortened, ANCH sequence, which comprises palindromic parS nucleation sites (Graham et al., Genes Dev., 2014; Sanchez et al., 2015. Cell Syst). If the OR protein is fused to a fluorescent protein (FP), its accumulation on the ANCH target sequence and spread over neighboring sequences may result in the formation of an easily detectable fluorescent focus, thereby identifying the position of the ANCH-tagged DNA locus. Different ANCHOR systems (1 to 4, derived from various bacteria) have been used successfully to analyze the motion of single genomic locus and DNA double-strand break processing in living *Saccharomyces cerevisiae* cells and chromatin dynamics during transcription in human cells. These ANCHOR systems were shown not to perturb chromatin structure and function despite the presence of up to 500 OR proteins on and around the ANCH sequence.

Exemplary ANCHOR systems are disclosed in Saad H, Gallardo F, Dalvai M, Tanguy-le-Gac N, Lane D, Bystricky K. 2014. DNA dynamics during early double-strand break processing revealed by non-intrusive imaging of living cells. PLOS Genet 10:e1004187. The disclosed systems used in the reference are based on the ParB-parS loci of chromosomes c2 and c3 of *Burkholderia cenocepacia* J231. The authors adapted this system for use in eukaryotes, renaming the ~1 kb parS DNA segment "INT" and the ParB proteins from the c2 and c3 chromosomes ParB1 and ParB2, respectively. Nearly all the protein is bound loosely (because non-specifically) to DNA within and flanking the INT segment and is readily displaced during transcription or repair. The ParB-INT systems did not interfere with normal growth, nor did they require host factors. A skilled artisan will appreciate that in certain embodiments the systems disclosed in Saad, et al., are alternatives that may be incorporated for use in the invention.

In the context of the present invention, the ANCH sequence and OR protein refer generally to any sequence and the cognate protein designed from a natural bacterial partitioning system and more specifically on the ParS sequence and ParB protein of such a system. The skilled person knows how to identify suitable sequences, or use the ANCHOR system commercialized by NeoVirTech SAS.

In a preferred embodiment the ANCHOR system is an ANCH3 system.

In a preferred embodiment the ANCH3 sequence has the sequence used in the kit commercialized by NeovirTech SAS, having 3 repeats of the motif $N_1N_2N_3N_4N_5N_6CGN_7N_8N_9N_{10}N_{11}N_{12}$ (SEQ ID NO: 1), wherein the pairs of nucleotides $(N_6, N_7)$, $(N_5,N_8)$, $(N_4,N_9)$, $(N_3,N_{10})$, $(N_2,N_{11})$ and $(N_1,N_{12})$ are, independently of the other pairs, chosen in the list consisting of (A, T), (T, A), (C, G) et (G, C).

Preferred ANCH motifs are disclosed in WO2012127047, especially the nucleotidic formula $N_1N_2TN_3N_4N_5N_6CGN_7N_8N_9N_{10}AN_{11}N_{12}$ (I) (SEQ ID NO: 2), wherein Ni and $N_{12}$ are the same or different, and are nucleotides chosen amongst A, G, C or T, and the pairs of nucleotides $(N_6,N_7)$, $(N_5, N_8)$, $(N_4,N_9)$, $(N_3,N_{10})$ and $(N_2, N_{11})$, are independently of each other, chosen in the list consisting of (A, T), (T, A), (C, G) et (G, C), and wherein the nucleotides $N_1$ and $N_{12}$ may potentially be absent.

According to a preferred embodiment disclosed in WO2012127047, N1 is absent or is G, C or T, the pair $(N_6,N_7)$ is (A, T), (T, A) or (G, C); the pair $(N_5,N_8)$ is (C, G) or (T, A); the pair $(N_4,N_9)$ is (A, T), (T, A), (C, G) or (G, C); the pair $(N_3, N_{10})$ is (G, C) or (T, A); the pair $(N_2,N_{11})$ is (T, A) or (G, C) and $N_{12}$ is absent or is A or C.

At the recognition site the symmetric nature $(N_2$ to $N_6$ with $N_7$ to $N_{11})$ is most important for recognition. It is therefore possible that a sequence of same symmetric organization, without necessarily having nucleotide identity, is able to have the same characteristics.

In particular, the recognition site recognised by a DNA binding protein belonging to the partitioning system of bacterial DNA used in the present invention is of nucleotide sequence (II) or a sequence complementary to nucleotide sequence (II):

$N_{13}TTN_{14}N_{15}N_{16}N_{17}CGN_{18}N_{19}N_{20}N_{21}AAC$ (II) (SEQ ID NO: 3) in which: $N_{13}$ represents G. C or T; the pair $(N_{14}, N_{21})$ represents (T,A) or (G,C); the pair $(N_{15},N_{20})$ represents (A,T) or (T,A); the pair $(N_{16}, N_{19})$ represents (T,A) or (C,G); the pair $(N_{17},N_{18})$ represents (G,C) or (A,T). Advantageously the recognition site recognised by a DNA binding protein and belonging to the partitioning system of bacterial DNA has a nucleotide sequence chosen from among the following nucleotide sequences:

GTTTATGCGCATAAAC (Sc2; SEQ ID NO: 4); CTT-TATGCGCATAAAC (Sc2; SEQ ID NO: 5); GTTGT-CACGTGACAAC (Sc3; SEQ ID NO: 6); TTTGT-CACGTGACAAC (Sc3; SEQ ID NO: 7); CTTGTCACGTGACAAC (Sc3, SEQ ID NO: 8); and a sequence complementary to any one of these sequences.

The OR protein is a DNA binding protein belonging to the partitioning system of bacterial DNA, a derivative or fragment thereof, specifically recognizing its cognate ANCH sequence. The skilled person knows how to choose the protein recognizing its cognate ANCH sequence, as disclosed in WO2012127047.

The DNA binding proteins belonging to the partitioning system of bacterial DNA, their amino acid sequence and/or the nucleotide sequences encoding the same are accessible in the databases of amino acid or nucleotide sequences such as Genbank or NCBI genome project for those bacteria whose genome has been sequenced in full or in part. If necessary, those skilled in the art may use already described ParB protein sequences to identify the analogue of the latter in a bacterium whose genome has not been fully sequenced or for which the DNA binding protein belonging to the partitioning system of bacterial DNA is not yet known.

Advantageously the fragment of a DNA binding protein belonging to the partitioning system of bacterial DNA, and in particular of a ParB protein of Bcc (*Burkholderia cenocepacia*), contains at least the motif involved in DNA binding. Said motif corresponds to the motif having a helix-turn-helix structure (HTH) such as described in Dubarry et al., J Bacteriol. 2006. The HTH motif notably corresponds to the sequence lying between amino acids 202 and 225 of sequence SEQ ID NO: 2 of WO2012127047 (SEQ ID NO:33 of the sequence listing part of the present application). It is to be noted however that not every DNA binding protein belonging to the partitioning system of bacterial DNA necessarily has a DNA binding motif of HTH structure. The homologue of the ParB protein in the bacterium TP228 for example has a motif of ribbon-helix-helix structure at the C-terminal end (Golovanov et al, Mol Microbiol. 2003).

In a preferred embodiment the OR protein is fused to a fluorescent protein chosen among CFP, GFP, OFP and RFP.

In a preferred embodiment the OR protein is fused to GFP.

According to another embodiment, the OR protein can be fused to any other detectable protein. This embodiment is applicable to all the aspects of the invention.

In a preferred embodiment the OR protein is fused to RFP.

Recombinant Lentiviral Vector

This invention provides recombinant lentiviral vectors useful for observing lentiviral DNA in a eukaryotic cell. In some embodiments the recombinant lentiviral vector comprises a coding sequence for an OR protein fused to a coding sequence for a fluorescent protein or a subunit of a fluorescent protein, and a promoter active in human cells operatively linked to the coding sequences.

In a preferred embodiment the OR protein is fused to GFP. In other embodiments the fluorescent protein is an mCherry protein. In some embodiments the fluorescent protein is a split fluorescent protein. Examples known in the art include split-sfCherry2$^{1-10/11}$ and split-mNeonGreen2$^{1-10/11}$.

In some embodiments of the fusion protein the fluorescent protein is N-terminal to the OR protein. In some embodiments of the fusion protein the OR protein is N-terminal to the fluorescent protein. The term "OR-GFP" in this application means equally fusion protein with OR protein in N-terminal to the fluorescent protein and fusion protein with OR protein in C-terminal to the fluorescent protein. In some embodiments the fusion protein comprises more than one copy of the OR protein and/or the fluorescent protein.

In some embodiments the fusion protein further comprises the MS2 coat protein (MCP), useful for MS2 binding sites that may be incorporated into a lentiviral RNA. In some embodiments the MCP is located N-terminal to the OR protein. In some embodiments the OR protein is located N-terminal to the MCP.

In some embodiments the recombinant lentiviral vector further comprises a 5'-LTR and a 3'-LTR; and/or a cPPT/CTS sequence. According to a preferred embodiment, the vector does not comprise any sequence corresponding to a binding site of the OR protein. In some embodiments the vector is an HIV-1 HIV-1 vector, an HIV-2 vector, or an SIV vector. In some embodiments the vector is LVCMVOR-GFP.

The map of the LVCMVOR-GFP vector is in FIG. 5.

In some embodiments the promoter active in human cells is selected from CMV, EF1A, SV40, RSV, K14, PGK, Ubc, Beta globin, H1, and U6. A skilled artisan will appreciate that numerous other promoters are known in the art which may be used.

Recombinant Lentivirus or Retrovirus

This invention provides recombinant lentivirus or retrovirus comprising an ANCH sequence that makes the virus useful for observing lentiviral or retroviral DNA in a eukaryotic cell. The recombinant lentivirus or retrovirus may be used in conjunction with a recombinant lentiviral vector of the invention and/or a recombinant cell of the invention.

In some embodiment the recombinant lentivirus or retrovirus comprises a recombinant genome comprising an RNA that generates an ANCH sequence upon retrotranscription. In some embodiments the ANCH sequence is an ANCH3 sequence.

In some embodiments the recombinant genome is ΔEnv and ΔNef. In some embodiments the recombinant genome is wild type (Env and Nef sequences are present). According to a preferred embodiment, the recombinant lentivirus or retrovirus does not comprise any sequence coding for an OR protein, either at the RNA level or after retro-transcription. In some embodiments the recombinant genome encodes an HA-tagged integrase protein ($IN_{HA}$). In some embodiments the lentivirus is selected from HIV-1, HIV-2, and SIV. In some embodiments the genome of the recombinant virus further comprises at least one MS2 binding site. In some embodiments the MS2 binding site is 5' to the ANCH3 sequence. In some embodiments the MS2 binding site is 3' to the ANCH3 sequence.

In some embodiments the recombinant lentivirus or retrovirus is pseudotyped. In a preferred embodiment it is pseudotyped with a VSV-G envelope.

In alternative embodiments, the recombinant lentivirus or retrovirus is pseudotyped by any viral protein envelope of a second virus, wherein said second virus is preferably not a retrovirus. The recombinant lentivirus or retrovirus of the invention is advantageously pseudotyped with a protein envelope from a SARS-CoV2.

The map of the recombinant lentivirus Bru LAI delta env IN HA ANCH3 (deltaNef) is presented in FIG. 6.

In alternative embodiments the invention provides a recombinant retrovirus comprising an ANCH sequence that makes the virus useful for observing retroviral DNA in a eukaryotic cell, wherein the retrovirus is chosen from lentiviruses and Human T-lymphotropic virus (HTLV), Bovine Leukemia virus (BLV) and Moloney virus (MLV).

Recombinant Eukaryotic Cells

In another aspect recombinant eukaryotic cells are provided. In some embodiments the eukaryotic cells are human cells. In some embodiments the eukaryotic cells are primate cells. In some embodiments the eukaryotic cells are primary cells. In some embodiments the eukaryotic cells are a cell line, such as HeLa cells or HEK-293 cells. In some embodiments the eukaryotic cells are cells from humanized mice.

In some embodiments the recombinant cells comprise a genomically integrated DNA copy of a recombinant lentiviral vector. In some embodiments the recombinant lentiviral vector is any of the recombinant lentiviral vectors disclosed herein. For example, the recombinant lentiviral vector may comprise a coding sequence for an OR protein fused to a coding sequence for a fluorescent protein or a subunit of a fluorescent protein, and a promoter active in human cells operatively linked to the coding sequences. In some embodiments the coding sequence for the OR protein is fused to a coding sequence for green fluorescent protein (GFP). In some embodiments the promoter is the cytomegalovirus (CMV) promoter. In some embodiments the vector further comprises the coding sequence for MS2 coat protein (MCP) fused to a coding sequence for a fluorescent protein or a subunit of a fluorescent protein, and a promoter active in human cells operatively linked to the coding sequences. In some embodiments the vector comprises a 5'-LTR and a 3'-LTR. In some embodiments the vector comprises a cPPT/CTS sequence. In some embodiments the vector is an HIV-1 vector. In some embodiments the vector is LVCMVOR-GFP.

In some embodiments the recombinant cells comprise a DNA copy of a recombinant lentiviral vector localized in the nucleus but not integrated in the chromosome of the cell.

According to another aspect, the recombinant eukaryotic cells of the invention comprise a recombinant lentivirus according to the invention, in a retrotranscribed form, integrated or not in the genome of the cells. Such eukaryotic cells are preferably human cells; they can be used in combination with a recombinant lentiviral vector of the invention.

The eukaryotic cell of the invention is preferentially an isolated cell. According to some embodiments, it is not an embryonic stem cell, especially not a human embryonic stem cell obtained by destruction of a human embryo.

According to another embodiment, the recombinant eukaryotic cell is transitionally transformed with a recombinant lentiviral vector according to the invention; the vector is thus not integrated into the genome of the cell.

Methods

In another aspect this invention provides methods of observing lentiviral DNA in a eukaryotic cell. In some embodiments the method is in addition for observing lentiviral RNA in eukaryotic cell. In some embodiments the method comprises providing a recombinant eukaryotic cell that produces a fusion protein comprising an OR protein, fused to a fluorescent protein or a subunit of a fluorescent protein; infecting the recombinant eukaryotic cell with a recombinant lentivirus comprising a recombinant genome comprising an RNA that generates an ANCH sequence upon retrotranscription, under conditions sufficient for reverse transcription of the recombinant lentiviral genome comprising an ANCH sequence; allowing the OR protein to bind to the ANCH sequence; and detecting the fluorescent protein or subunit of the fluorescent protein to thereby observe the lentiviral DNA in the eukaryotic cell.

In some embodiments the method further comprises making the recombinant eukaryotic cell that produces a fusion protein comprising an OR protein, fused to a fluorescent protein or a subunit of a fluorescent protein, by a method comprising transducing a eukaryotic cell with a lentiviral vector comprising a coding sequence for the fusion protein comprising an OR protein, fused to a fluorescent protein or a subunit of a fluorescent protein, and a promoter active in human cells operatively linked to the coding sequences.

Any recombinant eukaryotic cell and any lentiviral vector of the invention may be used in the methods. Exemplary embodiments of lentiviral vectors include those in which the OR protein is fused to green fluorescent protein (GFP). In some embodiments the promoter is the cytomegalovirus (CMV) promoter. In some embodiments the fusion protein further comprises an MS2 coat protein (MCP). In some embodiments the vector comprises a 5'-LTR and a 3'-LTR.

In some embodiments the vector comprises a cPPT/CTS sequence. In some embodiments the vector is an HIV-1 vector. In some embodiments the vector is LVCMVOR-GFP.

Any recombinant lentivirus or retrovirus of the invention may be used in the methods. Exemplary embodiments include that the ANCH sequence is an ANCH3 sequence. In some embodiments the recombinant genome is ΔEnv and ΔNef. In some embodiments the recombinant genome is wild type. In some embodiments the recombinant genome encodes an HA-tagged integrase protein (INHA). In some embodiments the lentivirus is HIV-1. In some embodiments the genome of the virus further comprises at least one MS2 binding site. In some embodiments the recombinant lentivirus or retrovirus is pseudotyped with a VSV-G envelope, or with any other viral envelope.

In some embodiments the methods comprise live imaging of the nuclear fate of the lentiviral DNA, such as HIV-1 DNA.

In some embodiments the lentiviral or retroviral DNA is observed in the cytoplasm of the eukaryotic cell. The lentiviral or retroviral DNA bound to the OR protein can be observed, for example, as described in the Examples, at various time points to define the process and rates of reverse transcription in the presence and/or absence of various test compounds.

In some embodiments the lentiviral or retroviral DNA is observed during nuclear translocation. The lentiviral or retroviral DNA bound to the OR protein can be observed, for example, as described in the Examples, at various time points to define the process and rates of nuclear translocation in the presence and/or absence of various test compounds.

In some embodiments the lentiviral or retroviral DNA is observed in association with viral integrase.

In some embodiments the lentiviral or retroviral DNA is present in a pre-integration complex (PIC).

In some embodiments the lentiviral or retroviral DNA is observed in the nucleus. The lentiviral or retroviral DNA bound to the OR protein can be observed, for example, as described in the Examples, at various time points to define the process and rates of integration in the presence and/or absence of various test compounds.

In some embodiments the lentiviral or retroviral DNA is observed integrated into the host cell genome.

In some embodiments the lentiviral or retroviral DNA is observed with single molecule resolution.

In some embodiments the lentiviral or retroviral DNA is observed integrated into the genome of a eukaryotic host cell. The eukaryotic host cell may be a primary cell or a cell line cell. The eukaryotic host cell may be a human cell or a primate cell.

In some embodiments the lentivirus is latent i.e. the lentivirus is integrated in the eukaryotic host cell chromosome and the lentiviral genome is replicated during host cell division but the lentivirus is transcriptionally silent (Ruelas D S, Greene W C. An integrated overview of HIV-1 latency. Cell. 2013 Oct. 24; 155 (3): 519-29).

In some embodiments the methods further comprise live imaging of the newly transcribed lentiviral or retroviral RNA.

In another aspect the invention provides a method of characterizing an agent that interferes with lentiviral or retroviral nuclear translocation and/or integration, comprising performing a method of observing lentiviral or retroviral DNA in a eukaryotic cell of the invention in the presence of an agent and determining whether the agent interferes with lentiviral or retroviral nuclear translocation and/or integration. In some embodiments the method further comprises performing the method of observing lentiviral or retroviral DNA in a eukaryotic cell in the absence of the agent; wherein determining whether the agent interferes with lentiviral or retroviral nuclear translocation and/or integration comprises comparing lentiviral or retroviral nuclear translocation and/or integration in the presence of the agent with lentiviral or retroviral nuclear translocation and/or integration in the absence of the agent. In some embodiments the agent interferes with lentiviral or retroviral nuclear translocation. In some embodiments the agent does not interfere with lentiviral or retroviral nuclear translocation. In some embodiments the agent interferes with lentiviral or retroviral integration. In some embodiments the agent does not interfere with lentiviral or retroviral integration. An exemplary agent is PF74 that modulates the capsid core stability and impedes viral nuclear entry.

The methods of the invention are preferably carried out ex vivo or in vitro.

In still another aspect the invention provides a method of characterizing an agent that interferes with the interactions between the cellular receptor and the viral proteins responsible for the penetration of a given second virus, comprising performing a method of observing retroviral DNA in a eukaryotic cell of the invention in the presence of an agent and determining whether the agent interferes with penetration of said second virus, wherein said retroviral DNA is retrotranscribed from a recombinant retrovirus according to the invention, pseudotyped with the envelope proteins of said second virus. In some embodiments the method further comprises performing the method of observing retroviral DNA in a eukaryotic cell in the absence of the agent; wherein determining whether the agent interferes with penetration of said second virus comprises comparing retroviral nuclear translocation and/or integration in the presence of the agent with retroviral nuclear translocation and/or integration in the absence of the agent. An exemplary agent is hydroxychloroquine which inhibits viral entry of a recombinant lentivirus pseudotyped with the Spike envelope of SARS-Cov2.

The invention thus allows screening of agents potentially inhibiting or increasing cell penetration of any given virus, using a recombinant retrovirus of the invention, pseudotyped with the envelope protein of said given virus.

According to an embodiment, the invention also concerns a method for screening in vitro or ex vivo agents potentially interfering with the penetration of a recombinant retrovirus, the method comprising detecting in a recombinant eukaryotic cell according to the invention or an eukaryotic cell transitionally transformed with a recombinant lentiviral vector of the invention, viral DNA retrotranscribed from a recombinant retrovirus of the invention, in presence and in absence of said potential agent.

Alternatively, the invention also comprises a method for screening in vitro or ex vivo agents potentially interfering with the penetration of a virus, comprising detecting in a recombinant eukaryotic cell of the invention or an eukaryotic cell transitionally transformed with a recombinant lentiviral vector of the invention, viral DNA retrotranscribed from a recombinant retrovirus according to the invention, pseudotyped with the viral envelope protein of said virus, in the presence and in the absence of the tested agent. The eukaryotic cell expresses the receptor interacting with said viral envelope protein for its entry, either naturally or after genetic modification and is thus a permissive cell for the virus.

In a further embodiment, the invention is directed to the use of a recombinant lentiviral vector of the invention, a recombinant retrovirus of the invention and/or a recombinant eukaryotic cell of the invention, to screen for potential agent interacting with the nuclear translocation and/or integration of the recombinant virus, either enhancing or inhibiting these processes. A preferred use is in vitro or ex vivo. The recombinant virus is either a recombinant lentivirus or retrovirus of the invention, or a pseudotyped recombinant retrovirus or lentivirus of the invention.

The invention also concerns non therapeutic uses of a recombinant lentiviral vector of the invention, a recombinant retrovirus of the invention and/or a recombinant eukaryotic cell of the invention, to detect, follow or study the infection cycle of a recombinant retrovirus of the invention, potentially pseudotyped, in a non-human eukaryote.

According to a further aspect, the invention is also directed to a kit-of-parts, comprising a recombinant lentiviral vector according to the invention, which comprises the sequence encoding an OR protein, and a recombinant lentivirus or retrovirus, potentially pseudotyped, according to the invention thus comprising the sequences corresponding to an ANCH sequence, once retrotranscribed, said sequence being the cognate sequence of the OR protein. Alternatively, the invention also concerns a kit comprising a recombinant eukaryotic cell, comprising a genomically integrated DNA copy of a recombinant lentiviral vector of the invention, and a recombinant lentivirus or retrovirus, potentially pseudotyped, according to the invention. Preferably, the cell is genetically modified to express the corresponding receptor of the viral envelope used for the pseudotyping. An example of such a situation is illustrated in example 10, wherein cells modified to express the receptor of the SARS-Cov-2 are used in combination with a recombinant retrovirus of the invention, pseudotyped with the Spike S protein of said SARS-Cov-2.

The kits of the invention can advantageously be used for the different methods disclosed above and in the examples. The kits may contain instructions for use to carry out these methods.

As immediately apparent from the preceding and from the description of the vector and recombinant virus of the invention, the imaging of the retrotranscribed viral DNA of the recombinant virus is only dependent on its retrotranscription, and independent on its transcription or translation, as the OR protein is not encoded by the recombinant virus. The system disclosed in the present invention and its different elements are thus particularly adapted to the study of latent retrovirus such a s HIV-1, for which transcription and translation may occur late in the viral cycle.

EXAMPLES

Example 1: Materials and Methods

Cells. HeLaP4R5 cells, a HeLa-CD4/LTR-lacZ indicator cell line expressing both CXCR4 and CCR5, were employed to assess viral infectivity[41] using a beta gal assay. 293T cells (ATCC) are human embryonic kidney cells used to produce lentiviral vectors and HIV-1 viruses, HeLa cells (ATCC) derived from cervical cancer cells. CD4+ T cells were isolated from healthy donors.

Antibodies. Ab anti-actin HRP conjugated sc-2357 Santa Cruz (dil. 1:5000), Ab anti-p24 antibody NIH183-H12-5C (NIH reagent, IF dil. 1:400 or TEM 1:50) and the anti-HA high affinity antibody (11867423001) Roche (TEM 1:50 dilution or IF 1:500), Ab Goat anti-mouse Alexa Fluor Plus 488 (A32723) and Goat anti-rat Alexa 647 (A21247) Thermofisher scientific. Ab Goat anti-mouse 10 nm gold coupled (ab39619), Ab Goat anti-rat 6 nm gold coupled (ab105300) Abcam (dil. 1:50). Ab anti-GFP rabbit (ab183734) Abcam (CLEM dil. 1:50), Ab anti-GFP (Clontech #632592, WB dilution 1:1000), Ab Beta Actin HRP conjugated (Abcam, #8226 WB dil. 1:2,500), Ab Goat anti-rabbit Alexa 488 (A11078) (CLEM dil.1:50), Ab anti Nup153 9 (kind gift from B. Burke dil. 1:200).

Time-lapse microscopy. HeLaP4R5 cells stably transduced with LVCMVOR-GFP were plated in Hi-Q4 microdishes (10,000 cells per chamber) (Ibidi). The following day, cells were infected with HIV-1ΔEnvIN$_{HA}$ΔNef ANCH3/VSV-G or HIV-1ΔEnv IN$_{HA}$ (D116A) ΔNef ANCH3/VSVG complemented with the plasmid GIR using respectively MOI 25 and MOI 300. Transmission and fluorescence images were taken every 5 or 10 min for up to 96 h using a Nikon Biostation IMQ (40× objective) with 6-8 fields captured simultaneously for each condition or for up to 24 h by using a spinning-disk Ultra View VOX (Perkin-Elmer) (63× objective) with one field of view for each experiment in 2D or 3D. Images were analyzed in FIJI or Imaris.

RNA FISH. Cells were fixed with 4% paraformaldehyde and permeabilized in 70% ethanol overnight. Probes were pre-hybridized with a secondary probe conjugated to two Cy3 moieties via the readout sequence. Following FISH, cells were stained with DAPI in PBS (1:10000) for 5 minutes. Cells were mounted with ProLong Gold antifade mounting medium (Molecular Probes)[42]. Primary smiFISH probes have a targeting sequence and a shared readout sequence. smiFISH probes against HIV pol were designed with Oligostan[43] and purchased from Integrated DNA Technologies. Probe sequences used are described in table 1. Three-dimensional image stacks were captured on a widefield microscope (Nikon eclipse Ti) equipped with a 63×1.4 NA objective and a scMOS camera (Andor Neo 5.5) and controlled with MicroManager. Nuclei were segmented manually during the analysis. RNA molecules were detected automatically with FISH-quant in 3D2. Identical detection settings were used for all experimental conditions. Between 60-80 individual cells were analyzed for each experimental condition. Statistical analysis has been performed using Graph Pad Prism7.

Western blotting and confocal immunofluorescence microscopy. The expression of the correct size of the cDNA OR-GFP cloned in LV has been tested by western blotting. Proteins were extracted on ice from wild type and LVOR-GFP transduced HeLa cells using RIPA buffer (20 mM HEPES pH 7.6, 150 mM NaCl, 1% sodium deoxycholate, 1% Nonidet P-40, 0.1% SDS, 2 mM EDTA, complete protease inhibitor (Roche Diagnostics)), and protein concentration was quantified using the Dc Protein Assay (Bio-Rad Laboratories) with BSA as standard. Ten micrograms of total protein lysate was loaded onto SDS-PAGE 4-12% Bis Tris gels (Invitrogen). Revelation was carried out using the ECL Plus western blotting kit (GE Healthcare). Primary antibody used for western blotting (WB) was anti-GFP (Clontech #632592, dilution 1:1000). Secondary conjugated antibodies used for western blotting were Beta Actin HRP conjugated antibody (Abcam, #8226 1:2,500), and antirabbit IgG HRP (sc2357 Santa Cruz). Immunofluorescence microscopy: HeLa P4R5 cells stably expressing OR-GFP or not were plated onto 12 mm diameter coverslips in 24-well plates the day before and then infected with HIV-1ΔEnvIN$_{HA}$ΔNef ANCH3/VSV-G or HIV-1ΔEnvINHA/VSV-G at different MOIs and different time post infection. The cells were then washed, fixed with 4% PFA, permeabilized with Triton X-100 0.5% for 30 min and blocked with 0.3% bovine serum albumin (BSA). All incubations were carried out at room temperature and were followed by five PBS washes. Cells were incubated with primary antibodies for 1 h and secondary antibodies for 30 min. Antibodies were diluted in 0.3% BSA. Nuclei were stained with Hoechst (Invitrogen, dilution 1:10000). Finally, cells were mounted onto glass slides (Thermo Scientific) with Prolong Diamond (Life Technologies). Confocal microscopy was carried out on a Zeiss LSM700 using a 63× objective. Representative medial sections or combined Z-stacks are shown as indicated. Images were analyzed in FIJI.

Viral infection and sample preparation for electron microscopy. Eight million of HeLa P4R5 or Hela P4R5 OR-GFP transduced cells were seeded in a T75 flask and infected with 4000 ng of p24 of either HIV-1 IN-HA or HIV-1 ANCH3 and incubated for 6 h. When a WT virus has been used to infect HeLa P4R5 cells or primary CD4+ T cells a ultracentrifuged virus has been used with or without SEVI according a published protocol 44.45 (SEVI fibrils have been kindly provided by Franck Kirchhoff). Infectivity has been analyzed by beta gal assay or by FACS. Samples were prepared for EM as follows: cells were fixed by adding directly an equal volume of 8% paraformaldehyde, 0.2% glutaraldehyde in PHEM buffer (60 mM Pipes, 25 mM Hepes, 2 mM $MgCl_2$, 10 mM EGTA, pH 7.3) solution to the cells medium and incubated for 30 minutes. Next, the solution was exchanged by 4% paraformaldehyde diluted in PHEM buffer and incubated for 2 hours at room temperature. Cells were further prepared for cryomicrotomy and immunolabelled as described in[46]. Electron microscopy chemicals were purchased from Electron Microscopy Sciences (Pennsylvania). For the CLEM experiments before contrasting with uranyl acetate the samples were stained with Hoecht 1 μM for 20 minutes in water, washed and incubated with a solution of 0.2 μm Tetraspecks fluorescent beads (Thermofisher scientific) diluted 1:50 in PHEM buffer pH 7.3 for 20 minutes and washed 4 times 2 minutes with water. The samples were mounted on in a glass bottom petri dish (Miltenyi Biotec) with a drop of SlowFade Diamond antifade mountant (Thermofisher Scientific). The imaging process gave a mosaic map of the sections in the blue, green and far red channels using a 63×1.4 NA objective with a Leica DSM6000 microscope equipped with Orca Flash 4.0 LT camera (Hamamatsu Photonics). Then the grids were recovered by pouring 10 ul of water underneath them. Grids were washed contrasted and prepared for TEM as specified above. For the cryo-EM observation the samples were prepared as described above. After immunolabelling the grids were embedded with a mixture of 50% methylcellulose 2% and 50% sucrose 2.3M and then vitrified by plunge freezing with EMGP plunge freezer (Leica) at 30° C. and 90% humidity.

Electron microscopy data collection and image processing. Sections, at RT or in cryo, were transferred and imaged in a Thermo-Fischer T12 transmission EM operating at 120 or 80 kV equipped with a Gatan Ultrascan 4000 camera. Multiscale mapping and tilt series acquisitions in areas of interest were processed by a Serial EM software[47]. In case of cryo samples, low dose conditions and bi-directional tilt schemes were used during acquisition Tilt series stacks were initially aligned using cross-correlation and the alignments were further refined using the immunogold beads as registration fiducials in IMOD[48]. Tomograms were reconstructed with the weighted back-projection method and filtered to assist manual segmentation with IMOD. The correlation between fluorescence and electron microscopy were achieved using the following protocol: 1) z-stacks of every frame of the mosaic was projected with the FIJI's plugin extended depth of field[49]; 2) the frames were aligned and blended to generate a fluorescence map of the complete section using Mosaic J[50]; 3) the same cells was identified in both fluorescence and low resolution TEM section map; 4) the high precision correlation was obtained by identifying Tetraspecks positions in high resolution fluorescence and TEM images using ec-CLEM plugin[51] of Icy[52].

Distance of HIV particles to nuclear envelope was calculated in 2D images as follows. Position of HIV particles labelled with more than one gold either 6 or 10 nm were mark with the multipoint tool in FIJI. Nuclear envelope was manually outlined in FIJI. Closest distance of each HIV particle to nuclear envelope was calculated with a custom Python script using the shapely package (https://pypi.org/project/Shapely/). Only particles located within the nucleus were considered.

Quantitative PCR. Total cellular DNA was isolated using the QIAamp DNA micro kit (QIAGEN) at 7 and 24 h p.i. or from uninfected cells and then the genomic DNA was treated for 1 h at 37° C. with Dpn1. Ten micromolar of nevirapine was used in infected cells as control of the experiment. Late reverse transcription products at 7 h p.i. were measured by real-time PCR using primers and probe previously described[53], 2LTR containing circles were detected using primers MH535/536 and probe MH603, using as standard curve the pUC2LTR plasmid, which contains the HIV-1 2LTR junction. Integration was assessed by Alu-PCR, using primers designed in the U3 region of LTR[7] which is deleted in the LVs carrying OR-GFP but not in the LTR of HIV-1 used to challenge ORGFP stably expressing cells and control cells.

Plasmids and viral production. Plasmids HIV-1ΔEnv $IN_{HA}$ (D116A)ΔNef ANCH3 or HIV-1ΔEnv$IN_{HA}$ΔNef ANCH3 were obtained by insertional mutagenesis using Quik Change II XL Site-Directed Mutagenesis kit and the sequence ANCH3 has been cloned by PCR using as template the plasmid pANCH3 (NeoVirtech). The ANCHOR™ technology is the exclusive property of NeoVirTech. The LVCMVOR-GFP was generated by cloning by PCR OR-GFP from the plasmid pOR-GFP (NeoVirtech) in pTripCMVGFP. Lentiviral vectors and HIV-1 viruses were produced by transient transfection of 293T cells using calcium phosphate coprecipitation. Lentiviral vectors were produced by co-transfection of 10 μg of transfer vector LVCMVOR-GFP with 2.5 μg of pMD2 VSV-G and 10 μg of ΔR8.74 plasmids. HIV-1 viruses were produced by cotransfection with calcium phosphate with HIV-1 LAI (BRU) ΔEnv Virus (NIH) or with the modified versions HIV-1ΔEnvIN$_{HA}$ (kind gift from Fabrizio Mammano)[21] or HIV-1ΔEnvIN$_{HA}$ΔNef ANCH3 or HIV-1ΔEnv IN$_{HA}$ (D116A) ΔNef ANCH3 in combination with GIR (Gag-IN-Ruby plasmid)[37-38] and VSV-G envelope expression plasmid pHCMV-G (VSV-G). The viruses collected from 293T cells 48 h post transfection were ultracentrifuged at 4° C. for 1 h at 22,000 rpm. Virus normalizations were performed by p24 ELISA according to the manufacturer's instructions (Perkin Elmer). Infectivity has been tested by Beta-galactosidase assay (Merck) activity measured 48 h p.i. according to manufacturer's instructions, using a microplate fluorimeter (Victor, Perkin Elmer). Protein quantification by Bio-Rad protein assay was carried out on the same lysates to normalize the B-gal data for protein content.

Example 2: HIV-1 CA Remodeling During the Early Steps of Infection

In order to obtain an unobstructed view of the state of viral replication complexes at the inner and outer sides of the nuclear pore complex (NPC) we have coupled immunofluo-rescence assay with immunoelectron microscopy. The viral integrase cannot be efficiently labelled using a direct anti-body, thus to overcome this limitation we infected HeLa cells with HIV-1 containing a small HA tag fused at the C terminus of the IN (HIV-1ΔEnv IN$_{HA}$/VSV-G) (kindly gift from Fabrizio Mammano[21]). The genetically modified virus infects HeLa cells as well as T CD4-primary lymphocytes similarly to the WT virus (FIG. 1a, FIG. 7a). Cells fixed at 6 h post infection show an important percentage of colocal-ization of viral CA with the viral IN (~70%) (FIG. 1b, FIG. 7B). The presence of CA and IN confined in a closer area could correspond to viral cores in the cytoplasm. Thus, we used electron tomography to obtain. a detailed view of the organization of the state of viral complexes during HIV-1 infection. We infected Hela cells respecting a ratio of 1 million of cells with 500 ng of p24. Thus, we observed that at 2-6 hours post-infection many viruses reside in endo-somes, which are the entry pathway engaged by HIV-1 pseudotyped with VSV-G[22]. VSV-G allows viruses to escape from these cytoplasmic organelles to continue their journey towards the nucleus (FIG. 1c). Many cores have been morphologically identified inside of endosomes and some of them during the release from these organelles. To demonstrate that these are forms of viral CA we labelled sections with a specific antibody against CA, which is recognized by a secondary antibody coupled to 10 nm gold particles giving black dots on EM (FIG. 1c).

At six hours post-infection we also observed that core like structures can join the nuclear envelope (NE). Surprisingly, we noted that these viral CA structures are usually decorated by 2 gold particles (FIG. 2d), even if the viral core is composed by multiple CA monomers[5]. It is possible that the accessibility of the antibody to CA is reduced because few epitopes are exposed on the sections due to the limit space on viral cores or because the target site of the antibody is occupied by cellular factors. These viral complexes are often in crosswise position with respect to interruptions along the NE that should correspond to NPCs, which are the nuclear entry doors used by HIV-1[6]. Cryo-EM on immuno-gold labelled refrozen sections[23] show a divergent CA gold label-ling distribution between cytoplasm and nucleus (FIG. 1e). We were able to observe a remodeling of the viral CA before, during and after nuclear entry. We detected particular structures composed by multiple gold particles forming a "pearl necklace" shape inside the nucleus near the NE (FIG. 1e), detailed by tomogram volume analysis (FIG. 1f). Simi-lar structures have been found with a wild type envelope virus (FIG. 8), suggesting that the reorganization of the gold-labelled complexes do not depend on the route of entry. To further characterize the morphology of HIV-1 complexes in and out the nucleus, we analyzed their relative spatial distribution and density of the different CA structures by labelling CA and IN with different sized of colloidal gold conjugates (6 nm and 10 nm respectively) (FIG. 1g,h).

Statistical analysis of the distribution of the gold labels demonstrates that different CA subtype structures are present throughout the cell volume analyzed. These structures are found in both densely packed, associated or not with IN (FIG. 1e,f,g), and sparsely occupied sub-regions defining a conical core like shape exclusively in the cytoplasm (FIG. 1d,h). Core like shapes are usually detected by 2 gold labelling (FIG. 1d), while viral complexes identified by 3 CA gold particles are the one often associated with IN. The latter are mainly detected inside the nucleus (FIG. 1g,h), strongly suggesting that CA and IN are the major constitu-ents of the PICs. IN is more frequently associated to viral structures containing 3 CA gold rather than 2 CA gold particles, probably because in the first the IN is more exposed due to the relaxed open shape. These results reflect the viral capsid remodeling from a compacted structure versus a relaxed shape, which occurs to gain access to the nucleus.

Example 3: HIV-1 CA Decorates the PIC During Nuclear Translocation

Figure 2:
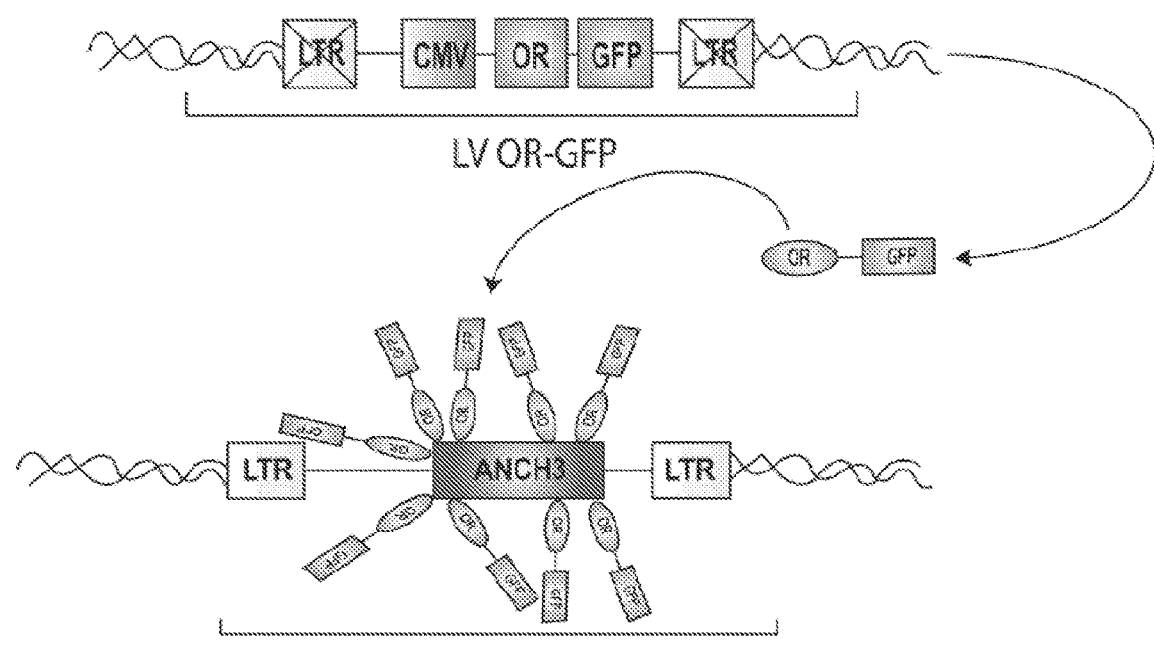
FIG. 2: Detection of the retrotranscribed HIV-1 DNA in infected cells. a) Schema of the HIV-1/ANCHOR system based on lentiviral vectors carrying on the OR-GFP cDNA under the control of CMV promoter (LV OR-GFP) and HIV-1 containing the ANCH3, target sequence of OR pro-tein (HIV-1ΔEnvIN$_{HA}$ΔNef ANCH3/VSV-G). b) HeLa P4R5 cells were transduced with LV OR-GFP. The effi-ciency of OR-GFP expression was monitored by western blotting using antibody against GFP. As a loading control, samples were also blotted using antibody against actin. HeLa cells stably expressing ORGFP infected or not with HIV-1ΔEnvIN$_{HA}$ΔNef ANCH3/VSV-G have been tested by IF at 24 h p.i. c) Comparison of infectivity of HIV-1ΔEnvIN$_{HA}$ΔNef ANCH3/VSV-G using different doses (100 ng, 50 ng and 10 ng of p24) on HeLa P4R5 cells transduced or not with LV OR-GFP by LacZ expression using b-galactosidase assay normalized to the amount of protein. Results were analyzed using two-tailed Student's t test, P value<0.01 (**), <0.1 (*) and nonsignificant (ns).
Figure 2:
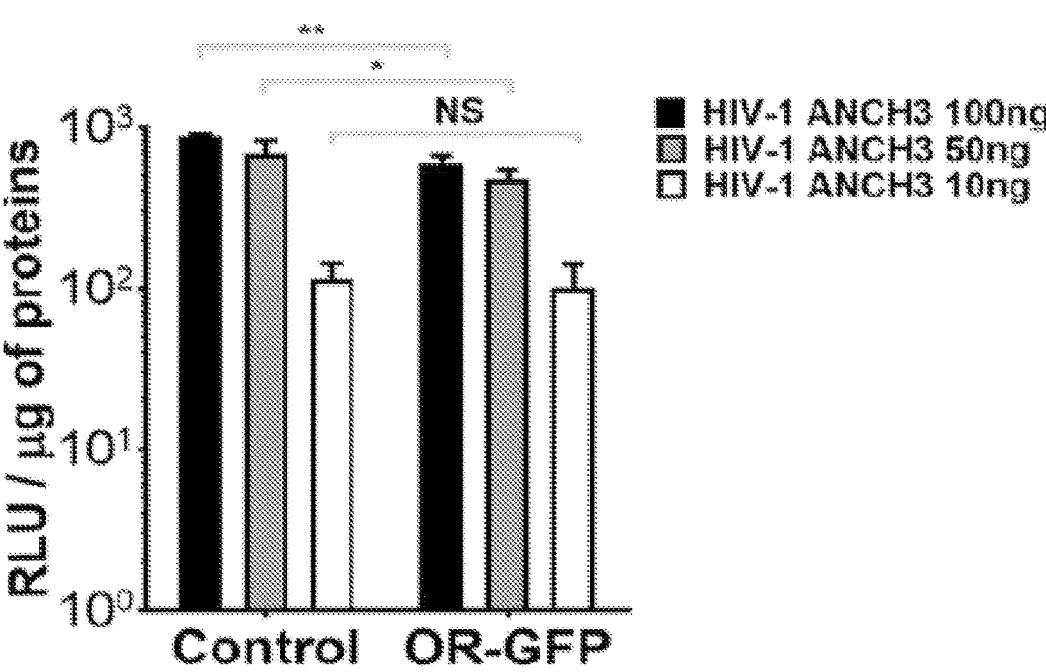
Figure 2:
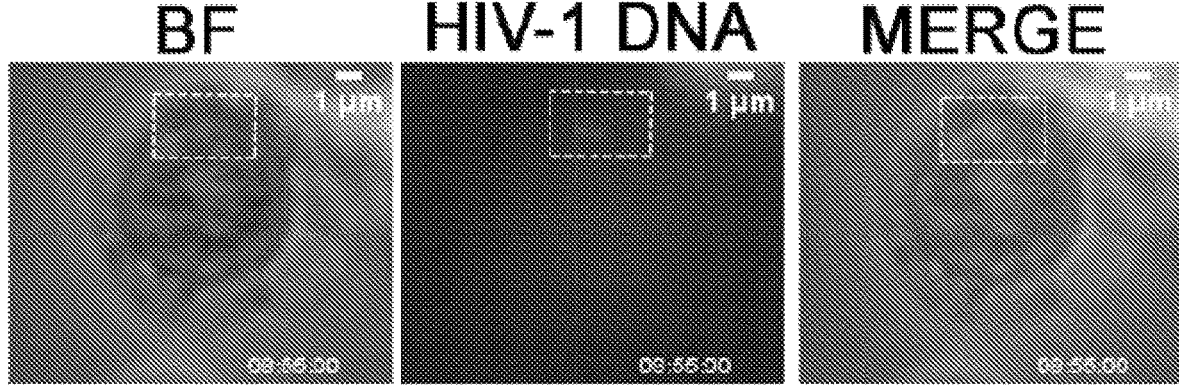

HIV-1 CA has been proposed to be the determinant of the viral nuclear import (Yamashita, Emerman). In our study we observed CA associated to potential PICs during viral nuclear entry. Therefore to investigate if the observed relaxed structures are real PICs, we analyzed whether the retrotranscribed viral genome was present in these com-plexes. Labelling of the retrotranscribed viral DNA has been a big challenge and only partial success has been achieved using DNA FISH or EdU labelling in fixed cells[18,24,25], both incompatible with transmission electron microscopy (TEM) technique. Thus, we set up a new system that allows to directly track the presence of the viral retrotranscribed DNA in the immunogold labelled complexes. Our system that we called HIV-1 ANCHOR is based on the combination of ANCHOR technology (NeoVirtech), previously used to target other viruses[26,27], with lentiviral vector (LV) gene delivery (FIG. 2a). The ANCHOR technology consists in a bipartite system derived from a bacterial parABS chromo-some segregation machinery. This is composed by ANCH3 DNA sequence recognized by OR protein fused to GFP, a modified version of the bacterial parB protein[28,29]. We cloned ANCH3 sequence in HIV-1 genome (HIV-1 ANCH3) to be able to directly label the retrotranscribed viral DNA in a highly specific manner, thanks to the absence of ANCH sequences into the human genome of the host cells. Thus, we infected with this virus Hela cells, previously transduced with a LV carrying on ORGFP cDNA (FIG. 2b). Our immunofluorescence experiments revealed that HIV-1 ANCH3 is recognized by OR-GFP fusion proteins that accumulate on the target sequence resulting in the formation of a bright detectable fluorescent spot. OR-GFP protein misses the nuclear localization sequence and therefore freely diffuses in the cell volume but when the reverse transcription occurs OR-GFP can be efficiently transported in the nucleus in complex with the retrotranscribed viral DNA (FIG. 2b). More importantly. HIV-1 ANCHOR permits—for the first time—to detect in real time viral DNA. This allows to follow the fate of the viral DNA from the reverse transcription step onward. In fact, to validate our system we performed several time-lapse movies on infected OR-GFP Hel a cells. We observed multiples fields of view containing several cells for 70 h post infection, taking a picture every 10 minutes. Then we used a spinning disk microscope to obtain full cellular volumes every 20 seconds of HIV-1 infected cells until 7 h post infection Besides, we also tested whether viral tran-scription could be affected by the presence of ORGFP in the cells. We observed that the viral transcription is only slightly affected at high doses but not at low doses of viruses by the presence of OR-GFP as shown by the beta gal assay, which is based on the expression of lacZ gene, which is stably integrated in the host HeLa P4R5 cells, under the regulation of LTR promoter (FIG. 2c).

Once proved the efficiency and specificity of the HIV-1 ANCHOR system, we investigated whether the viral com-plexes detected by TEM contain the retrotranscribed viral DNA, meaning that these are functional PICs. Importantly, HIV-1 ANCHOR provides an excellent opportunity to investigate the association of the viral DNA with the gold CA complexes described above. To do so we performed correlated light- and electron microscopy (CLEM). Briefly, we infected HeLa cells expressing OR-GFP with HIV-1 ANCH3 for 6 h (the estimated peak on nuclear import of HIV-1) and labelling with antibody against CA protein followed by protein A coupled to gold. Then, we imaged the sections with a fluorescent microscope to detect the DNA spots. Later the same sections were contrasted with uranium acetate and imaged with the TEM. We were able to correlate the fluorescence signal of viral DNA with CA gold labelling as part of the same complex during viral nuclear import event (FIG. 3a). Three gold particles indicate the presence of viral CA proteins that decorate the viral DNA (FIG. 3a). We calculated an error ~73 nm for the superposition of the fluorescent (IF) and high resolution (TEM) images (FIG. 10). This complex has an elongated shape, probably as consequence of the CA remodeling during the passage through the NE. Overall results obtained by TEM and by CLEM highlighted the morphology of PICs containing all required components for the integration, such as the integrase, DNA and surprisingly capsid as well. The presence of consistent shapes formed by multiple CA in the nucleus (FIG. 1d,e) confirms that the capsid has a main role in nuclear import[6,7,30,31] and/or even in the integration step[30,32]. A potential role of CA in integration is corroborated by the fact that the majority of detected complexes are located preferentially (~86%) at less than 2 μM from the NE (FIG. 3b). This is consistent with previous studies that reported a preferential integration of HIV-1 near the NE[6,24,33]. Next, to corroborate the functionality of the viral structures detected by HIV-1 ANCHOR system, we used PF74 drug. It is known that PF74 impedes viral nuclear entry targeting the viral CA and acting with a bimodal mechanism dose-dependent on the DNA synthesis (Price et al., Plos Pathogens, 2014; Buffone et al., 2018, Yamashita et al., JVI). At concentrations lower than 2 μM, PF74 directly competes with the binding of host viral partners, such as cleavage and polyadenylation specific factor 6 (CPSF6) and nucleoporin 153 (NUP153)[30,34-36]. At higher concentrations (~10 μM) PF74 probably accelerates uncoating and blocks reverse transcription[30,34,36]. Therefore, we could use PF74 as a tool to alter the viral infectivity, the DNA synthesis and the nuclear import (FIG. 3c). To this purpose we challenged HeLa cells expressing OR-GFP with HIV-1 ANCH3 for 24 h in presence of low and high dose of PF74. Interestingly, we were able to detect the viral DNA inside the nucleus only in the absence of PF74 (FIG. 3d,e), in agreement with results obtained by infectivity, nuclear import and DNA synthesis assays (FIG. 3c).

In parallel, we performed RNA FISH and immunolabelling against the viral CA and IN, respectively, and measured the number of RNA detections and IN/CA colocalizing spots per cell (FIG. 7d,e). We observed active viral transcription at 24 hours post infection in absence of PF74 (FIG. 7e). In contrast when we applied a low dose of PF74 the association between CA and IN was preserved to levels comparable to samples without drug at 6 h post infection as well the viral RNA of the incoming cores was not completely degraded as it happened in presence of high dose of PF74 (FIG. 7c,d,e). In this last case also the association between CA and IN was lost, suggesting a premature uncoating due to the high dose of PF74 (FIG. 7d, e). Our results revealed that effects on the DNA synthesis and nuclear import of PF74 are related to the loss of CA and IN interactions, which also affects viral RNA stability (FIG. 7d, e).

These observations had a great value for us because they demonstrated that HIV-1 ANCHOR exclusively tracks the nuclear incoming retrotranscribed viral DNA as part of a functional PIC[55] (FIG. 3f).

Example 4: Live-Track of HIV-1 PIC in Infected Cells

The nuclear fate of the HIV-1 DNA has never been visualized before by live imaging. To this purpose we asked whether HIV-1 ANCHOR system could allow us to go further on the nuclear fate of the previously detected PICs. Thus, we investigated by live imaging viral PICs entering in the nucleus as well as the pinpoint of the viral genome with the viral IN by coupling HIV-1/ANCHOR system with GIR virus (generous gift from Edward Campbell)[37,38]. The GIR virus consists in a plasmid expressing Gag-IN-Ruby containing the protease cleavage site between Gag and Integrase complemented with a viral genome carrying on the IN mutated in the catalytic site (HIV-1ΔEnv IN (D116A) ΔNef ANCH3/VSVG). Thus, the only active IN in these viral particles was the IN-Ruby (FIG. 4a). Frequently we observed red spots, most probably IN-Ruby multimers[39,40], which are part of the PIC, going inside the nucleus and few minutes later green spots appeared revealing the location of HIV-1 genome integrated into the host chromosomal DNA (FIG. 4b). Besides, we also observed that the green spots, specifically detecting HIV-1 DNA, were often associated with IN-Ruby signal in the nucleus. When we followed the dynamics of this association we could see how the IN-Ruby signal seemed to remain in the vicinity of DNA-ORGFP spots for at least 3-4 hours (FIG. 4c). The distance measured between the two signals (IN-Ruby/DNA-GFP) was in the range of 0.6-0.8 μm (FIG. 4d). This distance remained constant for almost 3 hours, then a quick change happened and the distance between the two spots drastically reduced to a distance of ~0.1 μm between them for almost 30 minutes (FIG. 4c, FIG. 9a,b). After this period the two spots start to separate again until the complete disappearance of the IN-Ruby signal, which corresponds to a slight increase of the brightness of the DNA-GFP signal (FIG. 4c). Because our infection is not synchronized we observed the association IN-Ruby/DNA-ORGFP even in fixed cells at 24 hours post-infection (FIG. 9c). Our results show a clear appearance of the viral DNA as punctate bright signal in the nucleus. Contrary to the nucleus in the cytoplasm bright individual spots are hardly visualized. Probably because cores or partial cores mainly located in the cytoplasm (FIG. 1d,h) impede the accessibility of OR-GFP to the viral DNA, in fact it is known that CA structures can generate a steric hindrance that protects the viral DNA from some endonucleases (Jacques et al., Nature). According to our data the viral DNA is only partially accessible to the ORGFP when the CA remodels to be able to cross the NE as shown by results obtained by CLEM (FIG. 3a). After viral integration ANCH sites become more exposed to ORGFP proteins as results of the release of PIC components like the IN, giving rise to the brightest green spot (FIG. 4c).

The data presented in the examples provides a detailed view of the structural remodeling of the viral CA prior, during and after viral nuclear entry. In addition the data obtained by live imaging show that the event of integration lasts for more than three hours and that the viral DNA forms a large complex with the IN during the integration step. This study is the first proof of concept of the possibility to directly target the retrotranscribed viral DNA in live cells. HIV-1 ANCHOR is a powerful tool that could reveal new insights into the viral persistence by localizing the latent virus in vivo. Overall our findings give a new outlook not only on the morphology of viral complexes but also on the dynamic and fate of the viral DNA inside the host nucleus, which may pave the way for new therapeutic interventions.

Example 5: Validation of the Specificity of HIV-1 ANCHOR System to Visualize the Viral DNA To pinpoint the specificity of HIV-1 ANCHOR system to detect exclusively HIV-1 DNA, we infected Hel a OR-GFP cells with different MOIs (multiplicity of infection) of HIV-1 ANCH3. We observed a linear correlation between MOI and the number of nuclear vDNA spots in GFP+ infected cells (Pearson's coefficient ~1) (FIG. 11A). The total number of intranuclear spots analysed for each condition was 2054 counts for 34 GFP+ infected cells (MOI 200), 393 counts for 38 GFP+ cells (MOI 30), 290 counts for 44 GFP+ cells (MOI 10). Averages (Avg) of nuclear spots were calculated for single condition (MOI 10 Avg 6.7; MOI 30 Avg 10.07; MOI 200 Avg 60.4) (FIG. 11A). In addition, we infected cells in the presence of drugs, PF74 or nevirapine (NEV, inhibitor of RT). First we challenged HeLa cells expressing OR-GFP with HIV-1 ANCH3 for 24 h without drug or in the presence of low and high doses of PF74 (FIG. 11B). Both doses of PF74 blocked viral nuclear entry. We detected the viral DNA inside the nucleus mainly in the absence of PF74, in agreement with nuclear import data obtained by qPCR (FIG. 11B). Total intranuclear spots were analysed for each condition (no drugs 180 spots in 13 GFP+ cells; PF74 low dose 8 spots in 28 GFP+ cells; PF74 high dose 1 spot in 27 GFP+ cells) (FIG. 11B). These results were confirmed also when the nevirapine was used. We counted intranuclear spots in 20 cells per condition and we obtained the following results: 152 nuclear spots in absence of NEV against 0 detections in presence of the drug. Thus, nuclear punctae containing HIV-1 DNA were found only in NEV untreated cells (FIG. 11E). Overall, these observations demonstrated that HIV-1 ANCHOR technology faithfully tracked the retrotranscribed viral DNA.

Example 6: HIV-1 ANCHOR Allows the Identification of HIV-1 PIC in the Nucleus of Infected Cells Using Immunogold Labeling Coupled to EM A dual gold labelling experiment has been performed to detect viral complexes in the nucleus. Different size of gold particles have been used to label the viral DNA through OR-GFP (anti-GFP, 5 nm gold) and the viral CA (10 nm gold). Interestingly multiple gold particles labelling the viral DNA (5 nm) associated with CA (10 nm) adopting a linear configuration at the NE (FIG. 12) have been detected. This morphology corroborated the form of the PIC detected by CIEM (FIG. 3). Complexes formed by the viral DNA associated to HIV-1 CA in the nucleus of infected dividing cells (FIG. 12) have been revealed. These data are in line with our CLEM results, showing that viral complexes containing the retrotranscribed DNA can retain several CA proteins even after nuclear translocation.

Overall results obtained by TEM and by CLEM highlighted the shape of a potential HIV-1 PIC during and after the nuclear entry step. Importantly the detected viral complexes contain all required components for the integration, such as the integrase, DNA and, surprisingly, multiple CA proteins.

Example 7. HIV-1 ANCHOR Versatile Tool to Detect Integrated or Episomal Forms in Cell Lines or Primary Cells A stable HeLa clone carrying a HIV genome ANCH3 tagged has been selected and analyzed by fluorescence microscopy and qPCR. FIG. 13A shows a tight correlation between the results obtained with both techniques, indicating that HIV-1 ANCHOR has a high sensitivity to visualize a single provirus. HIV-1 ANCHOR can also detect unintegrated viral nuclear forms as shown by the fluorescence images performed on HeLa OR-GFP cells infected in presence of Raltegravir (inhibitor of the integration step) or using a virus integration deficient (HIV-1 ANCHOR $IN_{D116A}$). HIV-1 ANCHOR is a versatile system and can be applied to visualize viral DNA in macrophages and CD4+ T cells, both cells are transduced with LV OR-GFP before infection (FIG. 13B). Importantly HIV-1 ANCHOR does not affect the interplay between HIV-1 PIC with important host and viral factors for the integration step which is essential for viral replication. In fact, FIG. 13C shows a colocalization by IF between vDNA (ANCHOR), CPSF6 (host factors important for nuclear entry and integration step) and IN (viral protein responsible for the integration of the viral DNA into the host chromatin). These data have been obtained in the major target cell for HIV-1, primary CD4+ T cells (FIG. 13C).

Example 8. HIV-1 ANCHOR Allows to Follow the Fate of HIV-1 Genomes

HeLa and Jurkat cells have been transduced with a LVOR-GFP and then infected with HIV-1 ANCH3 at an MOI of 30. RNA FISH coupled to HIV-1 ANCHOR has been performed to detect nuclear viral forms transcribing (green spots, vDNA, co-localizing with red spots, vRNA) or not. RNA FISH has been performed using probes listed in table 1. Viral RNA foci of transcription can be also followed by live imaging as shown in FIG. 14C. We were able to follow vRNA foci in Hela cells and primary CD4 T cells after transduction with a LV carrying MCP that binds MS2 sequence which it has been cloned in HIV-1 genome together with ANCH3. This system will allow to follow in live cells viruses transcriptionally active or not (FIG. 14b).

Example 9. HIV-1 ANCHOR for Study on Viral Persistence or for an In Vivo Model for Gene Therapy Based on Lentiviral Vectors A HIV-1 strain (NL4.3 ires GFP) has been modified by cloning ANCH3 sequence at the place of ires GFP using the restriction enzymes MluI and XmaI. We obtained a replicative efficient tagged virus as shown by the comparison of viral fitness in T cells (SupT1 cells) (FIG. 15). This virus will allow to perform study on infected humanized mice. A strain NL4.3/AD8 tagged with ANCH3 has been generated (NL4.3/AD8 ANCH3, FIG. 18). To clone Env and other neighboring sequences from pNL4.3/AD8 in pNL4.3 Nef ANCH3 AgeI and HpaI restriction enzymes have been used.

Example 10. Single Cell Live Imaging for a Fast and Efficient Drug Screening Against SARS-CoV2

Lentiviral particles composed by a transfer vector pFlap ANCH3 (400 nt or 1 Kb), delta R8.74 coding for gag pol and the envelope Spike derived from SARS-CoV2. The three plasmids are co-transfected in 293T cells to produce lentiviral particles pseudotyped with Spike (S-LV-ANCH3). The S-LV-ANCH3 can be concentrated by ultracentrifugation or not (FIG. 16*a*) 293T genetically modified by (LV ACE2), highly express angiotensin-converting enzyme 2 (ACE2, NCBI reference NG_012575), the receptor for SARS-CoV2, are transduced with S-LV-ANCH3. Twenty four hours after transduction cells were analyzed by fluorescence microscopy. Bright nuclear spots were detected only in transduced cells, indicating the success of the infection (FIG. 16*b*). This is a single cell useful for live drug screening to test several library of compounds already approved by the FDA or in clinical trials or to test completely new molecules derived from smart drug design able to interfere with the interaction between the cellular receptor (ACE2) and the spike, viral protein used to generate S-LV-ANCH3. We validated the system using hydroxychloquine which inhibit viral entry of S-LV-ANCH3, most probably acting in an indirect fashion. Chloroquine and its safer derivate HCQ, may reduce glycosylation of ACE2, thereby preventing COVID-19 from effectively binding to host cells (Devaux, C. A., et al., 2020. New insights on the antiviral effects of chloroquine against coronavirus: what to expect for COVID-19?. International Journal of Antimicrobial Agents.) Some viruses enter host cells through endocytosis; the virus is transported within the host cell in a cell-membrane derived vesicle called an endosome, within which the virus can replicate (Savarino, A., et al., 2003. Effects of chloroquine on viral infections: an old drug against today's diseases. The Lancet infectious diseases). When the endosome fuses with the acidic intracellular lysosome, this leads to rupture of the endosome with the release of the viral contents (Savarino, A., et al., 2003. Effects of chloroquine on viral infections: an old drug against today's diseases. The Lancet infectious diseases). Chloroquine has been found to accumulate in lysosomes, interfering with this process (Golden E B, et al., Quinoline-based antimalarial drugs: a novel class of autophagy inhibitors. Neurosurg Focus. 2015). Chloroquine is also believed to raise the pH level of the endosome, which may interfere with virus entry and/or exit from host cells (Vincent, M. J., et al., 2005. Chloroquine is a potent inhibitor of SARS coronavirus infection and spread. Virology journal). However HCQ has been highly debated for its efficacy in humans and it remains a drug that acts in an indirect way on the viral replication. So the finding of new safer and more efficient drugs against Covid 19 is becoming extremely urgent.

The advantages of the system are the following:

Single cell screening in live or fixed cells (easy detection of toxicity, direct effect of the drug on the interested infected cell).

Rapid results within 24 h post infection. The peak of reverse transcription is ~6 h post infection so since 6 h post infection the transduced cells can be analyzed.

BSL2 system

The results are independent of the level of viral transcription in the target cells, which is the case for other reporters like GFP or Luc.

To our knowledge this is the first BSL2 single cell live imaging system to screen compounds based on the detection of the viral genome

| TABLE OF LISTED SEQUENCES | | |
| --- | --- | --- |
| SEQ ID | DESCRIPTION | Type of sequence |
| 1-8 | ANCH3 MOTIF | Nucleic acid |
| 9-32 | Probes | Nucleic acid |
| 33 | ParB | Amino acid |

REFERENCES

1. Coffin, J. M., Hughes, S. H. & Varmus, H. E. in Retroviruses (eds J. M. Coffin, S. H. Hughes, & H. E. Varmus) (1997).

2 Lusic, M. & Siliciano, R. F. Nuclear landscape of HIV-1 infection and integration. Nature reviews. Microbiology 15, 69-82, doi: 10.1038/nrmicro.2016.162 (2017).

3. McDonald, D. et al. Visualization of the intracellular behavior of HIV in living cells. The Journal of cell biology 159, 441-452, doi: 10.1083/jcb.200203150 (2002).

4. Campbell, E. M. & Hope, T. J. HIV-1 capsid: the multifaceted key player in HIV-1 infection. Nature reviews. Microbiology 13, 471-483, doi: 10.1038/nrmicro3503 (2015).

5. Pornillos, O., Ganser-Pornillos, B. K. & Yeager, M. Atomic-level modelling of the HIV capsid. Nature 469, 424-427, doi: 10.1038/nature09640 (2011).

6. Lelek, M. et al. Chromatin organization at the nuclear pore favours HIV replication. Nat Commun 6, 6483, doi: 10.1038/ncomms7483 (2015).

7. Di Nunzio, F. et al. Nup153 and Nup98 bind the HIV-1 core and contribute to the early steps of HIV-1 replication. Virology 440, 8-18, doi: 10.1016/j.virol.2013.02.008 (2013).

8. Di Nunzio, F. et al. Human nucleoporins promote HIV-1 docking at the nuclear pore, nuclear import and integration. PloS one 7, e46037, doi: 10.1371/journal.pone.0046037 (2012).

9 Matreyek, K. A., Yucel, S. S., Li, X. & Engelman, A. Nucleoporin NUP153 phenylalanine-glycine motifs engage a common binding pocket within the HIV-1 capsid protein to mediate lentiviral infectivity. PLOS pathogens 9, e1003693, doi: 10.1371/journal.ppat. 1003693 (2013).

10. Schaller, T. et al. HIV-1 capsid-cyclophilin interactions determine nuclear import pathway, integration targeting and replication efficiency. PLOS pathogens 7, e1002439, doi: 10.1371/journal.ppat. 1002439 (2011).

11. Lee, K. et al. Flexible use of nuclear import pathways by HIV-1. Cell host & microbe 7, 221-233, doi: 10.1016/j.chom.2010.02.007 (2010).

12. Lelek, M. et al. Superresolution imaging of HIV in infected cells with FLASH-PALM. Proceedings of the National Academy of Sciences of the United States of America 109, 8564-8569, doi: 10.1073/pnas. 1013267109 (2012).

13. Francis, A. C. & Melikyan, G. B. Single HIV-1 Imaging Reveals Progression of Infection through CA-Dependent Steps of Docking at the Nuclear Pore, Uncoating, and Nuclear Transport. Cell host & microbe 23, 536-548 e536, doi: 10.1016/j.chom.2018.03.009 (2018).

14. Francis, A. C., Marin, M., Shi, J., Aiken, C. & Melikyan, G. B. Time-Resolved Imaging of Single HIV-1 Uncoating In Vitro and in Living Cells. PLOS pathogens 12, e1005709, doi: 10.1371/journal.ppat. 1005709 (2016).

15. Burdick, R. C. et al. Dynamics and regulation of nuclear import and nuclear movements of HIV-1 complexes. PLOS pathogens 13, e1006570, doi: 10.1371/journal.ppat. 1006570 (2017).

16. Hulme, A. E., Perez, O. & Hope, T. J. Complementary assays reveal a relationship between HIV-1 uncoating and reverse transcription. Proceedings of the National Academy of Sciences of the United States of America 108, 9975-9980, doi: 10.1073/pnas. 1014522108 (2011).

17. Mamede, J. I., Cianci, G. C., Anderson, M. R. & Hope, T. J. Early cytoplasmic uncoating is associated with infectivity of HIV-1. Proceedings of the National Academy of Sciences of the United States of America 114, E7169-E7178, doi: 10.1073/pnas. 1706245114 (2017).

18. Peng, K. et al. Quantitative microscopy of functional HIV post-entry complexes reveals association of replication with the viral capsid. Elife 3, e04114, doi: 10.7554/eLife.04114 (2014).

19. Berry, F. et al. [Host nuclear pore factors: team players of HIV-1 nuclear translocation and integration]. Med Sci (Paris) 34, 512-515, doi: 10.1051/medsci/20183406006 (2018).

20. Miller, M. D., Farnet, C. M. & Bushman, F. D. Human immunodeficiency virus type 1 preintegration complexes: studies of organization and composition. Journal of virology 71, 5382-5390 (1997).

21. Petit, C., Schwartz, O. & Mammano, F. The karyophilic properties of human immunodeficiency virus type 1 integrase are not required for nuclear import of proviral DNA. Journal of virology 74, 7119-7126 (2000).

22. Aiken, C. Pseudotyping human immunodeficiency virus type 1 (HIV-1) by the glycoprotein of vesicular stomatitis virus targets HIV-1 entry to an endocytic pathway and suppresses both the requirement for Nef and the sensitivity to cyclosporin A. Journal of virology 71, 5871-5877 (1997).

23. Bos, E. et al. Vitrification of Tokuyasu-style immuno-labelled sections for correlative cryo light microscopy and cryo electron tomography. Journal of structural biology 186, 273-282, doi: 10.1016/j.jsb.2014.03.021 (2014).

24. Marini, B. et al. Nuclear architecture dictates HIV-1 integration site selection. Nature 521, 227-231, doi: 10.1038/nature14226 (2015).

25. Stultz, R. D., Cenker, J. J. & McDonald, D. Imaging HIV-1 Genomic DNA from Entry through Productive Infection. Journal of virology 91, doi: 10.1128/JVI.00034-17 (2017).

26. Komatsu, T. et al. In vivo labelling of adenovirus DNA identifies chromatin anchoring and biphasic genome replication. Journal of virology, doi: 10.1128/JVI.00795-18 (2018).

27. Mariame, B. et al. Real-time visualization and quantification of human Cytomegalovirus replication in living cells using the ANCHOR DNA labeling technology. Journal of virology, doi: 10.1128/JVI.00571-18 (2018).

28. Graham, T. G. et al. ParB spreading requires DNA bridging. Genes & development 28, 1228-1238, doi: 10.1101/gad.242206.114 (2014).

29. Sanchez, A. et al. Stochastic Self-Assembly of ParB Proteins Builds the Bacterial DNA Segregation Cell Syst Apparatus. 1, 163-173, doi: 10.1016/j.cels.2015.07.013 (2015).

30. Buffone, C. et al. Nup153 Unlocks the Nuclear Pore Complex for HIV-1 Nuclear Translocation in Nondividing Cells. Journal of virology 92, doi: 10.1128/JVI.00648-18 (2018).

31. Chen, N. Y. et al. HIV-1 capsid is involved in post-nuclear entry steps. Retrovirology 13, 28, doi: 10.1186/s12977-016-0262-0 (2016).

32. Sowd, G. A. et al. A critical role for alternative polyadenylation factor CPSF6 in targeting HIV-1 integration to transcriptionally active chromatin. Proceedings of the National Academy of Sciences of the United States of America 113, E1054-1063, doi: 10.1073/pnas.1524213113 (2016).

33. Di Primio, C. et al. Single-cell imaging of HIV-1 provirus (SCIP). Proceedings of the National Academy of Sciences of the United States of America 110, 5636-5641, doi: 10.1073/pnas. 1216254110 (2013).

34. Saito, A. et al. Roles of Capsid-Interacting Host Factors in Multimodal Inhibition of HIV-1 by PF74. Journal of virology 90, 5808-5823, doi: 10.1128/JVI.03116-15 (2016).

35. Price, A. J. et al. CPSF6 defines a conserved capsid interface that modulates HIV-1 replication. PLOS pathogens 8, e1002896, doi: 10.1371/journal.ppat. 1002896 (2012).

36. Price, A. J. et al. Host cofactors and pharmacologic ligands share an essential interface in HIV-1 capsid that is lost upon disassembly. PLOS pathogens 10, e1004459, doi: 10.1371/journal.ppat. 1004459 (2014).

37. Hulme, A. E., Kelley, Z., Foley, D. & Hope, T. J. Complementary Assays Reveal a Low Level of CA Associated with Viral Complexes in the Nuclei of HIV-1-Infected Cells. Journal of virology 89, 5350-5361, doi: 10.1128/JVI.00476-15 (2015).

38. Dharan, A. et al. KIF5B and Nup358 Cooperatively Mediate the Nuclear Import HIV-1 during Infection. PLOS pathogens 12, e1005700, doi: 10.1371/journal.ppat. 1005700 (2016).

39. Ballandras-Colas, A. et al. A supramolecular assembly mediates lentiviral DNA integration. Science 355, 93-95, doi: 10.1126/science.aah7002 (2017).

40. Passos, D. O. et al. Cryo-EM structures and atomic model of the HIV-1 strand transfer complex intasome. Science 355, 89-92, doi: 10.1126/science.aah5163 (2017).

41. Charneau, P. et al. HIV-1 reverse transcription. A termination step at the center of the genome. Journal of molecular biology 241, 651-662, doi: 10.1006/jmbi.1994.1542 (1994).

42. Mueller, F. et al. FISH-quant: automatic counting of transcripts in 3D FISH images. Nature methods 10, 277-278, doi: 10.1038/nmeth.2406 (2013).

43. Tsanov, N. et al. smiFISH and FISH-quant—a flexible single RNA detection approach with super-resolution capability. Nucleic acids research 44, e165, doi: 10.1093/nar/gkw784 (2016).

44. Munch, J. et al. Semen-derived amyloid fibrils drastically enhance HIV infection. Cell 131, 1059-1071, doi: 10.1016/j.cell.2007.10.014 (2007).

45. Yolamanova, M. et al. Peptide nanofibrils boost retroviral gene transfer and provide a rapid means for concentrating viruses. Nat Nanotechnol 8, 130-136, doi: 10.1038/nnano.2012.248 (2013).

46. Slot, J. W. & Geuze, H. J. Cryosectioning and immunolabeling. Nature protocols 2, 2480-2491, doi: 10.1038/nprot.2007.365 (2007).

47. Mastronarde, D. N. Automated electron microscope tomography using robust prediction of specimen movements. Journal of structural biology 152, 36-51, doi: 10.1016/j.jsb.2005.07.007 (2005).

48. Kremer, J. R., Mastronarde, D. N. & McIntosh, J. R. Computer visualization of three-dimensional image data using IMOD. Journal of structural biology 116, 71-76, doi: 10.1006/jsbi.1996.0013 (1996).

49. Forster, B., Van De Ville, D., Berent, J., Sage, D. & Unser, M. Complex wavelets for extended depth-of-field: a new method for the fusion of multichannel microscopy images. Microscopy research and technique 65, 33-42, doi: 10.1002/jemt.20092 (2004).

50. Thevenaz, P. & Unser, M. User-friendly semiautomated assembly of accurate image mosaics in microscopy. *Microscopy research and technique* 70, 135-146, doi: 10.1002/jemt.20393 (2007).

51. Paul-Gilloteaux, P. et al. eC-CLEM: flexible multidimensional registration software for correlative microscopies. Nature methods 14, 102-103, doi: 10.1038/nmeth.4170 (2017).

52. de Chaumont, F. et al. Icy: an open bioimage informatics platform for extended reproducible research. Nature methods 9, 690-696, doi: 10.1038/nmeth.2075 (2012).

53. Butler, S. L., Hansen, M. S. & Bushman, F. D. A quantitative assay for HIV DNA integration in vivo. Nature medicine 7, 631-634, doi: 10.1038/87979 (2001).

54. Ruelas D S, Greene WC. An integrated overview of HIV-1 latency. Cell. 2013 Oct. 24; 155 (3): 519-29

55. Blanco-Rodriguez G., et al., Remodeling of the core leads HIV-1 pre-integration complex in the nucleus of human lymphocytes. 2020 Apr. 1 J Virol doi: 10.1128/JVI.00135-20

I claim:

1. A recombinant lentiviral vector comprising a coding sequence for an OR protein fused to a coding sequence for a fluorescent protein or a subunit of a fluorescent protein, and a promoter active in human cells operatively linked to the coding sequences.

2. The recombinant lentiviral vector of claim 1, wherein the coding sequence for the OR protein is fused to a coding sequence for green fluorescent protein (GFP).

3. The recombinant lentiviral vector of claim 1, wherein the promoter is the cytomegalovirus (CMV) promoter.

4. The recombinant lentiviral vector of claim 1, wherein the vector further comprises the coding sequence for MS2 coat protein (MCP) fused to a coding sequence for a fluorescent protein or a subunit of a fluorescent protein, and a promoter active in human cells operatively linked to the coding sequences.

5. The recombinant lentiviral vector of claim 1, wherein the vector comprises a 5'-LTR and a 3'-LTR.

6. The recombinant lentiviral vector of claim 1, wherein the vector comprises a central polypurine tract (cPPT)/central termination sequence (CTS).

7. The recombinant lentiviral vector of claim 1, wherein the vector is an HIV-1 vector.

8. A recombinant lentivirus or retrovirus comprising a recombinant genome comprising an RNA that generates an ANCH sequence upon retrotranscription.

9. The recombinant lentivirus or retrovirus of claim 8, wherein the ANCH sequence is an ANCH3 sequence.

10. A recombinant eukaryotic cell comprising a genomically integrated DNA copy of the recombinant lentiviral vector according to claim 1.

11. The recombinant eukaryotic cell of claim 10, further comprising the recombinant genome of a recombinant lentivirus or retrovirus comprising a recombinant genome comprising an RNA that generates an ANCH sequence upon retrotranscription.

12. A method of observing lentiviral or retroviral DNA in a eukaryotic cell, comprising:

providing a recombinant eukaryotic cell that produces a fusion protein comprising an OR protein, fused to a fluorescent protein or a subunit of a fluorescent protein;

infecting the recombinant eukaryotic cell with a recombinant lentivirus or retrovirus comprising a recombinant genome comprising an RNA that generates an ANCH sequence upon retrotranscription, under conditions sufficient for reverse transcription of the recombinant lentiviral or retroviral genome comprising an ANCH sequence;

allowing the OR protein to bind to the ANCH sequence;

and detecting the fluorescent protein or subunit of the fluorescent protein to thereby observe the lentiviral or retroviral DNA in the eukaryotic cell.

13. The method of claim 12, further comprising making the recombinant eukaryotic cell that produces a fusion protein comprising an OR protein, fused to a fluorescent protein or a subunit of a fluorescent protein, by a method comprising transducing a eukaryotic cell with a lentiviral vector comprising a coding sequence for the fusion protein comprising an OR protein, fused to a fluorescent protein or a subunit of a fluorescent protein, and a promoter active in human cells operatively linked to the coding sequences.

14. A method of characterizing an agent that interferes with lentiviral or retroviral nuclear translocation and/or integration, comprising performing a method according to claim 12 in the presence of an agent and determining whether the agent interferes with lentiviral or retroviral nuclear translocation and/or integration.

15. A kit comprising a recombinant lentiviral vector according to claim 1, in combination with a recombinant lentivirus or retrovirus comprising a recombinant genome comprising an RNA that generates an ANCH sequence upon retrotranscription.

16. A method for screening in vitro or ex vivo agents potentially interfering with the penetration of a recombinant retrovirus, comprising detecting in a recombinant eukaryotic cell according to claim 10, viral DNA retrotranscribed from a recombinant retrovirus comprising a recombinant genome comprising an RNA that generates an ANCH sequence upon retrotranscription.

17. A kit comprising a recombinant eukaryotic cell according to claim 10, in combination with a recombinant lentivirus or retrovirus comprising a recombinant genome comprising an RNA that generates an ANCH sequence upon retrotranscription.

18. A method for screening in vitro or ex vivo agents potentially interfering with the penetration of a recombinant retrovirus, comprising detecting in an eukaryotic cell transitionally transformed with a recombinant lentiviral vector according to claim 1, viral DNA retrotranscribed from a recombinant retrovirus comprising a recombinant genome comprising an RNA that generates an ANCH sequence upon retrotranscription.

* * * * *

SEQUENCE LISTING

```
<160> NUMBER OF SEQ ID NOS: 33

<210> SEQ ID NO 1
<211> LENGTH: 14
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (1)..(6)
<223> OTHER INFORMATION: n is a, t, g or c
<220> FEATURE:
<221> NAME/KEY: misc_feature
<222> LOCATION: (9)..(14)
<223> OTHER INFORMATION: n is a, t, g or c

<400> SEQUENCE: 1
nnnnnncgnn nnnn                                                      14

<210> SEQ ID NO 2
<211> LENGTH: 16
<212> TYPE: DNA
<213> ORGANISM: artificial
<220> FEATURE:
<223> OTHER INFORMATION: consensus
<220> FEATURE:
<221> NAME/KEY: misc_feature
<222> LOCATION: (1)..(2)
<223> OTHER INFORMATION: n is a, g, c or t
<220> FEATURE:
<221> NAME/KEY: misc_feature
<222> LOCATION: (4)..(7)
<223> OTHER INFORMATION: n is a, g, c or t
<220> FEATURE:
<221> NAME/KEY: misc_feature
<222> LOCATION: (10)..(13)
<223> OTHER INFORMATION: n is a, g, c or t
<220> FEATURE:
<221> NAME/KEY: misc_feature
<222> LOCATION: (15)..(16)
<223> OTHER INFORMATION: n is a, g, c or t

<400> SEQUENCE: 2
nntnnnncgn nnnann                                                    16

<210> SEQ ID NO 3
<211> LENGTH: 16
<212> TYPE: DNA
<213> ORGANISM: artificial
<220> FEATURE:
<223> OTHER INFORMATION: consensus
<220> FEATURE:
```

```
<221> NAME/KEY: misc_feature
<222> LOCATION: (1)..(1)
<223> OTHER INFORMATION: n is g, c or t
<220> FEATURE:
<221> NAME/KEY: misc_feature
<222> LOCATION: (4)..(4)
<223> OTHER INFORMATION: n is t or g
<220> FEATURE:
<221> NAME/KEY: misc_feature
<222> LOCATION: (5)..(5)
<223> OTHER INFORMATION: n is a or t
<220> FEATURE:
<221> NAME/KEY: misc_feature
<222> LOCATION: (6)..(6)
<223> OTHER INFORMATION: n is t or c
<220> FEATURE:
<221> NAME/KEY: misc_feature
<222> LOCATION: (7)..(7)
<223> OTHER INFORMATION: n is g or a
<220> FEATURE:
<221> NAME/KEY: misc_feature
<222> LOCATION: (10)..(10)
<223> OTHER INFORMATION: n is t or c
<220> FEATURE:
<221> NAME/KEY: misc_feature
<222> LOCATION: (11)..(11)
<223> OTHER INFORMATION: n is g or a
<220> FEATURE:
<221> NAME/KEY: misc_feature
<222> LOCATION: (12)..(12)
<223> OTHER INFORMATION: n is a or t
<220> FEATURE:
<221> NAME/KEY: misc_feature
<222> LOCATION: (13)..(13)
<223> OTHER INFORMATION: n is a or c

<400> SEQUENCE: 3
nttnnnncgn nnnaac                                                    16

<210> SEQ ID NO 4
<211> LENGTH: 16
<212> TYPE: DNA
<213> ORGANISM: artificial
<220> FEATURE:
<223> OTHER INFORMATION: ANCH motif

<400> SEQUENCE: 4
gtttatgcgc ataaac                                                    16

<210> SEQ ID NO 5
<211> LENGTH: 16
<212> TYPE: DNA
<213> ORGANISM: artificial
<220> FEATURE:
<223> OTHER INFORMATION: ANCH motif

<400> SEQUENCE: 5
ctttatgcgc ataaac                                                    16

<210> SEQ ID NO 6
<211> LENGTH: 16
<212> TYPE: DNA
<213> ORGANISM: artificial
<220> FEATURE:
<223> OTHER INFORMATION: ANCH motif

<400> SEQUENCE: 6
gttgtcacgt gacaac                                                    16

<210> SEQ ID NO 7
<211> LENGTH: 16
```

-continued

```
<212> TYPE: DNA
<213> ORGANISM: artificial
<220> FEATURE:
<223> OTHER INFORMATION: ANCH motif

<400> SEQUENCE: 7
tttgtcacgt gacaac                                                          16

<210> SEQ ID NO 8
<211> LENGTH: 16
<212> TYPE: DNA
<213> ORGANISM: artificial
<220> FEATURE:
<223> OTHER INFORMATION: ANCH motif

<400> SEQUENCE: 8
cttgtcacgt gacaac                                                          16

<210> SEQ ID NO 9
<211> LENGTH: 59
<212> TYPE: DNA
<213> ORGANISM: artificial
<220> FEATURE:
<223> OTHER INFORMATION: probe

<400> SEQUENCE: 9
ggggattgta gggaattcca aattcctgct tttacactcg gacctcgtcg acatgcatt        59

<210> SEQ ID NO 10
<211> LENGTH: 58
<212> TYPE: DNA
<213> ORGANISM: artificial
<220> FEATURE:
<223> OTHER INFORMATION: probe

<400> SEQUENCE: 10
cttttagctg acatttatca cagctggcta ttacactcgg acctcgtcga catgcatt         58

<210> SEQ ID NO 11
<211> LENGTH: 55
<212> TYPE: DNA
<213> ORGANISM: artificial
<220> FEATURE:
<223> OTHER INFORMATION: probe

<400> SEQUENCE: 11
gtgtgctggt acccatgcca gatagactta cactcggacc tcgtcgacat gcatt            55

<210> SEQ ID NO 12
<211> LENGTH: 60
<212> TYPE: DNA
<213> ORGANISM: artificial
<220> FEATURE:
<223> OTHER INFORMATION: probe

<400> SEQUENCE: 12
aatactggag tattgtatgg attttcaggc ccttacactc ggacctcgtc gacatgcatt       60

<210> SEQ ID NO 13
<211> LENGTH: 60
<212> TYPE: DNA
<213> ORGANISM: artificial
<220> FEATURE:
<223> OTHER INFORMATION: probe

<400> SEQUENCE: 13
```

-continued

```
ttttactggt acagtctcaa tagggctaat ggttacactc ggacctcgtc gacatgcatt        60

<210> SEQ ID NO 14
<211> LENGTH: 60
<212> TYPE: DNA
<213> ORGANISM: artificial
<220> FEATURE:
<223> OTHER INFORMATION: probe

<400> SEQUENCE: 14
tatgttgaca ggtgtaggtc ctactaatac tgttacactc ggacctcgtc gacatgcatt        60

<210> SEQ ID NO 15
<211> LENGTH: 54
<212> TYPE: DNA
<213> ORGANISM: artificial
<220> FEATURE:
<223> OTHER INFORMATION: probe

<400> SEQUENCE: 15
ctaatcctca tcctgtctac ttgccattac actcggacct cgtcgacatg catt             54

<210> SEQ ID NO 16
<211> LENGTH: 56
<212> TYPE: DNA
<213> ORGANISM: artificial
<220> FEATURE:
<223> OTHER INFORMATION: probe

<400> SEQUENCE: 16
caatcatcac ctgccatctg ttttccattt acactcggac ctcgtcgaca tgcatt           56

<210> SEQ ID NO 17
<211> LENGTH: 58
<212> TYPE: DNA
<213> ORGANISM: artificial
<220> FEATURE:
<223> OTHER INFORMATION: probe

<400> SEQUENCE: 17
tttccaaagt ggatttctgc tgtccctgta ttacactcgg acctcgtcga catgcatt         58

<210> SEQ ID NO 18
<211> LENGTH: 59
<212> TYPE: DNA
<213> ORGANISM: artificial
<220> FEATURE:
<223> OTHER INFORMATION: probe

<400> SEQUENCE: 18
ttgtggatga atactgccat ttgtactgct gttacactcg gacctcgtcg acatgcatt        59

<210> SEQ ID NO 19
<211> LENGTH: 58
<212> TYPE: DNA
<213> ORGANISM: artificial
<220> FEATURE:
<223> OTHER INFORMATION: probe

<400> SEQUENCE: 19
ttaagatgtt cagcctgatc tcttacctgt ttacactcgg acctcgtcga catgcatt         58

<210> SEQ ID NO 20
<211> LENGTH: 56
<212> TYPE: DNA
<213> ORGANISM: artificial
```

<220> FEATURE:
<223> OTHER INFORMATION: probe

<400> SEQUENCE: 20
tacagtctac ttgtccatgc atggcttctt acactcggac ctcgtcgaca tgcatt         56

<210> SEQ ID NO 21
<211> LENGTH: 57
<212> TYPE: DNA
<213> ORGANISM: artificial
<220> FEATURE:
<223> OTHER INFORMATION: probe

<400> SEQUENCE: 21
tcatgttcat cttgggcctt atctattcct tacactcgga cctcgtcgac atgcatt        57

<210> SEQ ID NO 22
<211> LENGTH: 60
<212> TYPE: DNA
<213> ORGANISM: artificial
<220> FEATURE:
<223> OTHER INFORMATION: probe

<400> SEQUENCE: 22
tgtcagttag ggtgacaact ttttgtcttc ctttacactc ggacctcgtc gacatgcatt     60

<210> SEQ ID NO 23
<211> LENGTH: 57
<212> TYPE: DNA
<213> ORGANISM: artificial
<220> FEATURE:
<223> OTHER INFORMATION: probe

<400> SEQUENCE: 23
tgctcctact atgggttctt tctctaactt tacactcgga cctcgtcgac atgcatt        57

<210> SEQ ID NO 24
<211> LENGTH: 60
<212> TYPE: DNA
<213> ORGANISM: artificial
<220> FEATURE:
<223> OTHER INFORMATION: probe

<400> SEQUENCE: 24
tctgttagtg ctttggttcc tctaaggagt ttttacactc ggacctcgtc gacatgcatt     60

<210> SEQ ID NO 25
<211> LENGTH: 59
<212> TYPE: DNA
<213> ORGANISM: artificial
<220> FEATURE:
<223> OTHER INFORMATION: probe

<400> SEQUENCE: 25
ctgtatgtca ttgacagtcc agctgtcttt tttacactcg gacctcgtcg acatgcatt      59

<210> SEQ ID NO 26
<211> LENGTH: 54
<212> TYPE: DNA
<213> ORGANISM: artificial
<220> FEATURE:
<223> OTHER INFORMATION: probe

<400> SEQUENCE: 26
tggcagcact ataggctgta ctgtccttac actcggacct cgtcgacatg catt           54

-continued

<210> SEQ ID NO 27
<211> LENGTH: 60
<212> TYPE: DNA
<213> ORGANISM: artificial
<220> FEATURE:
<223> OTHER INFORMATION: probe

<400> SEQUENCE: 27
tctgatgttt tttgtctggt gtggtaagtc ccttacactc ggacctcgtc gacatgcatt      60

<210> SEQ ID NO 28
<211> LENGTH: 55
<212> TYPE: DNA
<213> ORGANISM: artificial
<220> FEATURE:
<223> OTHER INFORMATION: probe

<400> SEQUENCE: 28
cctcaacaga tgttgtctca gctcctctta cactcggacc tcgtcgacat gcatt      55

<210> SEQ ID NO 29
<211> LENGTH: 54
<212> TYPE: DNA
<213> ORGANISM: artificial
<220> FEATURE:
<223> OTHER INFORMATION: probe

<400> SEQUENCE: 29
attgctggtg atcctttcca tccctgttac actcggacct cgtcgacatg catt      54

<210> SEQ ID NO 30
<211> LENGTH: 60
<212> TYPE: DNA
<213> ORGANISM: artificial
<220> FEATURE:
<223> OTHER INFORMATION: probe

<400> SEQUENCE: 30
tttctttttt aaccctgcgg gatgtggtat tcttacactc ggacctcgtc gacatgcatt      60

<210> SEQ ID NO 31
<211> LENGTH: 56
<212> TYPE: DNA
<213> ORGANISM: artificial
<220> FEATURE:
<223> OTHER INFORMATION: probe

<400> SEQUENCE: 31
tttaactttt gggccatcca ttcctggctt acactcggac ctcgtcgaca tgcatt      56

<210> SEQ ID NO 32
<211> LENGTH: 58
<212> TYPE: DNA
<213> ORGANISM: artificial
<220> FEATURE:
<223> OTHER INFORMATION: probe

<400> SEQUENCE: 32
ccctatcttt attgtgacga ggggtcgttg ttacactcgg acctcgtcga catgcatt      58

<210> SEQ ID NO 33
<211> LENGTH: 354
<212> TYPE: PRT
<213> ORGANISM: Burkholderia cenocepacia

<400> SEQUENCE: 33

-continued

```
Met Lys Pro Ser Gln Phe Ala Lys Gly Phe Gln Ala Arg Pro Asp Ile
1               5                   10                  15

Thr Thr Ser Glu Lys Arg Thr Ala Leu Asp Arg Leu Asn Ala Ile Asp
            20                  25                  30

Gly Ile Val Lys Ser Glu Thr Pro Thr Pro Ala Pro Thr Lys Ser Ala
            35                  40                  45

Lys Lys Asp Ile Ala Pro Pro Pro Ala Pro Glu Phe Thr Ile Asp Pro
        50                  55                  60

Ser Ile Asp Glu Ser Gln Gln Tyr Arg Ala Trp Arg Leu Glu Asn Arg
65                  70                  75                  80

Tyr Ala Pro Gly Gln Val Ile Glu Leu Pro Leu Lys Ala Ile Lys His
                85                  90                  95

Ser Pro Phe Asn Pro Arg His Phe Tyr Leu Lys Ser Ser Ile Ala Glu
            100                 105                 110

Leu Ala Val Asn Leu Ala Lys Gln Gly Gln Gln Gln Ala Ile His Val
            115                 120                 125

Ile Pro Asp Tyr Asp Asn Pro Gly Thr Tyr Phe Val Ser Asp Gly Gly
        130                 135                 140

Arg Arg Val Arg Ala Leu Lys Glu Ala Asn Lys Glu Ser Val Lys Ala
145                 150                 155                 160

Ile Val Ile Asp Val Pro Ile Gly Ile Gln Ser Tyr Lys Leu Gly Tyr
                165                 170                 175

Asp Leu Asn Val Gln Arg Asp Ser Gln Thr Val Phe Asp Asn Ala Val
            180                 185                 190

Val Trp Arg Arg Phe Leu Asp Asp Lys His Phe Gln Ser Gln Lys Glu
            195                 200                 205

Leu Ser Glu His Leu Gly Leu Asp Glu Ser Thr Val Ala Val Ala Leu
            210                 215                 220

Ser Ile Gly Lys Leu Pro Glu Ala Ile Met Gln Glu Met Val Ala Arg
225                 230                 235                 240

Pro Asp Arg Phe Gly Ser Asn Met Ala Tyr Gln Val Gly Arg Tyr His
                245                 250                 255

Asn Ala Arg Gly Thr Glu Ala Thr Leu Arg Leu Ile Asn Lys Ile Val
            260                 265                 270

Ser Asp Asp Leu Ser Thr Arg Gln Val Ser Asp Ile Val Lys Gly Arg
            275                 280                 285

Val Ala Ala Gln Glu Thr Pro Lys Pro Ala Gly Arg Gln Arg Tyr Ala
            290                 295                 300

Gln Arg Leu Glu Ile Lys Leu Gly Gly Lys Ser Val Gly Asp Leu Lys
305                 310                 315                 320

Ser Tyr Gly Glu Asp Arg Ile Glu Leu Arg Leu Arg Gly Leu Pro Lys
                325                 330                 335

Asp Lys Arg Asp Ala Ile Leu Glu Gln Leu Glu Arg Met Leu Leu Ser
            340                 345                 350

Glu His
```